(12) United States Patent
Paushkin et al.

(10) Patent No.: US 8,633,019 B2
(45) Date of Patent: Jan. 21, 2014

(54) METHODS FOR TREATING SPINAL MUSCULAR ATROPHY

(75) Inventors: Sergey V. Paushkin, Belle Mead, NJ (US); Nikolai Naryshkin, East Brunswick, NJ (US); Charles Romfo, Easton, PA (US); Ellen Welch, Califon, NJ (US)

(73) Assignee: PTC Therapeutics, Inc., South Plainfield, NJ (US)

(*) Notice: Subject to any disclaimer, the term of this patent is extended or adjusted under 35 U.S.C. 154(b) by 15 days.

(21) Appl. No.: 12/994,517

(22) PCT Filed: May 27, 2009

(86) PCT No.: PCT/US2009/003238
§ 371 (c)(1),
(2), (4) Date: Nov. 24, 2010

(87) PCT Pub. No.: WO2009/151546
PCT Pub. Date: Dec. 17, 2009

(65) Prior Publication Data
US 2011/0086833 A1    Apr. 14, 2011

Related U.S. Application Data

(60) Provisional application No. 61/128,932, filed on May 27, 2008.

(51) Int. Cl.
*C12Q 1/68* (2006.01)
*A01N 43/00* (2006.01)
*C12N 15/00* (2006.01)

(52) U.S. Cl.
USPC .................. 435/320.1; 435/6.1; 514/210

(58) Field of Classification Search
None
See application file for complete search history.

(56) References Cited

U.S. PATENT DOCUMENTS

| 2005/0054836 A1 | 3/2005 | Krainer et al. |
| 2007/0292408 A1 | 12/2007 | Singh et al. |
| 2011/0172284 A1 | 7/2011 | Paushkin et al. |

FOREIGN PATENT DOCUMENTS

| WO | WO 01/66129 | 9/2001 |
| WO | WO 2004/113867 | 12/2004 |
| WO | WO 2007/002390 | 1/2007 |
| WO | WO 2007/109211 | 9/2007 |
| WO | WO 2009/151546 | 12/2009 |
| WO | WO 2010/019236 | 2/2010 |
| WO | WO 2010/019243 | 2/2010 |

OTHER PUBLICATIONS

Zhang et al., An in vivo reporter system for measuring increased inclusion of exon 7 in SMN2 mRNA: potential therapy of SMA; Gene Therapy, vol. 8, pp. 1532-1538, 2001.*

Wilson et al., An SMA Project Report: Neural Cell-Based Assays Derived from Human Embryonic Stem Cells; Stem Cells and Development, vol. 16, 1027-1041, 2007.*
Singh et al., Modulating role of RNA structure in alternative splicing of a critical exon in the spinal muscular atrophy genes; NAR, vol. 35, No. 2, pp. 371-389, 2007.*
Wilson et al., An SMA Project Report: Neural Cell-Based Assays Derived from Human Embryonic Stem Cells; Stem Cells and Development, vol. 16, 1027-1041, 2007 Genbank record EF540695.1.*
Andreassi et al., 2001, "Aclarubicin treatment restores SMN levels to cells derived from type I spinal muscular atrophy patients," Human Molecular Genetics; 10(24):2841-2849.
Avila et al., 2007 "Trichostatin a increases SMN expression and survival in a mouse model of spinal muscular atrophy," J Clin Invest.; 117(3):659-71.
Bertini et al., 2005, "134th ENMC International Workshop: Outcome Measures and Treatment of Spinal Muscular Atrophy, Feb. 11-13, 2005, Naarden, The Netherlands," Neuromuscul Disord. 15(11):802-16.
Boda et al., 2004, "Survival motor neuron SMN1 and SMN2 gene promoters: identical sequences and differential expression in neurons and non-neuronal cells," Eur J Hum Genet.; 12(9):729-37.
Brahe et al., 2005, "Phenylbutyrate increases SMN gene expression in spinal muscular atrophy patients," Eur J Hum Genet.; 13(2):256-9.
Carrell et al., 2006, "Survival motor neuron function in motor axons is independent of functions required for small nuclear ribonucleoprotein biogenesis," Journal of Neuroscience; 26(43):11014-11022.
Cartegni et al., 2002, "Disruption of an SF2/ASF-dependent exonic splicing enhancer in SMN2 causes spinal muscular atrophy in the absence of SMN1," Nature Genetics; 30:377-384.
Cartegni et al., 2006, "Determinants of exon 7 splicing in the spinal muscular atrophy genes, SMN1 and SMN2," American Journal of Human Genetics; 78:63-77.
Echaniz-Laguna et al., 1999, "The promoters of the survival motor neuron gene (SMN) and its copy (SMNc) share common regulatory elements," Am J Hum Genet; 64(5): 1365-70.
Germain-Desprez et al., 2001, "The SMN genes are subject to transcriptional regulation during cellular differentiation," Gene; 279:109-117.
Gubitz et al., 2004 "The SMN complex," Exp Cell Res.; 296:51-6.
Iannaconne et al., 2002 "Outcome Measures for Pediatric Spinal Muscular Atrophy," Arch Neurol. 59:1445-1450.
Iannaconne et al., 2003, "Reliability of 4 Outcome Measures in Pediatric Spinal Muscular Atrophy," Arch Neurol; 60:1130-1136.
Jarecki et al., 2005 "Diverse small-molecule modulators of SMN expression found by high-throughput compound screening: early leads towards a therapeutic for spinal muscular atrophy," Hum Mol Genet.; 14(14):2003-18.
Kashima et al., 2003, "A negative element in SMN2 exon 7 inhibits splicing in spinal muscular atrophy," Nature Genetics; 34(4):460-463.
Kolb et al., 2006, "A novel cell immunoassay to measure survival of motor neurons protein in blood cells," BMC Neurology, 6:6.
Le et al., 2005, "SMNDELTA7, the major product of the centromeric survival motor neuron (SMN2) gene, extends survival in mice with spinal muscular atrophy and associates with full-length SMN," Human Molecular Genetics; 14(6):845-857.

(Continued)

Primary Examiner — Celine Qian
Assistant Examiner — Addison D Ault
(74) Attorney, Agent, or Firm — Jones Day

(57) ABSTRACT

The present invention provides nucleic acid constructs, methods for identifying and validating compounds that increase the inclusion of exon 7 of SMN2 into mRNA transcribed from the SMN2 gene, compounds and pharmaceutical compositions that increase levels of SMN protein produced from the SMN2 gene, and methods for use thereof in treating of SMA.

7 Claims, 9 Drawing Sheets

(56) References Cited

OTHER PUBLICATIONS

Lorson et al., 1999, "A single nucleotide in the SMN gene regulates splicing and is responsible for spinal muscular atrophy," Proc Natl Acad Sci USA; 96:6307-6311.

Lorson et al., 2000, "An exonic enhancer is required for inclusion of an essential exon in the SMA-determining gene SMN," Human Molecular Genetics; 9(2):259-265.

Lunn et al., 2004, "Indoprofen upregulates the survival motor neuron protein through a cyclooxygenase-independent mechanism," Chem Biol.; 11(11):1489-93.

Mattis et al., 2006, "Novel aminoglycosides increase SMN levels in spinal muscular atrophy fibroblasts," Human Genetics; pp. 1-13.

Mattis et al., 2008, "A SMN Δ7 read-through product confers functionality to the SMN Δ7 protein," Neuroscience Letters; 442:54-58.

Merlini et al., 2003, "Role of gabapentin in spinal muscular atrophy: results of a multicenter, randomized Italian study," J Child Neurol.; 18(8):537-41.

Monani et al., 1999, Promoter analysis of the human centromeric and telomeric survival motor neuron genes (SMNC and SMNT), Biochim Biophys Acta; 1445(3):330-6.

Paushkin et al.., 2002 "The SMN complex, an assemblyosome of ribonucleoproteins" Curr Opin Cell Biol., 14:305-12.

Rochette et al., 2001, "SMN gene duplication and the emergence of the SMN2 gene occurred in distinct hominids: SMN2 is unique to *Homo sapiens*." Human Genetics; 108(3):255-266.

Schmid et al., 2007, "Animal models of spinal muscular atrophy," Journal of Child Neurology; 22(8): 1004-1012.

Singh et al., 2004, "In vivo selection reveals combinatorial controls that define a critical exon in the spinal muscular atrophy genes," RNA: 10:1291-1305.

Sumner et al., 2006, "SMN mRNA and protein levels in peripheral blood: biomarkers for SMA clinical trials," Neurology, 66:1067-1073.

Sumner, 2006, "Therapeutics development for spinal muscular atrophy," NeuroRx; 3(2):235-245.

Wan, 2005, "The survival of motor neurons protein determines the capacity for snRNP assembly: biochemical deficiency in spinal muscular atrophy," Molec & Cell Biol, 25(13): 5543-5551.

Wolstencroft et al., 2005, "A non-sequence-specific requirement for SMN protein activity: the role of aminoglycosides in inducing elevated SMN protein levels," Hum Mol Genet, 14(9):1199-1210.

Yeo, 2005, "Splicing regulators: targets and drugs," Genome Biology; 6(12):240.

Yong et al., 2004, "Why do cells need an assembly machine for RNA—protein complexes," Trends in Cell Biology; 15(5):226-232.

Yuo et al., 2008, "5-(N-ethyl-N-isopropyl)-amiloride enhances SMN2 exon 7 inclusion and protein expression in spinal muscular atrophy cells," Annals of Neurology; 63(1):26-34.

Zhang et al., 2001, "An in vivo reporter system for measuring increased inclusion of exon 7 in SMN2 mRNA: potential therapy of SMA," Gene Therapy; 8:1532-1538.

Singh et al., 2007, "Modulating role of RNA structure in alternative splicing of a critical exon in the spinal muscular atrophy genes", Nucleic Acids Research: 35(2):371-389.

\* cited by examiner tagcttcttacccgtactccaccgttggcagcacgatcgcacgtcccacgtgaaccattggtaaaccctgatgggatccata
attccccaccacctcccatatgtccagattctcttgatgatgctgatgctttgggaagtatgttaatttcatggtacatgagtgg
ctatcatactggctattatatggtaagtaatcactcagcatcttttcctgacaattttttgtagttatgtgactttgttttgtaaatttat
aaaatactacttgcttctctcttttatattactaaaaaataaaaataaaaaaaatacaactgtctgaggcttaaattactcttgcattgt
ccctaagtataattttagttaattttaaaaagctttcatgctattgttagattattttgattatacacttttgaattgaaattatacttttct
aaataatgttttaatctctgatttgaaattgattgtagggaatggaaaagatgggataattttcataaatgaaaaatgaaattcttt
ttttttttttttttttttttgagacggagtcttgctctgttgcccaggctggagtgcaatggcgtgatcttggctcacagcaagctctg
cctcctggattcacgccattctcctgcctcagcctcagaggtagctgggactacaggtgcctgccaccacgcctgtctaattt
tttgtattttttgtaaagacagggtttcactgtgttagccaggatggtctcaatctcctgacccctgtgatccacccgcctcggcc
ttccaagagaaatgaaattttttaatgcacaaagatctggggtaatgtgtaccacattgaaccttggggagtatggcttcaaa
cttgtcactttatacgttagtctcctacggacatgttctattgtatttagtcagaacatttaaaattattttatttatttattttttttttttt
tttgagacggagtctcgctctgtcacccaggctggagtacagtggcgcagtctcggctcactgcaagctccgcctcccggg
ttcacgccattctcctgcctcagcctctccgagtagctgggactacaggcgcccgccaccacgcccggctaatttttttttattt
ttagtagagacggggtttcaccgtggtctcgatctcctgacctcgtgatccacccgcctcggcctcccaaagtgctgggatta
caagcgtgagccaccgcgcccggcctaaaattattttttaaaagtaagctcttgtgccctgctaaaattatgatgtgatattgtag
gcacttgtattttttagtaaattaatatagaagaaacaactgacttaaaggtgtatgttttttaaatgtatcatctgtgtgtgcccccat
taatattcttatttaaaagttaaggccagacatggtggcttacaactgtaatcccaacagtttgtgaggccgaggcaggcagat
cacttgaggtcaggagtttgagaccagcctggccaacatgatgaaaccttgtctctactaaaaataccaaaaaaaatttagcc
aggcatggtggcacatgcctgtaatccgagctacttgggaggctgtggcaggaaaattgctttaatctgggaggcagaggt
tgcagtgagttgagattgtgccactgcactccacccttggtgacagagtgagattccatctcaaaaaaagaaaaaggcctgg
cacggtggctcacacctataatcccagtactttgggaggtagaggcaggtggatcacttgaggttaggagttcaggaccag
cctggccaacatggtgactactccatttctactaaatacacaaaacttagcccagtggcgggcagttgtaatcccagctactt
gagaggttgaggcaggagaatcacttgaacctgggaggcagaggttgcagtgagccgagatcacaccgctgcactctag
cctggccaacagagtgagaatttgcggagggaaaaaaaagtcacgcttcagttgttgtagtataaccttggtatattgtatgta
tcatgaattcctcatttttaatgaccaaaaagtaataaatcaacagcttgtaatttgttttgagatcagttatctgactgtaacactgt
aggcttttgtgttttttaaattatgaaatatttgaaaaaaatacataatgtatatataaagtattggtataatttatgttctaaataactt
tcttgagaaataattcacatggtgtgcagtttacctttgaaagtatacaagttggctgggcacaatggctcacgcctgtaatcc
cagcactttgggaggccagggcaggtggatcacgaggtcaggagatcgagaccatcctggctaacatggtgaaacccg
tctctactaaaagtacaaaaacaaattagccgggcatgttggcgggcacctttgtcccagctgctcgggaggctgaggca
ggagagtggcgtgaacccaggaggtggagcttgcagtgagccgagattgtgccagtgcactccagcctgggcgacaga
gcgagactctgtctcaaaaaataaaataaaaaagaaagtatacaagtcagtggttttggtttcagttatgcaaccatcactac
aatttaagaacattttcatcaccccaaaaagaaaccctgttaccttcattttccccagcccctaggcagtcagtacactttctgtct
ctatgaatttgtctattttagatatttatatataaacggaattatacgatatgtggtcttttgtgtctggcttctttcacttagcatgctat
tttcaagattcatccatgctgtagaatgcaccagtactgcattccttcttattgctgaatattctgttgtttggttatatcacattttat
ccattcatcagttcatggacatttaggttgttttatttttgggctataatgaataatgttgctatgaacattcgtttgtgttcttttgttt
ttttggttttttgggttttttttgttttgttttttgttttttgagacagtcttgctctgtctcctaagctggagtgcagtggcatgatcttggc
ttactgcaagctctgcctcccgggttcacaccattctcctgcctcagcccgacaagtagctgggactacaggcgtgtgccac
catgcacggctaatttttgtattttagtagagatggggtttcaccgtgttagccaggatggtctcgatctcctgacctcgtgat
ctgcctgcctaggcctcccaaagtgctgggattacaggcgtgagccactgcacctggccttaagtgttttaatacgtcattg
ccttaagctaacaattcttaacctttgttctactgaagccacgtggttgagataggctctgagtctagctttaacctctatcttttt
gtcttagaaatctaagcagaatgcaaatgactaagaataatgttgttgaaataacataaaataggttataactttgatactcatta
gtaacaaatctttcaatacatcttacggtctgttaggtgtagattagtaatgaagtgggaagccactgcaagctagtatacatgt
agggaaagatagaaagcattgaagccagaagagagacagaggacatttgggctagatctgacaagaaaaacaaatgtttt
agtattaattttttgactttaaattttttttttatttagtgaatactggtgtttaatggtctcatttaataagtatgacacaggtagtttaa
ggtcatatatttatttgatgaaaataaggtataggccgggcacggtggctcacacctgtaatcccagcactttgggaggccg
aggcaggcggatcacctgaggtcgggagttagagactagcctcaacatggagaaaccccgtctctactaaaaaaaataca
aaattaggcgggcgtggtggtgcatgcctgtaatcccagctactcaggaggctgaggcaggagaattgcttgaacctggg

Figure 2A aggtggaggttgcggtgagccgagatcacctcattgcactccagcctgggcaacaagagcaaaactccatctcaaaaaaa
aaaaaataaggtataagcgggctcaggaacatcattggacatactgaaagaagaaaaatcagctgggcgcagtggctcac
gccggtaatcccaacactttgggaggccaaggcaggcgaatcacctgaagtcgggagttccagatcagcctgaccaacat
ggagaaaccctgtctctactaaaaatacaaaaactagccgggcatggtggcgcatgcctgtaatcccagctacttgggaggc
tgaggcaggagaattgcttgaaccgagaaggcggaggttgcggtgagccaagattgcaccattgcactccagcctgggc
aacaagagcgaaactccgtctcaaaaaaaaaggaagaaaaatatttttttaaattaattagtttatttattttttaagatggagttt
tgccctgtcacccaggctggggtgcaatggtgcaatctcggctcactgcaacctccgcctcctgggttcaagtgattctcctg
cctcagcttcccgagtagctgtgattacagccatatgccaccacgcccagccagttttgtgttttgtttgttttttgtttttttttttg
agagggtgtcttgctctgtcccccaagctggagtgcagcggcgcgatcttggctcactgcaagctctgcctcccaggttcac
accattctcttgcctcagcctcccgagtagctgggactacaggtgcccgccaccacacccggctaattttttgtgttttagta
gagatggggtttcactgtgttagccaggatggtctcgatctcctgacctttgatccaccgctcagcctcccaagtgctg
ggattataggcgtgagccactgtgcccggcctagtcttgtattttagtagagtcgggattctccatgttggtcaggctgttctc
caaatccgacctcaggtgatccgcccgccttggcctccaaaagtgcaaggcaaggcattacaggcatgagccactgtgac
cggcaatgttttaaattttttacatttaaatttattttttagagaccaggtctcactctattgctcaggctggagtgcaagggcac
attcacagctcactgcagccttgacctccagggctcaagcagtcctctcacctcagtttcccgagtagctgggactacagtg
ataatgccactgcacctggctaattttatttttatttattttttttgagacagagtcttgctctgtcacccaggctggagtgca
gtggtgtaaatctcagctcactgcagcctccgcctcctgggttcaagtgattctcctgcctcaacctcccaagtagctgggatt
agaggtccccaccaccatgcctggctaatttttttgtactttcagtagaaacggggttttgccatgttggccaggctgttctcgaa
ctcctgagctcaggtgatccaactgtctcggcctcccaaagtgctgggattacaggcgtgagccactgtgcctagcctgag
ccaccacgccggcctaattttaaattttttgtagagacagggtctcattatgttgcccaggtggtgtcaagctccaggtctca
agtgatcccccacctccgcctcccaaagttgtgggattgtaggcatgagccactgcaagaaaaccttaactgcagcctaat
aattgttttctttgggataacttttaaagtacattaaaagactatcaacttaatttctgatcatattttgttgaataaaataagtaaaat
gtcttgtgaaacaaaatgcttttaacatccatataaagctatctatatatagctatctatatctatatagctatttttttttaacttcctt
attttccttacagggttttagacaaaatcaaaaagaaggaaggtgctcacattccttaaatgtaaggagtaagtctgccagcat
tatgaaagtgaatcttacttttgtaaaactttatggtttgtggaaaacaaatgttttgaacatttaaaaagttcagatgttagaaag
ttgaaaggttaatgtaaaacaatcaatattaaagaattttgatgccaaaactattagataaaaggttaatctacatccctactaga
attctcatacttaactggttggttgtgtggaagaaacatactttcacaataaagagctttaggatatgatgccattttatatcacta
gtaggcagaccagcagactttttttattgtgatatgggataacctaggcatactgcactgtacactctgacatatgaagtgctc
tagtcaagtttaactggtgtccacagaggacatggtttaactggaattcgtcaagcctctggttctaatttctcatttgcaggaaa
tgctggcatagagcagcacggatccgaagacgccaaaaacataaagaaaggcccggcgccattctatcctctagaggat
ggaaccgctggagagcaactgcataaggctatgaagagatacgccctggttcctggaacaattgcttttacagatgcacata
tcgaggtgaacatcacgtacgcggaatacttcgaaatgtccgttcggttggcagaagctatgaaacgatatgggctgaatac
aaatcacagaatcgtcgtatgcagtgaaaactctcttcaattctttatgccggtgttgggcgcgttatttatcggagttgcagttg
cgcccgcgaacgacatttataatgaacgtgaattgctcaacagtatgaacatttcgcagcctaccgtagtgtttgtttccaaaa
agggggttgcaaaaaattttgaacgtgcaaaaaaaattaccaataatccagaaaattattatcatggattctaaaacggattacc
agggatttcagtcgatgtacacgttcgtcacatctcatctacctcccggttttaatgaatacgattttgtaccagagtccctttgatc
gtgacaaaacaattgcactgataatgaattcctctggatctactgggttacctaagggtgtggcccttccgcatagaactgcct
gcgtcagattctcgcatgccagagatcctatttttggcaatcaaatcattccggatactgcgattttaagtgttgttccattccatc
acggttttggaatgtttactacactcggatatttgatatgtggatttcgagtcgtcttaatgtatagatttgaagaagagctgtttt
acgatcccttcaggattacaaaattcaaagtgcgttgctagtaccaaccctattttcattcttcgccaaaagcactctgattgac
aaatacgatttatctaatttacacgaaattgcttctggggcgcacctctttcgaaagaagtcggggaagcggttgcaaaacg
cttccatcttccagggatacgacaaggatatgggctcactgagactacatcagctattctgattacacccgagggggatgat
aaaccgggcgcggtcggtaaagttgttccattttttgaagcgaaggttgtggatctggataccgggaaaacgctgggcgtta
atcagagaggcgaattatgtgtcagaggacctatgattatgtccggttatgtaaacaatccggaagcgaccaacgccttgatt
gacaaggatggatggctacattctggagacatagcttactgggacgaagacgaacacttcttcatagttgaccgcttgaagt
ctttaattaaatacaaaggatatcaggtggccccccgctgaattggaatcgatattgttacaacaccccaacatcttcgacgcg

Figure 2B ggcgtggcaggtcttcccgacgatgacgccggtgaacttcccgccgccgttgttgttttggagcacggaaagacgatgac
ggaaaaagagatcgtggattacgtcgccagtcaagtaacaaccgcgaaaaagttgcgcggaggagttgtgtttgtggacg
aagtaccgaaaggtcttaccggaaaactcgacgcaagaaaaatcagagagatcctcataaaggccaagaagggcggaa
agtccaaattgcgcggccgctaaatcgaaagtacaggactagccttcctagcaaccgcgggctgggagtctgagacatca
ctcaagatatatgctcggtaacgtatgctctagccatctaactattccctatgtcttataggg

Figure 2C tagcttcttacccgtactccaccgttggcagcacgatcgcacgtcccacgtgaaccattggtaaaccctgatgggatccata
attcccccaccacctcccatatgtccagattctcttgatgatgctgatgctttgggaagtatgttaatttcatggtacatgagtgg
ctatcatactggctattatatggtaagtaatcactcagcatcttttcctgacaattttttgtagttatgtgactttgttttgtaaatttat
aaaatactacttgcttctctctttatattactaaaaaataaaaataaaaaaatacaactgtctgaggcttaaattactcttgcattgt
ccctaagtataattttagttaattttaaaaagctttcatgctattgttagattattttgattatacacttttgaattgaaattatactttttct
aaataatgttttaatctctgatttgaaattgattgtagggaatggaaaagatgggataattttcataaatgaaaaatgaaattcttt
ttttttttttttttttttttgagacggagtcttgctctgttcccaggctggagtgcaatggcgtgatcttggctcacagcaagctctg
cctcctggattcacgccattctcctgcctcagcctcagaggtagctgggactacaggtgcctgccaccacgcctgtctaattt
tttgtatttttttgtaaagacagggtttcactgtgttagccaggatggtctcaatctcctgacccccgtgatccacccgcctcggcc
ttccaagagaaatgaaatttttttaatgcacaaagatctggggtaatgtgtaccacattgaaccttggggagtatggcttcaaa
cttgtcactttatacgttagtctcctacggacatgttctattgtattttagtcagaacatttaaaattattttattttattttattttttttttttt
tttgagacggagtctcgctctgtcacccaggctggagtacagtggcgcagtctcggctcactgcaagctccgcctcccggg
ttcacgccattctcctgcctcagcctctccgagtagctgggactacaggcgcccgccaccacgcccggctaattttttttattt
ttagtagagacggggtttcaccgtggtctcgatctcctgacctcgtgatccacccgcctcggcctcccaaagtgctgggatta
caagcgtgagccaccgcgcccggcctaaaattattttttaaaagtaagctcttgtgccctgctaaaattatgatgtgatattgtag
gcacttgtattttagtaaattaatatagaagaaacaactgacttaaaggtgtatgttttaaatgtatcatctgtgtgtgcccccat
taatattcttatttaaaagttaaggccagacatggtggcttacaactgtaatcccaacagtttgtgaggccgaggcaggcagat
cacttgaggtcaggagtttgagaccagcctggccaacatgatgaaaccttgtctctactaaaaatacaaaaaaaaatttagcc
aggcatggtggcacatgcctgtaatcccagctacttgggaggctgtggcaggaaaattgctttaatctgggaggcagaggt
tgcagtgagttgagattgtgccactgcactccacccttggtgacagagtgagattccatctcaaaaaaagaaaaaggcctgg
cacggtggctcacacctataatcccagtactttgggaggtagaggcaggtggatcacttgaggttaggagttcaggaccag
cctggccaacatggtgactactccatttctactaaatacacaaaacttagcccagtggcgggcagttgtaatcccagctactt
gagaggttgaggcaggagaatcacttgaacctgggaggcagaggttgcagtgagccgagatcacaccgctgcactctag
cctggccaacagagtgagaatttgcggagggaaaaaaaagtcacgcttcagttgttgtagtataaccttggtatattgtatgta
tcatgaattcctcattttaatgaccaaaaagtaataaatcaacagcttgtaatttgttttgagatcagttatctgactgtaacactgt
aggcttttgtgttttttaaattatgaaatatttgaaaaaaatacataatgtatatataaagtattggtataatttatgttctaaataactt
tcttgagaaataattcacatggtgtgcagtttaccttttgaaagtatacaagttggctgggcacaatggctcacgcctgtaatcc
cagcactttgggaggccagggcaggtggatcacgaggtcaggagatcgagaccatcctggctaacatggtgaaaccccg
tctctactaaaagtacaaaaacaaattagccgggcatgttggcgggcaccttttgtcccagctgctcgggaggctgaggca
ggagagtggcgtgaacccaggaggtggagcttgcagtgagccgagattgtgccagtgcactccagcctgggcgacaga
gcgagactctgtctcaaaaaataaaataaaaaagaaagtatacaagtcagtggttttggttttcagttatgcaaccatcactac
aatttaagaacattttcatcaccccaaaaagaaaccctgttaccttcattttccccagcccctaggcagtcagtacactttctgtct
ctatgaatttgtctattttagatattatatataaacggaattatacgatatgtggtcttttgtgtctggcttctttcacttagcatgctat
tttcaagattcatccatgctgtagaatgcaccagtactgcattccttcttattgctgaatattctgttgtttggttatatcacatttat
ccattcatcagttcatggacatttaggttgtttttattttgggctataatgaataatgttgctatgaacattcgtttgtgttcttttgttt
ttttggttttttgggttttttttgttttgttttgttttgagacagtcttgctctgtctcctaagctggagtgcagtggcatgatcttggc
ttactgcaagctctgcctcccgggttcacaccattctcctgcctcagcccgacaagtagctgggactacaggcgtgtgccac
catgcacggctaattttttgtattttagtagagatggggtttcaccgtgttagccaggatggtctcgatctcctgacctcgtgat
ctgcctgccaggcctcccaaagtgctgggattacaggcgtgagccactgcacctggccttaagtgttttaatacgtcattg
cctaagctaacaattcttaacctttgttctactgaagccacgtggttgagataggctctgagtctagcttttaacctctatcttttt
gtcttagaaatctaagcagaatgcaaatgactaagaataatgttgttgaaataacataaaataggttataactttgatactcatta
gtaacaaatcttcaatacatcttacggtctgttaggtgtagattagtaatgaagtgggaagccactgcaagctagtatacatgt
agggaaagatagaaagcattgaagccagaagagagacagaggacatttgggctagatctgacaagaaaaacaaatgtttt
agtattaattttgactttaaatttttttttttttatttagtgaatactggtgtttaatggtctcattttaataagtatgacacaggtagtttaa
ggtcatatatttttatttgatgaaaataaggtataggccgggcacggtggctcacacctgtaatcccagcactttgggaggccg
aggcaggcggatcacctgaggtcgggagttagagactagcctcaacatggagaaaccccgtctctactaaaaaaaataca
aaattaggcgggcgtggtggtgcatgcctgtaatcccagctactcaggaggctgaggcaggagaattgcttgaacctggg

Figure 3A aggtggaggttgcggtgagccgagatcacctcattgcactccagcctgggcaacaagagcaaaactccatctcaaaaaaa
aaaaaataaggtataagcgggctcaggaacatcattggacatactgaaagaagaaaaatcagctgggcgcagtggctcac
gccggtaatcccaacactttgggaggccaaggcaggcgaatcacctgaagtcgggagttccagatcagcctgaccaacat
ggagaaaccctgtctctactaaaaatacaaaaactagccgggcatggtggcgcatgcctgtaatcccagctacttgggaggc
tgaggcaggagaattgcttgaaccgagaaggcggaggttgcggtgagccaagattgcaccattgcactccagcctgggc
aacaagagcgaaactccgtctcaaaaaaaaaaggaagaaaaatatttttttaaattaattagtttatttattttttaagatggagttt
tgccctgtcacccaggctgggglgcaatggtgcaatctcggctcactgcaacctccgcctcctgggttcaagtgattctcctg
cctcagcttcccgagtagctgtgattacagccatatgccaccacgcccagcctgatttttgtgttttgttttgttttttgttttttttttttg
agagggtgtcttgctctgtcccccaagctggagtgcagcggcgcgatcttggctcactgcaagctctgcctcccaggttcac
accattctcttgcctcagcctcccgagtagctgggactacaggtgcccgccaccacacccggctaattttttgtgttttagta
gagatggggtttcactgtgttagccaggatggtctcgatctcctgacctttgatccaccccgcctcagcctcccaagtgctg
ggattataggcgtgagccactgtgcccggcctagtcttgtatttttagtagagtcgggatttctccatgttggtcaggctgttctc
caaatccgacctcaggtgatccgcccgccttggcctccaaaagtgcaaggcaaggcattacaggcatgagccactgtgac
cggcaatgtttttaaatttttacatttaaattttatttttagagaccaggtctcactctattgctcaggctggagtgcaagggcac
attcacagctcactgcagccttgacctccagggctcaagcagtcctctcacctcagtttcccgagtagctgggactacagtg
ataatgccactgcacctggctaattttattttattttattttttttttgagacagagtcttgctctgtcacccaggctggagtgca
gtggtgtaaatctcagctcactgcagcctccgcctcctgggttcaagtgattctcctgcctcaacctcccaagtagctgggatt
agaggtccccaccaccatgcctggctaattttttgtactttcagtagaaacgggtttgccatgttggccaggctgttctcgaa
ctcctgagctcaggtgatccaactgtctcggcctcccaaagtgctgggattacaggcgtgagccactgtgcctagcctgag
ccaccacgccggcctaatttttaaatttttgtagagacagggtctcattatgttgcccagggtggtgtcaagctccaggtctca
agtgatcccctacctccgcctcccaaagtgtgggattgtaggcatgagccactgcaagaaaaccttaactgcagcctaat
aattgttttctttgggataactttaaagtacattaaaagactatcaacttaatttctgatcatattttgttgaataaaataagtaaaat
gtcttgtgaaacaaaatgcttttaacatccatataaagctatctatatatagctatctatatctatatagctattttttttaacttccttt
attttccttacagggttttagacaaaatcaaaaagaaggaaggtgctcacattccttaaatataaggagtaagtctgccagcat
tatgaaagtgaatcttacttttgtaaaactttatggtttgtggaaaacaaatgtttttgaacatttaaaaagttcagatgttagaaag
ttgaaaggttaatgtaaaacaatcaatattaaagaattttgatgccaaaactattagataaaaggttaatctacatccctactaga
attctcatacttaactggttggttgtgtggaagaaacatactttcacaataaagagctttaggatatgatgccatttatatcacta
gtaggcagaccagcagacttttttttattgtgatatgggataacctaggcatactgcactgtacactctgacatatgaagtgctc
tagtcaagtttaactggtgtccacagaggacatggtttaactggaattcgtcaagcctctggttctaatttctcatttgcaggaaa
tgctggcatagagcagcacggatccgaagacgccaaaaacataaagaaaggcccggcgccattctatcctctagaggat
ggaaccgctggagagcaactgcataaggctatgaagagatacgccctggttcctggaacaattgcttttacagatgcacata
tcgaggtgaacatcacgtacgcggaatacttcgaaatgtccgttcggttggcagaagctatgaaacgatatgggctgaatac
aaatcacagaatcgtcgtatgcagtgaaaactctcttcaattctttatgccggtgttgggcgcgttatttatcggagttgcagtt
gcccccgcgaacgacatttataatgaacgtgaattgctcaacagtatgaacatttcgcagcctaccgtagtgtttgttccaaaa
agggggttgcaaaaaattttgaacgtgcaaaaaaaattaccaataatccagaaaattattatcatggattctaaaacggattacc
agggatttcagtcgatgtacacgttcgtcacatctcatctacctcccggttttaatgaatacgattttgtaccagagtcctttgatc
gtgacaaaacaattgcactgataatgaattcctctgatctactgggttacctaagggtgtggcccttccgcatagaactgcct
gcgtcagattctcgcatgccagagatcctatttttggcaatcaaatcattccggatactgcgattttaagtgttgttccattccatc
acggttttggaatgtttactacactcggatatttgatatgtggatttcgagtcgtcttaatgtatagatttgaagaagagctgttttt
acgatcccttcaggattacaaaattcaaagtgcgttgctagtaccaacccctattttcattcttcgccaaaagcactctgattgac
aaatacgatttatctaatttacacgaaattgcttctggggcgcacctctttcgaaagaagtcggggaagcggttgcaaaacg
cttccatcttccagggatacgacaaggatatgggctcactgagactacatcagctattctgattacacccgagggggatgat
aaaccgggcgcggtcggtaaagttgttccattttttgaagcgaaggttgtggatctggataccgggaaaacgctgggcgtta
atcagagaggcgaattatgtgtcagaggacctatgattatgtccggttatgtaaacaatccggaagcgaccaacgccttgatt
gacaaggatggatggctacattctggagacatagcttactgggacgaagacgaacacttcttcatagttgaccgcttgaagt
ctttaattaaatacaaaggatatcaggtggcccccgctgaattggaatcgatattgttacaacaccccaacatcttcgacgcg
ggcgtggcaggtcttcccgacgatgacgccggtgaacttcccgccgccgttgttgtttggagcacggaaagacgatgac ggaaaaagagatcgtggattacgtcgccagtcaagtaacaaccgcgaaaaagttgcgcggaggagttgtgtttgtggacg
aagtaccgaaaggtcttaccggaaaactcgacgcaagaaaaatcagagagatcctcataaaggccaagaagggcggaa
agtccaaattgcgcggccgctaaatcgaaagtacaggactagccttcctagcaaccgcgggctgggagtctgagacatca
ctcaagatatatgctcggtaacgtatgctctagccatctaactattccctatgtcttataggg

Figure 3C

METHODS FOR TREATING SPINAL MUSCULAR ATROPHY

This application is a national stage filing under 35 U.S.C. §371 of International Application No. PCT/US2009/003238, filed on May 27, 2009, which claims priority benefit of U.S. provisional application No. 61/128,932, filed on May 27, 2008, each of which is incorporated herein by reference in its entirety.

INTRODUCTION

The present invention relates to methods for treating for Spinal Muscular Atrophy and methods for identifying and validating compounds for use in treating this devastating neurological disease.

BACKGROUND

Spinal Muscular Atrophy ("SMA"), in its broadest sense, describes a collection of inherited and acquired central nervous system (CNS) diseases characterized by motor neuron loss in the spinal cord and brainstem causing muscle weakness and atrophy. The most common form of SMA is caused by mutation of the Survival Motor Neuron ("SMN") gene, and manifests over a wide range of severity affecting infants through adults.

Infantile SMA is one of the most severe forms of this neurodegenerative disorder. The onset is usually sudden and dramatic. Some of the symptoms include: muscle weakness, poor muscle tone, weak cry, limpness or a tendency to flop, difficulty sucking or swallowing, accumulation of secretions in the lungs or throat, feeding difficulties and increased susceptibility to respiratory tract infections. The legs tend to be weaker than the arms and developmental milestones, such as lifting the head or sitting up, cannot be reached. In general, the earlier the symptoms appear, the shorter the lifespan. Shortly after symptoms appear, the motor neuron cells quickly deteriorate. The disease can be fatal and has no known cure. The course of SMA is directly related to the severity of weakness. Infants with a severe form of SMA frequently succumb to respiratory disease due to weakness in the muscles that support breathing. Children with milder forms of SMA live much longer, although they may need extensive medical support, especially those at the more severe end of the spectrum. Disease progression and life expectancy strongly correlate with the subject's age at onset and the level of weakness. The clinical spectrum of SMA disorders has been divided into the following five groups:

(a) In Utero SMA (Type 0 SMA; before birth): Type 0, also known as very severe SMA, is the most severe form of SMA and begins before birth. Usually, the first symptom of type 0 is reduced movement of the fetus that is first seen between 30 and 36 weeks of the pregnancy. After birth, these newborns have little movement and have difficulties with swallowing and breathing.

(b) Infantile SMA (Type 1 SMA or Werdnig-Hoffmann disease; generally 0-6 months): Type 1 SMA, also known as severe infantile SMA or Werdnig Hoffmann disease, is the very severe, and manifests at birth or within 6 months of life. Patients never achieve the ability to sit, and death usually occurs within the first 2 years without ventilatory support.

(c) Intermediate SMA (Type 2 SMA; generally 7-18 months): Patients with Type 2 SMA, or intermediate SMA, achieve the ability to sit unsupported, but never stand or walk unaided. The onset of weakness is usually recognized some time between 6 and 18 months. Prognosis in this group is largely dependent on the degree of respiratory involvement.

(d) Juvenile SMA (Type 3 or Kugelberg-Welander disease; generally >18 months): Type 3 SMA describes those who are able to walk independently at some point during their disease course, but often become wheelchair bound during youth or adulthood.

(e) Adult SMA (Type 4 SMA): Weakness usually begins in late adolescence in tongue, hands, or feet then progresses to other areas of the body. The course of adult disease is much slower and has little or no impact on life expectancy.

The SMA disease gene has been mapped by linkage analysis to a complex region of chromosome 5q. In humans, this region has a large inverted duplication; consequently, there are two copies of the SMN gene. SMA is caused by a mutation or deletion of the telomeric copy of the gene (SMN1) in both chromosomes, resulting in the loss of SMN1 gene function. However, all patients retain a centromeric copy of the gene (SMN2), and its copy number in SMA patients has been implicated as having an important modifying effect on disease severity; i.e., an increased copy number of SMN2 is observed in less severe disease. Nevertheless, SMN2 is unable to compensate completely for the loss of SMN1 function, because the SMN2 gene produces reduced amounts of full-length RNA and is less efficient at making protein, although, it does so in low amounts. More particularly, the SMN1 and SMN2 genes differ by five nucleotides; one of these differences—a translationally silent C to T substitution in an exonic splicing region—results in frequent exon 7 skipping during transcription of SMN2. As a result, the majority of transcripts produced from SMN2 lack exon 7 (SMNΔEx7), and encode a truncated protein that has an impaired function and is rapidly degraded.

The SMN protein is thought to play a role in RNA processing and metabolism, having a well characterized function of regulating the assembly of a specific class of RNA-protein complexes called snRNPs. SMN may have other functions in motor neurons, however its role in preventing the selective degeneration of motor neurons is not known.

In most cases, a diagnosis of SMA can be made on the basis of clinical symptoms and by the SMN gene test, which determines whether there is at least one copy of the SMN1 gene by detecting its unique sequences (that distinguish it from the almost identical SMN2) in exon 7 and exon 8. However, other forms of SMA are caused by mutation of other genes, some known and others not defined. In some cases, when the SMN gene test is not possible, or does not show any abnormality, other tests such as an electromyography (EMG) or muscle biopsy may be indicated.

Medical care for SMA patients is supportive, including, respiratory, nutritional and rehabilitation care; there is no drug known to otherwise alter the course of the disease. Current treatment for SMA consists of prevention and management of the secondary effect of chronic motor unit loss. The major management issue in Type 1 SMA is the prevention and early treatment of pulmonary problems, which are the cause of death in the majority of the cases. While some infants afflicted with SMA grow to be adults, those with Type 1 SMA have a life expectancy of less than two years.

As a result of the progress made in understanding the genetic basis and pathophysiology of SMA, several strategies for treatment have been explored, but none have yet demonstrated success. For example, gene replacement (of SMN1) and cell replacement (using differentiated ES cells) strategies are being tested in animals. However, these approaches to treat SMA will require many more years of investigation before they can be applied to humans. Other approaches under exploration include searching for drugs that increase SMN levels, enhance residual SMN function, or compensate for its loss.

A system designed for identifying compounds that increase the inclusion of exon 7 of SMN2 into mRNA transcribed from the SMN2 gene has been reported (Zhang et al., 2001, Gene Therapy 8:1532-1538). However, the compounds identified using this system have been shown not to modulate inclusion of exon 7 into mRNA transcribed from the SMN2 gene, but rather to increase SMN protein levels by promoting transcriptional readthrough of a stop codon (see Lunn et al., 2004, Chemistry & Biology 11:1489-1493 and Heemskerk et al., 2007, International Patent Application No. PCT/US2007/006772, published as WO97/109211).

Drugs such as indoprofen or aminoglycosides, which enhance expression of the SMN protein from SMN2 by promoting translational read-through of a stop codon, have been assessed in cell culture, but have poor central nervous system penetration. Chemotherapeutic agents, such as aclarubicin, have been shown to increase SMN protein in cell culture; however, the toxicity profile of these drugs prohibits long-term use in SMA patients. Some drugs under clinical investigation for the treatment of SMA include transcription activators, such as histone deacetylase ("HDAC") inhibitors (e.g., butyrates, valproic acid, and hydroxyurea), the goal being to increase transcription of the SMN2 gene. However, the use of the HDAC inhibitors results in a global (nonspecific) increase in transcription and gene expression. In an alternative approach, the use of neuroprotectants that have demonstrated modest efficacy in other neurodegenerative conditions (e.g., riluzole, which is used in patients with ALS) have been chosen for investigation. Such strategies are not aimed at SMN for the treatment of SMA, but instead, are being explored to protect the SMN-deficient motor neurons from neurodegeneration.

Despite the progress made in understanding the genetic basis and pathophysiology of SMA, no therapy exists to alter the course of SMA, one of the most devastating childhood neurological diseases.

SUMMARY OF THE INVENTION

The present invention relates to methods for the treatment of SMA by enhancing the inclusion of exon 7 of SMN2 into mRNA transcribed from the SMN2 gene. Compounds that enhance the inclusion of exon 7 of SMN2 into mRNA transcribed from the SMN2 gene increase levels of SMN protein produced from the SMN2 gene, and thus can be used to treat SMA in a human subject in need thereof.

SMA is caused by deletion or mutation of the SMN1 gene, resulting in selective degeneration of SMN-deficient motor neurons. Although human subjects retain a copy of SMN2 with its predominant gene product SMNΔEx7, the small amount of full-length SMN expressed does not fully compensate for the loss of SMN1 function. Compounds that enhance the inclusion of exon 7 of SMN2 into mRNA transcribed from the SMN2 gene and as a result increase expression of stable and functional SMN protein are described. Such compounds can be used in therapeutic regimens for the treatment of SMA in human subjects in need thereof.

The invention is based, in part, on the Applicants discovery of a nucleic acid construct comprising a minigene that encodes a truncated SMN-reporter fusion protein comprising a truncated SMN protein and a reporter protein and which reproduces the exon 7 splicing reaction of SMN2 that results in exon 7 skipping in the majority of wild-type SMN2 transcripts. The inclusion of exon 7 is increased when the nucleic acid construct is contacted with a compound, and as a result, there is an increase in the expression of the fusion protein encoded by the minigene. Therefore, the nucleic acid construct may be used in assays to identify compounds that modulate the inclusion of exon 7 of SMN2 into mRNA transcribed from the SMN2 gene.

In one embodiment, the nucleic acid construct comprises a minigene, wherein the minigene comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2. In one aspect, the minigene comprises a start codon 5' to the nucleic acid residues of exon 6 of SMN, wherein the first codon of the coding sequence of the reporter gene and the start codon of the minigene are in the same open reading frame. In accordance with the invention, the nucleic acid construct described in this embodiment may be transfected into host cells and the cells may be used to identify compounds that modulate the inclusion of exon 7 of SMN2 into mRNA transcribed from the SMN2 gene.

In another embodiment, the nucleic acid construct comprises a minigene, wherein the minigene comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first start codon of the fragment of the nucleic acid residues of exon 6 of SMN and the first codon of the coding sequence of the reporter gene are in the same open reading frame. In accordance with the invention, the nucleic acid construct described in this embodiment may be transfected into host cells and the cells may be used to identify compounds that modulate the inclusion of exon 7 of SMN2 into mRNA transcribed from the SMN2 gene.

In another embodiment, the nucleic acid construct comprises a minigene, wherein the minigene comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first codon of the coding sequence of the reporter gene and the first start codon of the minigene are in the same open reading frame. In accordance with the invention, the nucleic acid construct described in this embodiment may be transfected into host cells and the cells may be used to identify compounds that modulate the inclusion of exon 7 of SMN2 into mRNA transcribed from the SMN2 gene.

In another embodiment, the nucleic acid construct comprises a minigene, wherein the minigene comprises, in 5' to 3' order: nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first amino acid sequence include a start codon; (iii) the nucleic acid residues encoding the first and second amino acid sequences permit removal of an intron via mRNA splicing, and (iv) the first codon of the coding sequence of the reporter gene and the start codon of the nucleic acid residues encoding the first amino acid sequence are in the same open reading frame. In accordance with the invention, the nucleic acid construct described in this embodiment may be transfected into host cells and the cells may be used to identify compounds that modulate the inclusion of exon 7 of SMN2 into mRNA transcribed from the SMN2 gene.

In another embodiment, the nucleic acid construct comprises a minigene, wherein the minigene comprises, in 5' to 3' order: a start codon, nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first and second amino acid sequences permit removal of an intron via mRNA splicing, and (iii) the first codon of the coding sequence of the reporter gene and the first start codon of the minigene are in the same open reading frame. In accordance with the invention, the nucleic acid construct described in this embodiment may be transfected into host cells and the cells may be used to identify compounds that modulate the inclusion of exon 7 of SMN2 into mRNA transcribed from the SMN2 gene.

The invention also provides host cells containing the nucleic acid constructs described herein. A host cell may be transformed or transfected with one or several of the nucleic acid constructs described herein. In one embodiment, the host cell is transiently transfected with a nucleic acid construct described herein. In an alternative embodiment, the host cell is stably transfected with a nucleic acid construct described herein. In one specific embodiment, the host cell is a mammalian cell. In another specific embodiment, the host cell is a human cell. Host cells containing a nucleic acid construct described herein may be used in the screening assays described herein.

The invention provides assays for the identification of compounds that enhance the inclusion of exon 7 of SMN2 into mRNA transcribed from the SMN2 gene. In one embodiment, an assay of the present invention includes a method for the identification of a compound that increases the inclusion of exon 7 of SMN2 into mRNA transcribed from the SMN2 gene comprising the steps of: (a) contacting a compound with a host cell containing a nucleic acid construct comprising a minigene, wherein the minigene comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; and (b) detecting the activity or amount of a fusion protein encoded by the minigene, wherein an increase in the activity or amount of the fusion protein expressed by the host cell in the presence of the compound relative to the activity or amount of the fusion protein expressed by the host cell in the absence of the compound or the presence of a negative control compound, or relative to a previously determined reference range indicates that the compound increases the inclusion of exon 7 of SMN2 into mRNA transcribed from the SMN2 gene. In one aspect, the minigene comprises a start codon 5' to the nucleic acid residues of exon 6 of SMN, wherein the first codon of the coding sequence of the reporter gene and the start codon of the minigene are in the same open reading frame. In some embodiments, a compound that enhances the inclusion of exon 7 of SMN2 into mRNA transcribed from the SMN2 gene is identified if the activity or amount of the fusion protein expressed by the host cell in the presence of the compound is increased relative to a previously determined reference range.

In another embodiment, an assay of the present invention includes a method for the identification of a compound that increases the inclusion of exon 7 of SMN2 into mRNA transcribed from the SMN2 gene comprising the steps of: (a) contacting a compound with a host cell containing a nucleic acid construct comprising a minigene, wherein the minigene comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first start codon of the fragment of the nucleic acid residues of exon 6 of SMN and the first codon of the coding sequence of the reporter gene are in the same open reading frame; and (b) detecting the activity or amount of a fusion protein encoded by the minigene, wherein an increase in the activity or amount of the fusion protein expressed by the host cell in the presence of the compound relative to the activity or amount of the fusion protein expressed by the host cell in the absence of the compound or the presence of a negative control compound, or relative to a previously determined reference range indicates that the compound increases the inclusion of exon 7 of SMN2 into mRNA transcribed from the SMN2 gene. In some embodiments, a compound that increases the inclusion of exon 7 of SMN2 into mRNA transcribed from the SMN2 gene is identified if the activity of the fusion protein expressed by the host cell in the presence of the compound is increased relative to a previously determined reference range.

In another embodiment, an assay of the present invention includes a method for the identification of a compound that increases the inclusion of exon 7 of SMN2 into mRNA transcribed from the SMN2 gene comprising the steps of: (a)

contacting a compound with a host cell containing a nucleic acid construct comprising a minigene, wherein the minigene comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first codon of the coding sequence of the reporter gene and the first start codon of the minigene are in the same open reading frame; and (b) detecting the activity or amount of a fusion protein encoded by the minigene, wherein an increase in the activity or amount of the fusion protein expressed by the host cell in the presence of the compound relative to the activity or amount of the fusion protein expressed by the host cell in the absence of the compound or the presence of a negative control compound, or relative to a previously determined reference range indicates that the compound increases the inclusion of exon 7 of SMN2 into mRNA transcribed from the SMN2 gene. In some embodiments, a compound that enhances the inclusion of exon 7 of SMN2 into mRNA transcribed from the SMN2 gene is identified if the activity of the fusion protein expressed by the host cell in the presence of the compound is increased relative to a previously determined reference range.

In another embodiment, an assay of the present invention includes a method for the identification of a compound that increases the inclusion of exon 7 of SMN2 into mRNA transcribed from the SMN2 gene comprising the steps of: (a) contacting a compound with a host cell containing a nucleic acid construct comprising a minigene, wherein the minigene comprises, in 5' to 3' order: nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first and second amino acid sequences include a start codon; (iii) the nucleic acid residues encoding the first and second amino acid sequences permit removal of an intron via mRNA splicing, and (iv) the first codon of the coding sequence of the reporter gene and the start codon of the nucleic acid residues encoding the first amino acid sequence are in the same open reading frame; and (b) detecting the activity or amount of a fusion protein encoded by the minigene, wherein an increase in the activity or amount of the fusion protein expressed by the host cell in the presence of the compound relative to the activity or amount of the fusion protein expressed by the host cell in the absence of the compound or the presence of a negative control compound, or relative to a previously determined reference range indicates that the compound increases the inclusion of exon 7 of SMN2 into mRNA transcribed from the SMN2 gene. In some embodiments, a compound that enhances the inclusion of exon 7 of SMN2 into mRNA transcribed from the SMN2 gene is identified if the activity of the fusion protein expressed by the host cell in the presence of the compound is increased relative to a previously determined reference range.

In another embodiment, an assay of the present invention includes a method for the identification of a compound that increases the inclusion of exon 7 of SMN2 into mRNA transcribed from the SMN2 gene comprising the steps of: (a) contacting a compound with a host cell containing a nucleic acid construct comprising a minigene, wherein the minigene comprises, in 5' to 3' order: a start codon, nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first and second amino acid sequences permit removal of an intron via mRNA splicing, and (iii) the first codon of the coding sequence of the reporter gene and the first start codon of the minigene are in the same open reading frame; and (b) detecting the activity or amount of a fusion protein encoded by the minigene, wherein an increase in the activity or amount of the fusion protein expressed by the host cell in the presence of the compound relative to the activity or amount of the fusion protein expressed by the host cell in the absence of the compound or the presence of a negative control compound, or relative to a previously determined reference range indicates that the compound increases the inclusion of exon 7 of SMN2 into mRNA transcribed from the SMN2 gene. In some embodiments, a compound that enhances the inclusion of exon 7 of SMN2 into mRNA transcribed from the SMN2 gene is identified if the activity of the fusion protein expressed by the host cell in the presence of the compound is increased relative to a previously determined reference range.

In some embodiments, in addition to, or as an alternative to, detecting the activity of the fusion protein, the amount of the fusion protein can be detected. In accordance with such embodiments, a compound that increases the inclusion of exon 7 of SMN2 into mRNA transcribed from the SMN2 gene is identified if the amount of the fusion protein expressed by the host cell in the presence of the compound is increased relative to: (i) the amount of the fusion protein expressed by the host cell in the absence of the compound or (ii) the amount of the fusion protein expressed by the host cell in presence of a negative control (e.g., PBS or DMSO), or (iii) a previously determined reference range.

In certain embodiments, the terms "increased" and "greater" in the context of the amount or activity of a fusion protein refer to: (i) a 10%, 20%, 30%, 40%, 50%, 75%, 100%, 150%, 200% or more increase; (ii) a 1.5, 2, 3, 4, or 5 fold or more increase; or (iii) a statistically significant increase in the amount or activity of the fusion protein relative to a control. In certain embodiments, the terms "increased" and "greater" in the context of the amount of mRNA transcript containing exon 7 of SMN2 or a fragment thereof refer to: (i) a 10%, 20%, 30%, 40%, 50% or more increase; (ii) a 1.5, 2, 3, 4, or 5 fold or more increase; or (iii) a statistically significant increase in the amount of mRNA transcript containing exon 7 of SMN2 or a fragment thereof relative to a control. In a specific embodiment, a statistically significant increase is a p value of less than 0.1, 0.05, 0.01, or 0.001.

In some embodiments, in addition to, or as an alternative to, detecting the amount and/or activity of the fusion protein, the amount of mRNA containing exon 7 of SMN2 transcribed from the minigene can be detected. In accordance with such embodiments, a compound that increases the inclusion of exon 7 of SMN2 into mRNA transcribed from the SMN2 gene is identified if the amount of mRNA containing exon 7 of SMN2 transcribed from the minigene is increased in the presence of the compound relative to the amount of mRNA containing exon 7 of SMN2 transcribed from the minigene in the absence of the compound, in the presence of a negative control, or relative to a previously determined reference range. As a result of such assays, compounds that specifically increase the inclusion of exon 7 of SMN2 during splicing may be selected.

In another embodiment, an assay of the present invention includes a method for the identification and/or validation of a compound that increases the inclusion of exon 7 of SMN2 into mRNA transcribed from the SMN2 gene comprising the steps of: (a) contacting a first concentration of a compound with a first host cell containing a first nucleic acid construct which comprises a first minigene, wherein the first minigene comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a first reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (b) detecting the activity or amount of a first fusion protein encoded by the first minigene; and (c) comparing the activity or amount of the first fusion protein with the activity or amount of a second fusion protein expressed by a second host cell contacted with a second concentration of the compound, wherein the first and second concentrations of the compound are equivalent, and wherein the second host cell contains a second nucleic acid construct comprising a second minigene encoding the second fusion protein which comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a second reporter gene lacking a start codon, wherein a single guanine residue is inserted after nucleic acid residue 48 of exon 7 of SMN2; wherein a compound that increases the inclusion of exon 7 of SMN2 into mRNA transcribed from the SMN2 gene is identified and/or validated if the activity or amount of the first fusion protein expressed by the first host cell is increased in the presence of the compound relative to the activity or amount of the first fusion protein expressed by the first host cell in the absence of the compound or the presence of a negative control (e.g., PBS or DMSO), or relative to a previously determined reference range, and the activity or amount of the second fusion protein expressed by the second host cell is not significantly altered in the presence of the compound relative to the absence of the compound or the presence of a negative control (e.g., PBS or DMSO), or relative to a previously determined reference range. In one aspect, the first and second minigenes each comprise a start codon 5' to the nucleic acid residues of exon 6 of SMN, wherein the first codon of the coding sequence of the first reporter gene and the start codon of the first minigene are in the same open reading frame, and wherein the first codon of the coding sequence of the second reporter gene and the start codon of the second minigene are in the same open reading frame.

In another embodiment, an assay of the present invention includes a method for the identification and/or validation of a compound that increases the inclusion of exon 7 of SMN2 into mRNA transcribed from the SMN2 gene comprising the steps of: (a) contacting a first concentration of a compound with a first host cell containing a first nucleic acid construct which comprises a first minigene, wherein the first minigene comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a first reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first codon of the coding sequence of the first reporter gene and the first start codon of the nucleic acid residues of exon 6 of SMN or a fragment thereof of the first minigene are in the same open reading frame; (b) detecting the activity or amount of a first fusion protein encoded by the first minigene; and (c) comparing the activity or amount of the first fusion protein with the activity or amount of a second fusion protein expressed by a second host cell contacted with a second concentration of the compound, wherein the first and second concentrations of the compound are equivalent, and wherein the second host cell contains a second nucleic acid construct comprising a second minigene encoding the second fusion protein which comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a second reporter gene lacking a start codon, wherein a single guanine residue is inserted after nucleic acid residue 48 of exon 7 of SMN2, and wherein the first codon of the coding sequence of the second reporter gene and the first start codon of the nucleic acid residues of exon 6 of SMN or a fragment thereof of the second minigene are in the same open reading frame; wherein a compound that increases the inclusion of exon 7 of SMN2 into mRNA transcribed from the SMN2 gene is identified and/or validated if the activity or amount of the first fusion protein expressed by the first host cell is increased in the presence of the compound relative to the activity or amount of the first fusion protein expressed by the first host cell in the absence of the compound or the presence of a negative control (e.g., PBS or DMSO), or relative to a previously determined reference range, and the activity or amount of the second fusion protein expressed by the second host cell is not significantly altered in the presence of the compound relative to the absence of the compound or the presence of a negative control (e.g., PBS or DMSO), or relative to a previously determined reference range.

In another embodiment, an assay of the present invention includes a method for the identification and/or validation of a compound that increases the inclusion of exon 7 of SMN2 into mRNA transcribed from the SMN2 gene comprising the steps of: (a) contacting a first concentration of a compound with a first host cell containing a first nucleic acid construct which comprises a first minigene, wherein the first minigene comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a first reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first codon of the coding sequence of the first reporter gene and the first start codon of the first minigene are in the same open reading frame; (b) detecting the activity or amount of a first fusion protein encoded by the first minigene; and (c) comparing the activity or amount of the first fusion protein with the activity or amount of a second fusion protein expressed by a second host cell contacted with a second concentration of the compound, wherein the first and second concentrations of the compound are equivalent, and wherein the second host cell contains a second nucleic acid construct comprising a second minigene encoding the second fusion protein which comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a second reporter gene lacking a start codon, wherein a single guanine residue is inserted after nucleic acid residue 48 of the nucleic acid residues of exon 7 of SMN2, and wherein the first codon of the coding sequence of the second reporter gene and the first start codon of the second minigene are in the same open reading frame; wherein a compound that increases the inclusion of exon 7 of SMN2 into mRNA transcribed from the SMN2 gene is identified and/or validated if the activity or amount of the first fusion protein expressed by the first host cell is increased in the presence of the compound relative to the activity or amount of the first fusion protein expressed by the first host cell in the absence of the compound or the presence of a negative control (e.g., PBS or DMSO), or relative to a previously determined reference range, and the activity or amount of the second fusion protein expressed by the second host cell is not significantly altered in the presence of the compound relative to the absence of the compound or the presence of a negative control (e.g., PBS or DMSO), or relative to a previously determined reference range.

In another embodiment, an assay of the present invention includes a method for the identification and/or validation of a compound that increases the inclusion of exon 7 of SMN2 into mRNA transcribed from the SMN2 gene comprising the steps of: (a) contacting a first concentration of a compound with a first host cell containing a first nucleic acid construct which comprises a first minigene, wherein the first minigene comprises, in 5' to 3' order: nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a first reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first amino acid sequence include a start codon; (iii) the nucleic acid residues encoding the first and second amino acid sequences permit removal of an intron via mRNA splicing, and (iv) the first codon of the coding sequence of the first reporter gene and the first start codon of the first amino acid sequence are in the same open reading frame; (b) detecting the activity or amount of a first fusion protein encoded by the first minigene; and (c) comparing the activity or amount of the first fusion protein with the activity or amount of a second fusion protein expressed by a second host cell contacted with a second concentration of the compound, wherein the first and second concentrations of the compound are equivalent, and wherein second host cell contains a second nucleic acid construct comprising a second minigene encoding the second fusion protein which comprises, in 5' to 3' order: nucleic acid residues encoding a third amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a fourth amino acid sequence, and the nucleic acid residues of the coding sequence of a second reporter gene lacking a start codon, wherein (i) a single guanine residue is inserted after nucleic acid residue 48 of the nucleic acid residues of exon 7 of SMN2; (ii) the nucleic acid residues encoding the third amino acid sequence include a start codon; (iii) the nucleic acid residues encoding the third and fourth amino acid sequences permit removal of an intron via mRNA splicing, and (iv) the first codon of the coding sequence of the second reporter gene and the first start codon of the third amino acid sequence are in the same open reading frame; wherein a compound that increases the inclusion of exon 7 of SMN2 into mRNA transcribed from the SMN2 gene is identified and/or validated if the activity or amount of the first fusion protein expressed by the first host cell is increased in the presence of the compound relative to the activity or amount of the first fusion protein expressed by the first host cell in the absence of the compound or the presence of a negative control (e.g., PBS or DMSO), or relative to a previously determined reference range, and the activity or amount of the second fusion protein expressed by the second host cell is not significantly altered in the presence of the compound relative to the absence of the compound or the presence of a negative control (e.g., PBS or DMSO), or relative to a previously determined reference range.

In another embodiment, an assay of the present invention includes a method for the identification and/or validation of a compound that increases the inclusion of exon 7 of SMN2 into mRNA transcribed from the SMN2 gene comprising the steps of: (a) contacting a first concentration of a compound with a first host cell containing a first nucleic acid construct which comprises a first minigene, wherein the first minigene comprises, in 5' to 3' order: a start codon, nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a first reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first and second amino acid sequences permit removal of an intron via mRNA splicing, and (iii) the first codon of the coding sequence of the first reporter gene and the first start codon of the first minigene are in the same open reading frame; (b) detecting the activity or amount of a first fusion protein encoded by the first minigene; and (c) comparing the activity or amount of the first fusion protein with the activity or amount of a second fusion protein expressed by a second host cell contacted with a second concentration of the compound, wherein the first and second concentrations of the compound are equivalent, and wherein the second host cell contains a second nucleic acid construct comprising a second minigene encoding the second fusion protein which comprises, in 5' to 3' order: a start codon, nucleic acid residues encoding a third amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a fourth amino acid sequence, and the nucleic acid residues of the coding sequence of a second reporter gene lacking a start codon, wherein (i) a single guanine residue is inserted after nucleic acid residue 48 of the nucleic acid residues of exon 7 of SMN2; (ii) the nucleic acid residues encoding the third and fourth amino acid sequences permit removal of an intron via mRNA splicing, and (iii) the first codon of the coding sequence of the second reporter gene and the start codon of the second minigene are in the same open reading frame; wherein a compound that increases the inclusion of exon 7 of SMN2 into mRNA transcribed from the SMN2 gene is identified and/or validated if the activity or amount of the first fusion protein expressed by the first host cell is increased in the presence of the compound relative to the activity or amount of the first fusion protein expressed by the first host cell in the absence of the compound or the presence of a negative control (e.g., PBS or DMSO), or relative to a previously determined reference range, and the activity or amount of the second fusion protein expressed by the second host cell is not significantly altered in the presence of the compound relative to the absence of the compound or the presence of a negative control (e.g., PBS or DMSO), or relative to a previously determined reference range.

In some embodiments, in addition to, or as an alternative to, detecting the activity of the first and second fusion proteins, the amount of the first and second fusion proteins can be detected. In accordance with such embodiments, a compound that enhances the inclusion of exon 7 of SMN2 into mRNA transcribed from the SMN2 gene is identified and validated if: (i) the amount of the first fusion protein expressed by the first host cell is increased in the presence of the compound relative to the activity of the first fusion protein expressed by the first host cell in the absence of the compound or the presence of a negative control (e.g., PBS or DMSO), or relative to a previously determined reference range; and (ii) the amount of the second fusion protein expressed by the second host cell is not significantly altered in the presence of the compound relative to the activity of the second fusion protein expressed by the second host cell in the absence of the compound or the presence of a negative control (e.g., PBS or DMSO), or relative to a previously determined reference range.

In some embodiments, in addition to, or as an alternative to, detecting the amount and/or activity of the first and second fusion proteins, the amount of mRNA transcribed from the first and second minigenes can be detected. In accordance with such embodiments, a compound that increases the inclusion of exon 7 of SMN2 into mRNA transcribed from the SMN2 gene is identified and validated if: (i) the amount of mRNA containing exon 7 of SMN2 transcribed from the first minigene is increased in the presence of a compound relative to the amount of mRNA containing exon 7 of SMN2 transcribed from the first minigene in the absence of the compound or the presence of a negative control (e.g., PBS or DMSO), or relative to a previously determined reference range; and (ii) the amount of the mRNA containing exon 7 of SMN2 transcribed from the second minigene is not significantly altered in the presence of the compound relative to the amount of mRNA containing exon 7 of SMN2 transcribed from the second minigene in the absence of the compound or the presence of a negative control (e.g., PBS or DMSO), or relative to a previously determined reference range.

In these and other embodiments, the terms "not significantly altered" and "not significantly alter" refer to a difference in values for a measurement (e.g., the amount and/or activity of a fusion protein encoded by a minigene described herein) taken of replicate wells of a sample under the same conditions with the exception of one variable (such as the addition of a compound), which difference is not statistically significant. For example, the difference in the amount and/or activity of a fusion protein encoded by a nucleic acid construct as described herein in the presence of a compound relative to the absence of the compound under otherwise the same conditions is not statistically significant. Further, e.g., the difference in the amount of mRNA containing exon 7 of SMN2 transcribed from a minigene described herein in the presence of a compound relative to the absence of the compound under otherwise the same conditions is not statistically significant. In a specific embodiment, a difference is not statistically significant if the p-value is greater 0.01, 0.05, 0.1, or 0.001.

In another embodiment, an assay of the present invention includes a method for the identification and/or validation of a compound that increases the inclusion of exon 7 of SMN2 into mRNA transcribed from the SMN2 gene comprising the steps of: (a) contacting a compound with a host cell containing: (i) a first nucleic acid construct comprising a first minigene which comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a first reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; and (ii) a second nucleic acid construct comprising a second minigene which comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, and a fragment of exon 8 of SMN, and the nucleic acid residues of the coding sequence of a second reporter gene lacking a start codon, wherein (i) a single guanine residue is inserted after nucleic acid residue 48 of exon 7 of SMN2, and (ii) the second reporter gene is different than the first reporter gene; (b) detecting the activity or amount of a first fusion protein encoded by the first minigene and the activity or amount of a second fusion protein encoded by the second minigene; and (c) comparing the activity or amount of the first fusion protein with the activity or amount of the second fusion protein; wherein a compound that increases the inclusion of exon 7 of SMN2 into mRNA transcribed from the SMN2 gene is identified and/or validated if the activity or amount of the first fusion protein expressed by the host cell is increased in the presence of the compound relative to the activity or amount of the first fusion protein expressed by the host cell in the absence of the compound or the presence of a negative control (e.g., PBS or DMSO), or relative to a previously determined reference range, and the activity or amount of the second fusion protein expressed by the host cell is not significantly altered in the presence of the compound relative to the absence of the compound or the presence of a negative control (e.g., PBS or DMSO), or relative to a previously determined reference range. In one aspect, the first and second minigenes each comprise a start codon 5' to the nucleic acid residues of exon 6 of SMN, wherein the first codon of the coding sequence of the first reporter gene and the start codon of the first minigene are in the same open reading frame, and wherein the first codon of the coding sequence of the second reporter gene and the start codon of the second minigene are in the same open reading frame.

In another embodiment, an assay of the present invention includes a method for the identification and/or validation of a compound that increases the inclusion of exon 7 of SMN2 into mRNA transcribed from the SMN2 gene comprising the steps of: (a) contacting a compound with a host cell containing: (i) a first nucleic acid construct comprising a first minigene which comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a first reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first codon of the coding sequence of the first reporter gene and the first start codon of the nucleic acid residues of exon 6 of SMN or a fragment thereof of the first minigene are in the same open reading frame; and (ii) a second nucleic acid construct comprising a second minigene which comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a second reporter gene lacking a start codon, wherein a single guanine residue is inserted after nucleic acid residue 48 of the nucleic acid residues of exon 7 of SMN2, and wherein the first codon of the coding sequence of the second reporter gene and the first start codon of the nucleic acid residues of exon 6 of SMN or a fragment thereof of the second minigene are in the same open reading frame; (b) detecting the activity or amount of a first fusion protein encoded by the first minigene and the activity or amount of a second fusion protein encoded by the second minigene; and (c) comparing the activity or amount of the first fusion protein with the activity or amount of the second fusion protein; wherein a compound that increases the inclusion of exon 7 of SMN2 into mRNA transcribed from the SMN2 gene is identified and/or validated if the activity or amount of the first fusion protein expressed by the host cell is increased in the presence of the compound relative to the activity or amount of the first fusion protein expressed by the host cell in the absence of the compound or the presence of a negative control (e.g., PBS or DMSO), or relative to a previously determined reference range, and the activity or amount of the second fusion protein expressed by the host cell is not significantly altered in the presence of the compound relative to the absence of the compound or the presence of a negative control (e.g., PBS or DMSO), or relative to a previously determined reference range.

In another embodiment, an assay of the present invention includes a method for the identification and/or validation of a compound that increases the inclusion of exon 7 of SMN2 into mRNA transcribed from the SMN2 gene comprising the steps of: (a) contacting a compound with a host cell containing: (i) a first nucleic acid construct comprising a first minigene which comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a first reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first codon of the coding sequence of the first reporter gene and the first start codon of the first minigene are in the same open reading frame; and (ii) a second nucleic acid construct comprising a second minigene which comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a second reporter gene lacking a start codon, wherein a single guanine residue is inserted after nucleic acid residue 48 of the nucleic acid residues of exon 7 of SMN2, and wherein the first codon of the coding sequence of the second reporter gene and the first start codon of the second minigene are in the same open reading frame; (b) detecting the activity or amount of a first fusion protein encoded by the first minigene and the activity or amount of a second fusion protein encoded by the second minigene; and (c) comparing the activity or amount of the first fusion protein with the activity or amount of the second fusion protein; wherein a compound that increases the inclusion of exon 7 of SMN2 into mRNA transcribed from the SMN2 gene is identified and/or validated if the activity or amount of the first fusion protein expressed by the host cell is increased in the presence of the compound relative to the activity or amount of the first fusion protein expressed by the host cell in the absence of the compound or the presence of a negative control (e.g., PBS or DMSO), or relative to a previously determined reference range, and the activity or amount of the second fusion protein expressed by the host cell is not significantly altered in the presence of the compound relative to the absence of the compound or the presence of a negative control (e.g., PBS or DMSO), or relative to a previously determined reference range.

In another embodiment, an assay of the present invention includes a method for the identification and/or validation of a compound that increases the inclusion of exon 7 of SMN2 into mRNA transcribed from the SMN2 gene comprising the steps of: (a) contacting a compound with a host cell containing: (1) a first nucleic acid construct comprising a first minigene which comprises, in 5' to 3' order: nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a first reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first amino acid sequence includes a start codon; (iii) the nucleic acid residues encoding the first and second amino acid sequences permit removal of an intron via mRNA splicing, and (iv) the first codon of the coding sequence of the first reporter gene and the first start codon of the first amino acid sequence are in the same open reading frame; and (2) a second nucleic acid construct comprising a second minigene which comprises, in 5' to 3' order: nucleic acid residues encoding a third amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a fourth amino acid sequence, and the nucleic acid residues of the coding sequence of a second reporter gene lacking a start codon, wherein (i) a single guanine residue is inserted after nucleic acid residue 48 of the nucleic acid residues of exon 7 of SMN2; (ii) the nucleic acid residues encoding the third amino acid sequence include a start codon, (iii) the nucleic acid residues encoding the third and fourth amino acid sequences permit removal of an intron via mRNA splicing, (iv) the first codon of the coding sequence of the second reporter gene and the first start codon of the third amino acid sequence are in the same open reading frame, and (v) the second reporter gene is different than the first reporter gene; (b) detecting the activity or amount of a first fusion protein encoded by the first minigene and the activity or amount of a second fusion protein encoded by the second minigene; and (c) comparing the activity or amount of the first fusion protein with the activity or amount of the second fusion protein; wherein a compound that increases the inclusion of exon 7 of SMN2 into mRNA transcribed from the SMN2 gene is identified and/or validated if the activity or amount of the first fusion protein expressed by the host cell is increased in the presence of the compound relative to the activity or amount of the first fusion protein expressed by the host cell in the absence of the compound or the presence of a negative control (e.g., PBS or DMSO), or relative to a previously determined reference range, and the activity or amount of the second fusion protein expressed by the host cell is not significantly altered in the presence of the compound relative to the absence of the compound or the presence of a negative control (e.g., PBS or DMSO), or relative to a previously determined reference range. In one aspect, the first minigene comprises a start codon 5' to the nucleic acid residues encoding a first amino acid sequence and the second minigene comprises a start codon 5' to the nucleic acid residues encoding a third amino acid sequence, wherein the first codon of the coding sequence of the first reporter gene and the start codon of the first minigene are in the same open reading frame, and wherein the first codon of the coding sequence of the second reporter gene and the start codon of the second minigene are in the same open reading frame.

In another embodiment, an assay of the present invention includes a method for the identification and/or validation of a compound that increases the inclusion of exon 7 of SMN2 into mRNA transcribed from the SMN2 gene comprising the steps of: (a) contacting a compound with a host cell containing: (1) a first nucleic acid construct comprising a first minigene which comprises, in 5' to 3' order: a start codon, nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a first reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first and second amino acid sequences permit removal of an intron via mRNA splicing, and (iii) the first codon of the coding sequence of the first reporter gene and the first start codon of the first minigene are in the same open reading frame; and (2) a second nucleic acid construct comprising a second minigene which comprises, in 5' to 3' order: a start codon, nucleic acid residues encoding a third amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a fourth amino acid sequence, and the nucleic acid residues of the coding sequence of a second reporter gene lacking a start codon, wherein (i) a single guanine residue is inserted after nucleic acid residue 48 of the nucleic acid residues of exon 7 of SMN2; (ii) the nucleic acid residues encoding the third and fourth amino acid sequences permit removal of an intron via mRNA splicing, (iii) the first codon of the coding sequence of the second reporter gene and the first start codon of the second minigene are in the same open reading frame, and (iv) the second reporter gene is different than the first reporter gene; (b) detecting the activity or amount of a first fusion protein encoded by the first minigene and the activity or amount of a second fusion protein encoded by the second minigene; and (c) comparing the activity or amount of the first fusion protein with the activity or amount of the second fusion protein; wherein a compound that increases the inclusion of exon 7 of SMN2 into mRNA transcribed from the SMN2 gene is identified and/or validated if the activity or amount of the first fusion protein expressed by the host cell is increased in the presence of the compound relative to the activity or amount of the first fusion protein expressed by the host cell in the absence of the compound or the presence of a negative control (e.g., PBS or DMSO), or relative to a previously determined reference range, and the activity or amount of the second fusion protein expressed by the host cell is not significantly altered in the presence of the compound relative to the absence of the compound or the presence of a negative control (e.g., PBS or DMSO), or relative to a previously determined reference range.

In some embodiments, in addition to, or as an alternative to, detecting the activity of the first and second fusion proteins, the amount of the first and second proteins encoded by the first and second nucleic acid constructs, respectively, can be detected. In accordance with such embodiments, a compound that enhances the inclusion of exon 7 of the SMN2 into mRMA transcribed from the SMN2 gene is identified and/or validated if: (i) the amount of the first fusion protein expressed by the host cell is increased in the presence of the compound relative to the amount of the first fusion protein expressed by the host cell in the absence of the compound or the presence of a negative control (e.g., PBS or DMSO), or relative to a previously determined reference range; and (ii) the amount of the second fusion protein expressed by the host cell is not significantly altered in the presence of the compound relative to the amount of the second fusion protein expressed by the host cell in the absence of the compound or the presence of a negative control (e.g., PBS or DMSO), or relative to a previously determined reference range.

In some embodiments, in addition to, or as an alternative to, detecting the amount and/or activity of the first and second fusion proteins, the amount of mRNA containing exon 7 of SMN2 transcribed from each of the first and second minigenes can be detected. In accordance with such embodiments, a compound that enhances the inclusion of exon 7 of SMN2 into mRNA transcribed from the SMN2 gene is identified and validated if: (i) the amount of mRNA containing exon 7 of SMN2 transcribed from the first minigene is increased in the presence the compound relative to the amount of mRNA containing exon 7 of SMN2 transcribed from the first minigene in the absence of the compound or the presence of a negative control (e.g., PBS or DMSO), or relative to a previously determined reference range; and (ii) the amount of mRNA containing exon 7 of SMN2 transcribed from the second minigene is not significantly altered in the presence of the compound relative to the amount of mRNA containing exon 7 of SMN2 transcribed from the second minigene in the absence of the compound or the presence of a negative control (e.g., PBS or DMSO), or relative to a previously determined reference range.

In addition to cell-based assays, cell-free assays maybe used to identify or validate compounds that enhance the inclusion of exon 7 of SMN2 into mRNA transcribed from the SMN2 gene.

In one embodiment, an assay of the present invention includes a method for the identification of a compound that increases the inclusion of exon 7 of SMN2 into mRNA transcribed from the SMN2 gene comprising the steps of: (a) contacting a compound with a composition comprising a cell-free extract and a pre-mRNA transcript encoded by a minigene of a nucleic acid construct or a nucleic acid construct comprising a minigene, wherein the minigene comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2. In one aspect, the minigene comprises a start codon 5' to the nucleic acid residues of exon 6 of SMN, wherein the first codon of the coding sequence of the reporter gene and the start codon of the minigene are in the same open reading frame; and (b) detecting the activity or amount of a fusion protein encoded by the minigene, wherein an increase in the activity or amount of the fusion protein expressed by the host cell in the presence of the compound relative to the activity or amount of the fusion protein expressed by the host cell in the absence of the compound or the presence of a negative control compound, or relative to a previously determined reference range indicates that the compound that increases the inclusion of exon 7 of SMN2 into mRNA transcribed from the SMN2 gene.

In another embodiment, an assay of the present invention includes a method for the identification of a compound that increases the inclusion of exon 7 of SMN2 into mRNA transcribed from the SMN2 gene comprising the steps of: (a) contacting a compound with a composition comprising a cell-free extract and a pre-mRNA transcript encoded by a minigene of a nucleic acid construct or a nucleic acid construct comprising a minigene, wherein the minigene comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first start codon of the fragment of the nucleic acid residues of exon 6 of SMN and the first codon of the coding sequence of the reporter gene are in the same open reading frame; and (b) detecting the activity or amount of a fusion protein encoded by the minigene, wherein an increase in the activity or amount of the fusion protein expressed by the host cell in the presence of the compound relative to the activity or amount of the fusion protein expressed by the host cell in the absence of the compound or the presence of a negative control compound, or relative to a previously determined reference range indicates that the compound that increases the inclusion of exon 7 of SMN2 into mRNA transcribed from the SMN2 gene.

In another embodiment, an assay of the present invention includes a method for the identification of a compound that increases the inclusion of exon 7 of SMN2 into mRNA transcribed from the SMN2 gene comprising the steps of: (a) contacting a compound with a composition comprising a cell-free extract and a pre-mRNA transcript encoded by a minigene of a nucleic acid construct or a nucleic acid construct comprising a minigene, wherein the minigene comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first codon of the coding sequence of the reporter gene and the first start codon of the minigene are in the same open reading frame; and (b) detecting the activity or amount of a fusion protein encoded by the minigene, wherein an increase in the activity or amount of the fusion protein expressed by the host cell in the presence of the compound relative to the activity or amount of the fusion protein expressed by the host cell in the absence of the compound or the presence of a negative control compound, or relative to a previously determined reference range indicates that the compound that increases the inclusion of exon 7 of SMN2 into mRNA transcribed from the SMN2 gene.

In another embodiment, an assay of the present invention includes a method for the identification of a compound that increases the inclusion of exon 7 of SMN2 into mRNA transcribed from the SMN2 gene comprising the steps of: (a) contacting a compound with a composition comprising a cell-free extract and a pre-mRNA transcript encoded by a minigene of a nucleic acid construct or a nucleic acid construct comprising a minigene, wherein the minigene comprises, in 5' to 3' order: nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first amino acid sequence include a start codon; (iii) the nucleic acid residues encoding the first and second amino acid sequences permit removal of an intron via mRNA splicing, and (iv) the first codon of the coding sequence of the reporter gene and the start codon of the nucleic acid residues encoding the first amino acid sequence are in the same open reading frame; and (b) detecting the activity or amount of a fusion protein encoded by the minigene, wherein an increase in the activity or amount of the fusion protein expressed by the host cell in the presence of the compound relative to the activity or amount of the fusion protein expressed by the host cell in the absence of the compound or the presence of a negative control compound, or relative to a previously determined reference range indicates that the compound that increases the inclusion of exon 7 of SMN2 into mRNA transcribed from the SMN2 gene.

In another embodiment, an assay of the present invention includes a method for the identification of a compound that increases the inclusion of exon 7 of SMN2 into mRNA transcribed from the SMN2 gene comprising the steps of: (a) contacting a compound with a composition comprising a cell-free extract and a pre-mRNA transcript encoded by a minigene of a nucleic acid construct or a nucleic acid construct comprising a minigene, wherein the minigene comprises, in 5' to 3' order: a start codon, nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first and second amino acid sequences permit removal of an intron via mRNA splicing, and (iii) the first codon of the coding sequence of the reporter gene and the first start codon of the minigene are in the same open reading frame; and (b) detecting the activity or amount of a fusion protein encoded by the minigene, wherein an increase in the activity or amount of the fusion protein expressed by the host cell in the presence of the compound relative to the activity or amount of the fusion protein expressed by the host cell in the absence of the compound or the presence of a negative control compound, or relative to a previously determined reference range indicates that the compound that increases the inclusion of exon 7 of SMN2 into mRNA transcribed from the SMN2 gene.

The present invention provides methods for modulating the inclusion of exon 7 into mRNA transcribed from the SMN2 gene, comprising contacting a human cell with a compound that modulates the expression of a minigene of the invention in a cell-based or cell-free assay described herein. In a specific embodiment, the invention provides a method for enhancing the inclusion of exon 7 of SMN2 into mRNA transcribed from the SMN2 gene, comprising contacting a human cell with a compound that enhances the expression of a minigene of the invention in a cell-based or cell-free assay described herein. In some embodiments, the compound is contacted with the human cell in vitro. In other embodiments, the compound is contacted with the human cell in a non-human animal. In one embodiment, the compound is a compound of Formula (I) or a form thereof.

The present invention provides methods for modulating the inclusion of exon 7 into mRNA transcribed from the SMN2 gene, comprising administering to a non-human animal model for SMA a compound that modulates the expression of a minigene of the invention in a cell-based or cell-free assay described herein. In a specific embodiment, the invention provides a method for enhancing the inclusion of exon 7 of SMN2 into mRNA transcribed from the SMN2 gene, comprising administering to a non-human animal model for SMA a compound that enhances the expression of a minigene of the invention in a cell-based or cell-free assay described herein. In one embodiment, the compound is a compound of Formula (I) or a form thereof.

The present invention provides methods for increasing the amount of SMN protein, comprising contacting a human cell with a compound that enhances the inclusion of exon 7 of SMN2 into mRNA transcribed from the SMN2 gene. In some embodiments, the human cell is contacted with the compound in vitro. In other embodiments, the human cell is contacted with the compound in a non-human animal. In one embodiment, the compound is a compound of Formula (I) or a form thereof.

The present invention provides methods for increasing the amount of SMN protein, comprising administering to a non-human animal model for SMA a compound that enhances the inclusion of exon 7 of SMN2 into mRNA transcribed from the SMN2 gene as assessed in a cell-based or cell-free assay described herein. In one embodiment, the compound is a compound of Formula (I) or a form thereof.

Compounds that enhance the inclusion of exon 7 of SMN2 into mRNA transcribed from the SMN2 gene are beneficial to patients with SMA. In some embodiments, fewer side effects and increased efficacy are expected from the administration of such compounds because the activity of such compounds is expected to be limited to interaction with SMN2 pre-mRNA in specific combination with the splicing regulatory elements found in exon 7 of SMN2 and intron 7 of SMN. In some embodiments, compounds that enhance the inclusion of exon 7 of SMN2 into mRNA transcribed from the SMN2 gene may also be used in combination with additional agents that specifically enhance the expression of SMN, potentially allowing for a lower dose of both the compound being used to enhance SMN expression and the agent, thereby reducing side effects. Compounds that enhance the inclusion of exon 7 of SMN2 into mRNA transcribed from the SMN2 gene, and thus, increase levels of the SMN protein, when used therapeutically, may increase SMN protein levels in SMA patients and protect motor neurons from degeneration.

Thus, the invention provides a method for increasing expression of SMN in a human subject in need thereof, comprising administering to the human subject an effective amount of a compound that enhances the inclusion of exon 7 of SMN2 into mRNA transcribed from the SMN2 gene.

In one embodiment, the invention provides a method for enhancing expression of SMN in a human subject in need thereof, comprising administering to the human subject an effective amount of a compound, wherein the compound enhances, in vitro or in cultured cells, the amount and/or activity of a fusion protein encoded by a nucleic acid construct comprising a minigene as described herein.

The invention also provides for the use of a compound for the preparation of a medicament that enhances the inclusion of exon 7 of SMN2 into mRNA transcribed from the SMN2 gene, thereby increasing expression of SMN in a human subject in need thereof.

The invention also provides for the use of a compound for the preparation of a medicament that enhances expression of SMN in a human subject in need thereof wherein the compound enhances, in vitro or in cultured cells, the amount and/or activity of a fusion protein encoded by a nucleic acid construct comprising a minigene as described herein.

The invention also provides a method for enhancing the expression of SMN in a human subject in need thereof, comprising administering to the human subject an effective amount of a pharmaceutical composition comprising a compound that enhances the inclusion of exon 7 of SMN2 into mRNA transcribed from the SMN2 gene, and a pharmaceutically acceptable carrier, excipient or diluent.

The present invention further provides a method for treating SMA in a human subject in need thereof, comprising administering to the human subject an effective amount of a compound that enhances the inclusion of exon 7 of SMN2 into mRNA transcribed from the SMN2 gene.

In one embodiment, the invention provides a method for treating SMA in a human subject in need thereof, comprising administering to the human subject an effective amount of a compound, wherein the compound enhances, in vitro or in cultured cells, the amount and/or activity of a fusion protein encoded by a nucleic acid construct comprising a minigene as described herein.

The invention also provides for the use of a compound for the preparation of a medicament that enhances the inclusion of exon 7 of SMN2 into mRNA transcribed from the SMN2 gene, thereby treating SMA in a human subject in need thereof.

The invention also provides for the use of a compound for the preparation of a medicament for the treatment of SMA in a human subject in need thereof, wherein the compound enhances, in vitro or in cultured cells, the amount and/or activity of a fusion protein encoded by a nucleic acid construct comprising a minigene as described herein.

The invention also provides a method for the treatment of SMA in a human subject in need thereof, comprising administering to the human subject an effective amount of a pharmaceutical composition comprising a compound that enhances the inclusion of exon 7 of SMN2 into mRNA transcribed from the SMN2 gene, and a pharmaceutically acceptable carrier, excipient or diluent.

In one embodiment, treatment results in the ability or helps retain the ability for a human infant or a human toddler to sit up. In another embodiment, treatment results in the ability or helps retain the ability for a human infant, a human toddler, a human child or a human adult to stand up unaided. In another embodiment, treatment results in the ability or helps retain the ability for a human infant, a human toddler, a human child or a human adult to walk unaided.

Compounds of Formula (I) have been shown to enhance the inclusion of exon 7 of SMN2 into mRNA transcribed from the SMN2 gene using the assays described herein. Accordingly, compounds of Formula (I) have utility as enhancers for the inclusion of exon 7 of SMN2 into mRNA transcribed from the SMN2 gene.

The compounds of Formula (I) identified for use in the present invention have been disclosed as compounds that suppress premature translation termination associated with mRNA nonsense mutations in International Application PCT/US05/036762 filed Oct. 13, 2005 (published as WO2006/044503) and for use in a method of producing a functional readthrough protein in International Application PCT/US07/008,268 filed Mar. 29, 2007 (published as WO2007/117438), each of which are incorporated herein in their entirety and for all purposes.

In an embodiment of the present invention, a method for enhancing expression of SMN in a human subject in need thereof, comprises administering to the human subject an effective amount of a compound of Formula (I) or a form thereof that enhances the inclusion of exon 7 of SMN2 into mRNA transcribed from the SMN2 gene.

In another embodiment of the present invention, a method for treating SMA in a human subject in need thereof, comprises administering to the human subject an effective amount of a compound of Formula (I) or a form thereof that enhances the inclusion of exon 7 of SMN2 into mRNA transcribed from the SMN2 gene.

In an embodiment of one or more methods of the present invention, the compound is a compound of Formula (I):

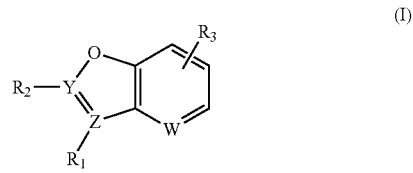

or a form thereof, wherein:
Y and Z are each independently selected from N or C, wherein Y and Z are each not simultaneously N or C;
W is N or C;
$R_1$ is selected from hydrogen or aryl, wherein aryl is optionally substituted with carboxyl and, wherein $R_1$ is absent when Z is N;
$R_2$ is selected from hydrogen, $C_{3-14}$cycloalkyl, aryl, heteroaryl or heterocyclyl,
wherein aryl is optionally substituted with one, two, or three substituents each selected from halogen, carboxyl, $C_{1-6}$alkyl, $C_{1-6}$alkoxy, halo-$C_{1-6}$alkoxy, $C_{1-6}$alkoxy-carbonyl, amino or $C_{1-6}$alkyl-amino, or one substituent selected from halo-$C_{1-6}$alkyl-amino, hydroxy-$C_{1-6}$alkyl-amino, amino-carbonyl, $C_{1-6}$alkyl-amino-carbonyl, aryl, heteroaryl or heterocyclyl, optionally substituted on heterocyclyl with one or two oxo substituents,
wherein heteroaryl is optionally substituted with one or two $C_{1-6}$alkyl substituents or one heterocyclyl substituent,
wherein heterocyclyl is optionally substituted with one or two substituents each selected from halogen or $C_{1-6}$alkyl, and
wherein $R_2$ is absent when Y is N; and
$R_3$ is one, two, or three carbon atom substituents each selected from hydrogen, halogen, carboxyl, $C_{1-6}$alkyl, $C_{1-6}$alkoxy, amino, amino-$C_{1-6}$alkyl, $C_{1-6}$alkyl-carbonyl-amino, $C_{3-14}$cycloalkyl, $C_{3-14}$cycloalkyloxy, $C_{3-14}$cycloalkyl-$C_{1-6}$alkyl, aryl, aryloxy, aryloxy-$C_{1-6}$alkyl, heteroaryl, heteroaryl-$C_{1-6}$alkyl, heterocyclyl, heterocyclyl-$C_{1-6}$alkyl or heterocyclyl-carbonyl,
wherein each instance of amino is optionally substituted with one or two substituents each selected from $C_{1-6}$alkyl, hydroxy-$C_{1-6}$alkyl, carboxy-$C_{1-6}$alkyl, aryl-$C_{1-6}$alkyl, heterocyclyl-$C_{1-6}$alkyl or aryl optionally substituted with one or two $C_{1-6}$alkyl substituents,
wherein each instance of aryl is optionally substituted with one or two substituents each selected from halogen, $C_{1-6}$alkyl, halo-$C_{1-6}$alkyl, $C_{1-6}$alkoxy, halo-$C_{1-6}$alkoxy or aryl optionally substituted with one or two $C_{1-6}$alkyl substituents, and
wherein each instance of heterocyclyl is optionally substituted with one or two substituents each selected from $C_{1-6}$alkyl or aryl optionally substituted with one or two $C_{1-6}$alkyl substituents, or is optionally substituted on one or two carbon atoms with an oxo substituent.

Terminology

As used herein, the term "about" or "approximately" when used in conjunction with a number refers to any number within 1, 5 or 10% of the referenced number.

In certain embodiments, as used herein, the term "compound" refers to any agent having the ability to modulate inclusion of exon 7 of SMN2 into mRNA transcribed from the SMN2 gene and thus modulate the levels of the SMN protein produced from the SMN2 gene, or any agent that has been identified to increase the inclusion of exon 7 of SMN2 into mRNA transcribed from the SMN2 gene and thus, increase the levels of the SMN protein produced from the SMN2 gene, including a compound provided herein or incorporated by reference herein. In one embodiment, the term "compound" refers to a small molecule. In a specific embodiment, the term "compound" refers to a compound of Formula (I) or a form thereof.

As used herein, the term "effective amount" in the context of a method of treating SMA in a human subject, or a method of enhancing/increasing the expression of SMN in a human subject, refers to the amount of a compound which has a therapeutic effect. Non-limiting examples of effective amounts of a compound are described below.

As used herein, the terms "mRNA containing exon 7 of SMN2 or a fragment thereof" or "mRNA transcript containing exon 7 of SMN2 or a fragment thereof," in the context of detecting the amount of mRNA transcribed from a minigene or the SMN2 gene, refers to a mRNA comprising the sequence of exon 7 of SMN2 or a fragment thereof encoded by a minigene or the SMN2 gene. In other words, the complete sequence of exon 7 of SMN2 or the fragment thereof that is encoded by the minigene or SMN2 gene. For example, when a minigene comprises the nucleic acid residues of exon 7 of SMN2, the mRNA transcribed from the minigene will comprise the complete, non-truncated sequence of exon 7 of SMN2. Further, when a minigene comprises a fragment of exon 7 of SMN2, the mRNA transcribed from the minigene will comprise the fragment.

As used herein, the term "elderly human" refers to a human 65 years or older.

As used herein, the term "form" in the context of a compound refers to a compound isolated for use as a pharmaceutically acceptable salt, ester, hydrate, solvate, polymorph, geometric isomer, racemate, enantiomer or tautomer.

As used herein, the term "fragment" in the context of nucleic acid residues of exon 6 of SMN refers to any number of nucleic acids of exon 6 of SMN so long as the fragment retains a minimum number of nucleic acids required for splicing and encodes an amino acid sequence that maintains a start codon and the first codon of the coding sequence of the reporter gene included in a minigene described herein in the same open reading frame. In specific embodiments, the fragment of exon 6 of SMN permits removal of an intron via mRNA splicing and maintains the complete sequence of the mRNA fragment included (or encoded) in a minigene. In a specific embodiment, the fragment includes the intact 3' end of exon 6 of SMN. In another embodiment, the fragment of exon 6 of SMN is at least 9 or at least 12 nucleic acids long. In a specific embodiment, the intact 3' end of the fragment of exon 6 of SMN is at least 9 or at least 12 nucleic acids long. In some embodiments, the fragment has endogenous start codons at nucleotide positions 64, 82 and 109 of exon 6 of SMN. In a specific embodiment, the fragment of exon 6 of SMN is at least 64 nucleic acids long and comprises a start codon (e.g., ATG or a non-canonical start codon) inserted at a nucleotide position before nucleotide position 64 of exon 6 of SMN. In certain embodiments, a fragment of the nucleic acid residues of exon 6 of SMN does not contain a start codon and in those circumstances a start codon is added to the 5' end of SMN minigene, and the start codon and the first codon of the coding sequence of the reporter gene of a minigene described herein are in same open reading frame. In certain embodiments, when a start codon having any number of nucleic acids divisible by three has been added to the 5' end of exon 6 of SMN or inserted at a nucleotide position before position 64, the start codons at nucleotide positions 64, 82 and 109 will be pushed to a nucleotide position corresponding to the number of nucleic acids added. In one embodiment, the first codon of the coding sequence of the reporter gene and the start codon of the minigene are in the same open reading frame. Accordingly, either the added start codon or the endogenous start codons may be used to initiate translation.

As used herein, the term "fragment" in the context of nucleic acid residues of intron 6 and intron 7 of SMN refers to any number of nucleic acids of intron 6 and intron 7 of SMN, respectively, as long as the fragment retains the minimum number of nucleic acids required for a functional intron that permits the retention of the nucleotides of the exons flanking the intron. In one embodiment, the fragment comprises at least six nucleotides of the 5' splice site of intron 6 or intron 7 of SMN and three nucleotides plus the polypyrimidine tract and the branch-point sequence of the 3' splice site of intron 6 or intron 7 of SMN. In one embodiment, the 3' splice site comprises about 40 nucleic acid residues of the 3' splice site of intron 6 or intron 7 of SMN. In another embodiment, the 3' splice site comprises 20 nucleic acid residues of the 3' splice site of intron 6 or intron 7 of SMN.

As used herein, the term "fragment" in the context of nucleic acid residues of exon 7 of SMN2 refers to a fragment of exon 7 of SMN2 in which any number of nucleic acids divisible by three have been removed without generating a frameshift, while maintaining the 5' nucleic acid residues 1 to 12 of exon 7 of SMN2 and the 3' nucleic acid residues 37 to 51 of exon 7 of SMN2. In other words, the fragment of exon 7 of SMN2 permits removal of an intron via mRNA splicing and maintains the complete sequence of the mRNA fragment included (or encoded) in a minigene. Accordingly, the SMN2 minigene may include either the intact exon 7 of SMN2 or a fragment of exon 7 of SMN2 in which any number of nucleic acids between nucleic acids 13 to 36 divisible by three have been removed without generating a frameshift. Within the scope of the present invention, such an intact exon or fragment thereof may be used to identify compounds useful for enhancing the inclusion of exon 7 of SMN2 into mRNA produced from the SMN2 gene.

As used herein, the term "fragment" in the context of nucleic acid residues of exon 7 of SMN1 refers to a fragment of exon 7 of SMN1 in which any number of nucleic acids divisible by three have been removed without generating a frameshift, while maintaining the 5' nucleic acid residues 1 to 12 of exon 7 of SMN1 and the 3' nucleic acid residues 37 to 51 of exon 7 of SMN1. In other words, the fragment of exon 7 of SMN1 permits removal of an intron via mRNA splicing and maintains the complete sequence of the mRNA fragment included (or encoded) in a minigene. Accordingly, the SMN1 minigene may include either the intact exon 7 of SMN1 or a fragment of exon 7 of SMN1 in which any number of nucleic acids between nucleic acids 13 to 36 divisible by three have been removed without generating a frameshift.

As used herein, the term "fragment" in the context of nucleic acid residues of exon 8 of SMN in the methods described herein for refers to any number of nucleic acids of exon 8 of SMN so long as the fragment encodes an amino acid sequence that maintains a start codon and the first codon of the coding sequence of the reporter gene included in a minigene described herein in the same open reading frame. In specific embodiments, the fragment of exon 8 of SMN permits removal of an intron via mRNA splicing and maintains the complete sequence of the mRNA fragment included (or encoded) in a minigene. In one embodiment, the fragment of exon 8 comprises between 2 to 23 nucleic acid residues from the 5' terminus of exon 8 of SMN. In certain embodiments, the fragment of exon 8 of SMN comprises the first 2, 5, 8, 11, 14, 17, 20 or 23 nucleic acid residues of exon 8 of SMN. In a specific embodiment, the fragment of exon 8 of SMN comprises the first 23 nucleic acid residues of exon 8 of SMN. In another specific embodiment, the fragment of exon 8 of SMN comprises the first 21 nucleic acid residues of exon 8 of SMN. In an alternative embodiment, the fragment of exon 8 of SMN comprises more or fewer than the first 21 nucleic acid residues of exon 8 of SMN. In another embodiment, the fragment of exon 8 of SMN comprises at least 2 nucleic acid residues of exon 8 of SMN.

As used herein, the term "fragment" in the context of nucleic acid residues of exon 8 of SMN in the methods described herein for detecting mRNA transcribed from a minigene refers to any number of nucleic acids of exon 8 of SMN. In a specific embodiment, the fragment comprises at least 2 nucleic acid residues of exon 8 of SMN.

As used herein, the term "host cell" includes a particular subject cell transformed or transfected with an instant nucleic acid construct and the progeny or potential progeny of such a cell. Progeny of such a cell may not be identical to the parent cell transfected with the nucleic acid construct due to mutations or environmental influences that may occur in succeeding generations or integration of the nucleic acid construct into the host cell genome.

As used herein, the term "human adult" refers to a human that is 18 years or older.

As used herein, the term "human child" refers to a human that is 1 year to 18 years old.

As used herein, the term "human infant" refers to a newborn to 1 year old year human.

As used herein, the term "human toddler" refers to a human that is 1 year to 3 years old.

As used herein, the term "inclusion of exon 7 of SMN2 into mRNA transcribed from the SMN2 gene" refers to the inclusion of the complete, intact, non-truncated sequence of exon 7 of SMN2 into the mature mRNA transcribed from the SMN2 gene.

As used herein, the terms "nucleic acid residues encoding a first amino acid sequence," "nucleic acid residues encoding a second amino acid sequence," "nucleic acid residues encoding a third amino acid sequence" and "nucleic acid residues encoding a fourth amino acid sequence," in the context of nucleic acid residues used in place of exon 6 of SMN or a fragment thereof and/or the fragment of exon 8 of SMN, refer to any number of nucleic acids such that each amino acid sequence retains the minimum number and type of nucleic acids required to permit removal of an intron via mRNA splicing and maintain the complete sequence of the nucleic acid encoding the first, second, third, and/or fourth amino acid sequence included in a minigene. Accordingly, the nucleic acid residues encoding the first, second, third, and fourth amino acid sequences can function as exons.

As used herein, the term "isolated," in the context of a compound, means the physical state of a compound after being separated and/or purified from precursors and other substances found in a synthetic process (e.g., from a reaction mixture) or natural source or combination thereof according to a process or processes described herein or which are well known to the skilled artisan (e.g., chromatography, recrystallization and the like) in sufficient purity to be characterizable by standard analytical techniques described herein or well known to the skilled artisan. In a specific embodiment, the compound is at least 60% pure, at least 65% pure, at least 70% pure, at least 75% pure, at least 80% pure, at least 85% pure, at least 90% pure or at least 99% pure as assessed by techniques known to one of skill in the art.

As used herein, the term "isolated," as it refers to a nucleic acid, means the physical state of a nucleic acid after being separated and/or purified from precursors and other substances found in a synthetic process (e.g., from a reaction mixture) or natural source or combination thereof according to a process or processes described herein or which are well known to the skilled artisan in sufficient purity to be capable of characterization by standard analytical techniques described herein or well known to the skilled artisan.

In some embodiments, the terms "nucleic acid" and "nucleotides" refer to deoxyribonucleotides, deoxyribonucleic acids, ribonucleotides, and ribonucleic acids, and polymeric forms thereof, and includes either single- or double-stranded forms. In certain embodiments, such terms include known analogs of natural nucleotides, for example, peptide nucleic acids ("PNA"s), that have similar binding properties as the reference nucleic acid. In some embodiments, nucleic acid refers to deoxyribonucleic acids (e.g., cDNA or DNA). In other embodiments, nucleic acid refers to ribonucleic acid (e.g., mRNA or RNA).

As used herein, the term "nucleic acid residues of exon 6 of SMN," unless otherwise specified herein, refers to a complete, intact, non-truncated nucleic acid sequence of exon 6 of human SMN1 or SMN2. As used herein, the term "nucleic acid residues of exon 6 of SMN1" refers to a complete, intact, non-truncated nucleic acid sequence of exon 6 of human SMN1. As used herein, the term "nucleic acid residues of exon 6 of human SMN2" refers to a complete, intact, non-truncated nucleic acid sequence of exon 6 of human SMN2. In certain embodiments, a minigene described herein comprises, in part, a complete, intact, non-truncated nucleic acid sequence of exon 6 of human SMN1 or SMN2.

As used herein, the term "nucleic acid residues of intron 6 of SMN," unless otherwise specified herein, refers to a complete, intact, non-truncated nucleic acid sequence of intron 6 of human SMN1 or SMN2. As used herein, the term "nucleic acid residues of intron 6 of SMN1" refers to a complete, intact, non-truncated nucleic acid sequence of intron 6 of human SMN1. As used herein, the term "nucleic acid residues of intron 6 of human SMN2" refers to a complete, intact, non-truncated nucleic acid sequence of intron 6 of human SMN2. In certain, embodiments, a minigene described herein comprises, in part, a complete, intact, non-truncated nucleic acid sequence of intron 6 of human SMN1 or SMN2.

As used herein, the term "nucleic acid residues of exon 7 of SMN," unless otherwise specified herein, refers to a complete, intact, non-truncated nucleic acid sequence of exon 7 of human SMN1 or SMN2. As used herein, the term "nucleic acid residues of exon 7 of human SMN1" refers to a complete, intact, non-truncated nucleic acid sequence of exon 7 of human SMN1. As used herein, the term "nucleic acid residues of exon 7 of SMN2" refers to a complete, intact, non-truncated nucleic acid sequence of exon 7 of human SMN2. In certain, embodiments, a minigene described herein comprises, in part, a complete, intact, non-truncated nucleic acid sequence of exon 7 of human SMN1 or SMN2.

As used herein, the term "nucleic acid residues of intron 7 of SMN," unless otherwise specified herein, refers to a complete, intact, non-truncated nucleic acid sequence of intron 7 of human SMN1 or SMN2. As used herein, the term "nucleic acid residues of intron 7 of SMN1" refers to a complete, intact, non-truncated nucleic acid sequence of intron 7 of human SMN1. As used herein, the term "nucleic acid residues of intron 7 of SMN2" refers to a complete, intact, non-truncated nucleic acid sequence of intron 7 of human SMN2. In certain, embodiments, a minigene described herein comprises, in part, a complete, intact, non-truncated nucleic acid sequence of intron 7 of human SMN1 or SMN2.

As used herein, the term "nucleic acid residues of exon 8 of SMN," unless otherwise specified herein, refers to a complete, intact, non-truncated nucleic acid sequence of exon 8 of human SMN1 or SMN2. As used herein, the term "nucleic acid residues of exon 8 of SMN1" refers to a complete, intact, non-truncated nucleic acid sequence of exon 8 of human SMN1. As used herein, the term "nucleic acid residues of exon 8 of SMN2" refers to a complete, intact, non-truncated nucleic acid sequence of exon 8 of human SMN2. In certain, embodiments, a minigene described herein comprises, in part, a complete, intact, non-truncated nucleic acid sequence of exon 8 of human SMN1 or SMN2.

As used herein, the term "ORF" refers to a mRNA open reading frame, i.e., the region of the mRNA that is translated into protein.

As used herein, the term "premature human infant" refers to a human infant born at less than 37 weeks of gestational age.

As used herein, the term "previously determined reference range" in the context of detecting the amount or activity of a protein refers to a reference range for the amount or the activity of a fusion protein encoded by a minigene, or SMN protein translated from an mRNA transcribed from the SMN2 gene. In a specific embodiment, the previously determined reference range is the amount or activity of a fusion protein or SMN protein that is detected when a host cell(s) containing a nucleic acid construct comprising a minigene or the SMN2 gene is contacted with a negative control (e.g., PBS or DMSO). The term "previously determined reference range" in the context of detecting the amount of mRNA transcribed from a minigene or the SMN2 gene refers to a reference range for the amount of an mRNA transcript transcribed from a minigene or the amount of an mRNA transcript transcribed from the SMN2 gene in a particular host cell(s) or in a particular cell-free extract. In a specific embodiment, the previously determined reference range is the amount of mRNA containing exon 7 of SMN2 or a fragment thereof transcribed from a minigene or the amount of mRNA containing exon 7 of SMN2 transcribed from the SMN2 gene in a cell-free extract or a host cell(s) contacted with a negative control (e.g., PBS or DMSO). Ideally, testing laboratories will establish a reference range for each cell type and each cell-free extract in the practice of such assays. In a specific embodiment, at least one positive control or at least one negative control is included for each compound analyzed.

As used herein, the term "small molecule" and analogous terms include, but are not limited to, peptides, peptidomimetics, amino acids, amino acid analogs, polynucleotides, polynucleotide analogs, nucleotides, nucleotide analogs, other organic and inorganic compounds (i.e., including heteroorganic and organometallic compounds) and forms thereof having a molecular weight of less than about 10,000 grams per mole, or less than about 5,000 grams per mole, or less than about 1,000 grams per mole, or less than about 500 grams per mole, or less than about 100 grams per mole.

As used herein, the italicized term "SMN," unless otherwise specified herein, refers to human SMN1 or human SMN2. Nucleic acid sequences for the human SMN1 and SMN2 are known in the art. See, e.g., GenBank Accession Nos. DQ894095, NM_000344, NM_022874, and BC062723 for nucleic acid sequences of human SMN1. For nucleic acid sequences of human SMN2, see, e.g., NM_022875, NM_022876, NM_022877, NM_017411, DQ894734 (Invitrogen, Carlsbad, Calif.), BC000908.2, and BC015308.1.

The SMN1 gene can be found on human chromosome 5 from approximately nucleotide 70,256,524 to approximately nucleotide 70,284,595 using Vega Gene ID: OTTHUMG00000099361 (see website for ensembl.org/Homo_sapiens/geneview?gene=OTTHUMG00000099361; db=vega) at cytogenetics location 5 of 13. See also GenBank Accession No. NC_000005, Build 36.3 for the sequence of human chromosome 5.

The approximate locations of exons 6, 7 and 8 and introns 6 and 7 of SMN1 on human chromosome 5 using Vega gene ID:

OTTHUMG00000099361 (see website for ensembl.org/Homo_sapiens/geneview?gene=OTTHUMG00000099361; db=vega) are as follows:
70,277,649-70,277,759 exon 6
70,277,760-70,283,523 intron 6
70,283,524-70,283,577 exon 7
70,283,578-70,284,021 intron 7
70,284,022-70,284,595 exon 8

In specific embodiments, the nucleotide sequences delineated above for exons 6, 7 and 8 and introns 6 and 7 of SMN1 are used in the nucleic acid constructs described herein. In other specific embodiments, the nucleotide sequences described in the example below for exons 6, 7 and 8 and introns 6 and 7 are used in the nucleic acid constructs described herein.

The SMN2 gene can be found on human chromosome 5 from approximately nucleotide 69,381,106 to approximately nucleotide 69,409,175 using Vega gene ID: OTTHUMG00000099389 (see website for ensembl.org/Homo_sapiens/geneview?gene=OTTHUMG00000099389; db=vega). See also, GenBank Accession No. NC_000005, Build 36.3 for the sequence of human chromosome 5.

The approximate locations of exons 6, 7 and 8 and introns 6 and 7 of SMN2 on human chromosome 5 using Vega gene ID: OTTHUMG00000099389 (see website for ensembl.org/Homo_sapiens/geneview?gene=OTTHUMG00000099389; db=vega) are as follows:
69,402,224-69,402,334 exon 6
69,402,335-69,408,103 intron 6
69,408,104-69,408,157 exon 7
69,408,158-69,408,601 intron 7
69,408,602-69,409,175 exon 8.

In specific embodiments, the nucleotide sequences delineated above for exons 6, 7 and 8 and introns 6 and 7 of SMN2 are used in the nucleic acid constructs described herein. In other specific embodiments, the nucleotide sequences of exons 6, 7 and 8 and introns 6 and 7 of SMN2 shown in FIG. 2 or 3 are used in the nucleic acid constructs described herein.

As used herein, the terms "subject" and "patient" are used interchangeably and refer to a human.

As used herein, the terms "treat," "treatment," and "treating" in the context of administration of a therapy(ies) to a subject in need thereof, to treat SMA or to enhance expression of SMN, refer to a therapeutic effect achieved following the administration of a compound or a combination of compounds. In a specific embodiment, the therapeutic effect is at least one or more of the following effects resulting from the administration of a compound or a combination of compounds: (i) the reduction or amelioration of the severity of SMA and/or a symptom associated therewith; (ii) the reduction in the duration of a symptom associated with SMA; (iii) the prevention in the recurrence of a symptom associated with SMA; (iv) the inhibition in the development or onset of a symptom of SMA; (v) the regression of SMA and/or a symptom associated therewith; (vi) the reduction in the loss of muscle strength; (vii) the increase in muscle strength; (viii) the reduction in muscle atrophy; (ix) the reduction in the loss of motor function; (x) the increase in motor neurons; (xi) the reduction in the loss of motor neurons; (xii) the protection of SMN deficient motor neurons from degeneration; (xiii) the increase in motor function; (xiv) the increase in pulmonary function; (xv) the reduction in the loss of pulmonary function; (xvi) the reduction in hospitalization of a subject; (xvii) the reduction in hospitalization length for a subject; (xviii) the increase in the survival of a subject; (xix) the inhibition of the progression of SMA and/or a symptom associated therewith; (xx) the enhancement or improvement the therapeutic effect of another therapy and/or (xxi) the improvement in the quality of life of a patient. In some embodiments, the therapeutic effect reduces or inhibits the progression of SMA.

As used herein, the terms "validate," "validating," "validated" and "validation" in the context of methods for validating compounds refer to methods for confirming or verifying that compounds identified in a screening assay, such as described herein, enhance the inclusion of exon 7 of SMN2 into mRNA transcribed from the SMN2 gene.

As used herein, the term "$C_{1-6}$alkyl" generally refers to saturated hydrocarbon radicals having from one to six carbon atoms in a straight or branched chain configuration, including methyl, ethyl, n-propyl, isopropyl, n-butyl, isobutyl, sec-butyl, tert-butyl, n-pentyl, n-hexyl and the like. In some embodiments, $C_{1-6}$alkyl includes $C_{1-4}$alkyl and the like. A $C_{1-6}$alkyl radical may be optionally substituted where allowed by available valences.

As used herein, the term "$C_{1-6}$alkoxy" generally refers to saturated hydrocarbon radicals of from one to six carbon atoms having a straight or branched chain configuration of the formula: —O—$C_{1-6}$alkyl, including methoxy, ethoxy, n-propoxy, isopropoxy, n-butoxy, isobutoxy, sec-butoxy, tert-butoxy, n-pentoxy, n-hexoxy and the like. In some embodiments, $C_{1-6}$alkoxy includes $C_{1-4}$alkoxy and the like. A $C_{1-6}$alkoxy radical may be optionally substituted where allowed by available valences.

As used herein, the term "$C_{3-14}$cycloalkyl" generally refers to a saturated or partially unsaturated monocyclic, bicyclic or polycyclic hydrocarbon radical, including cyclopropyl, cyclobutyl, cyclopentyl cyclohexyl, cyclohexenyl, cycloheptyl, cyclooctyl, 1H-indanyl, indenyl, tetrahydro-naphthalenyl and the like. In some embodiments, $C_{3-14}$cycloalkyl includes $C_{3-8}$cycloalkyl, $C_{5-8}$cycloalkyl, $C_{3-10}$cycloalkyl and the like. A $C_{3-14}$cycloalkyl radical may be optionally substituted where allowed by available valences.

As used herein, the term "aryl" generally refers to a monocyclic, bicyclic or polycyclic aromatic carbon atom ring structure radical, including phenyl, naphthyl, anthracenyl, fluorenyl, azulenyl, phenanthrenyl and the like. An aryl radical may be optionally substituted where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including furanyl, thienyl (or thiophenyl), 2H-pyrrolyl, 3H-pyrrolyl, pyrazolyl, imidazolyl, isoxazolyl, isothiazolyl, oxazolyl, thiazolyl, triazolyl (and regioisomers thereof), oxadiazolyl (and regioisomers thereof), thiadiazolyl (and regioisomers thereof), tetrazolyl (and regioisomers thereof), pyranyl, thiopyranyl, pyridinyl, pyrimidinyl, pyrazinyl, pyridazinyl, triazinyl (and regioisomers thereof), indole, indazolyl, isoindolyl, benzofuranyl, benzothienyl, benzimidazolyl, benzoxazolyl, purinyl, quinolinyl, isoquinolinyl, quinazolinyl, quinoxalinyl, 1,3-diazinyl, 1,2-diazinyl, 1,2-diazolyl, 1,4-diazanaphthalenyl, acridinyl and the like. A heteroaryl radical may be optionally substituted where allowed by available valences.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including oxiranyl, oxetanyl, azetidinyl, dihydrofuranyl, tetrahydrofuranyl, dihydrothienyl, tetrahydrothienyl, pyrrolinyl, pyrrolidinyl, dihydropyrazolyl, pyrazolinyl, pyrazolidinyl, dihydroimidazolyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl (and regioisomers thereof), triazolidinyl (and regioisomers thereof), oxadiazolinyl (and regioisomers thereof), oxadiazolidinyl (and regioisomers thereof), thiadiazolinyl (and regioisomers thereof), thiadiazolidinyl (and regioisomers thereof), tetrazolinyl (and regioisomers thereof), tetrazolidinyl (and regioisomers thereof), dihydro-2H-pyranyl, tetrahydro-2H-pyranyl, tetrahydro-thiopyranyl, dihydro-pyridinyl, tetrahydro-pyridinyl, hexahydro-pyridinyl, dihydro-pyrimidinyl, tetrahydro-pyrimidinyl, dihydro-pyrazinyl, tetrahydro-pyrazinyl, dihydro-pyridazinyl, tetrahydro-pyridazinyl, piperazinyl, piperidinyl, morpholinyl, thiomorpholinyl, dihydro-triazinyl (and regioisomers thereof), tetrahydro-triazinyl (and regioisomers thereof), hexahydro-triazinyl (and regioisomers thereof), dihydro-indole, tetrahydro-indole, dihydro-indazolyl, tetrahydro-indazolyl, dihydro-isoindolyl, tetrahydro-isoindolyl, dihydro-benzofuranyl, tetrahydro-benzofuranyl, dihydro-benzothienyl, tetrahydro-benzothienyl, dihydro-benzimidazolyl, tetrahydro-benzimidazolyl, dihydro-benzoxazolyl, tetrahydro-benzoxazolyl, benzo[1,3]dioxolyl, benzo[1,4]dioxanyl, dihydro-purinyl, tetrahydro-purinyl, dihydro-quinolinyl, tetrahydro-quinolinyl, dihydro-isoquinolinyl, tetrahydro-isoquinolinyl, dihydro-quinazolinyl, tetrahydro-quinazolinyl, dihydro-quinoxalinyl, tetrahydro-quinoxalinyl and the like. A heterocyclyl radical may be optionally substituted where allowed by available valences.

As used herein, the term "$C_{1-6}$alkoxy-carbonyl" refers to a radical of the formula: —C(O)—O—$C_{1-6}$alkyl.

As used herein, the term "$C_{1-6}$alkyl-amino" refers to a radical of the formula: —NH—$C_{1-6}$alkyl or —N($C_{1-6}$alkyl)$_2$.

As used herein, the term "$C_{1-6}$alkyl-amino-carbonyl" refers to a radical of the formula: —C(O)—NH—$C_{1-6}$alkyl or —C(O)—N($C_{1-6}$alkyl)$_2$.

As used herein, the term "$C_{1-6}$alkyl-carbonyl-amino" refers to a radical of the formula: —NH—C(O)—$C_{1-6}$alkyl, wherein amino may be optionally further substituted as previously defined.

As used herein, the term "amino" refers to a radical of the formula: —NH$_2$.

As used herein, the term "amino-carbonyl" refers to a radical of the formula: —C(O)—NH$_2$.

As used herein, the term "amino-$C_{1-6}$alkyl" refers to a radical of the formula: —$C_{1-6}$alkyl-NH$_2$.

As used herein, the term "aryloxy" refers to a radical of the formula: —O-aryl.

As used herein, the term "aryloxy-$C_{1-6}$alkyl" refers to a radical of the formula: —$C_{1-6}$alkyl-O-aryl.

As used herein, the term "carboxyl" refers to a radical of the formula: —COOH or —CO$_2$H.

As used herein, the term "carboxyl-$C_{1-6}$alkyl" refers to a radical of the formula: —$C_{1-6}$alkyl-COOH or —$C_{1-6}$alkyl-$CO_2$H.

As used herein, the term "$C_{3-14}$cycloalkyl-$C_{1-6}$alkyl" refers to a radical of the formula: —$C_{1-6}$alkyl-$C_{3-14}$cycloalkyl.

As used herein, the term "$C_{3-14}$cycloalkyloxy" refers to a radical of the formula: —O—$C_{3-14}$cycloalkyl.

As used herein, the term "halo" or "halogen" generally refers to a halogen atom radical, including fluoro, chloro, bromo and iodo.

As used herein, the term "halo-$C_{1-6}$alkoxy" refers to a radical of the formula: —O—$C_{1-6}$alkyl-halo, wherein $C_{1-6}$alkyl may be partially or completely substituted where allowed by available valences with one or more halogen atoms, including difluoromethoxy, trifluoromethoxy, difluoroethoxy or trifluoroethoxy and the like. In some embodiments, halo-$C_{1-6}$alkoxy includes halo-$C_{1-4}$alkoxy and the like.

As used herein, the term "halo-$C_{1-6}$alkyl" refers to a radical of the formula: —$C_{1-6}$alkyl-halo, wherein $C_{1-6}$alkyl may be partially or completely substituted where allowed by available valences with one or more halogen atoms, including difluoromethyl, trifluoromethyl, difluoroethyl, trifluoroethyl, difluoroisopropyl, trifluoroisopropyl, fluoro-tert-butyl, trifluoro-tert-butyl and the like. In some embodiments, halo-$C_{1-6}$alkyl includes halo-$C_{1-4}$alkyl and the like.

As used herein, the term "halo-$C_{1-6}$alkyl-amino" refers to a radical of the formula: —NH—$C_{1-6}$alkyl-halo, wherein the halo-$C_{1-6}$alkyl portion is as previously defined and, wherein amino may be optionally further substituted as previously defined.

As used herein, the term "heteroaryl-$C_{1-6}$alkyl" refers to a radical of the formula: —$C_{1-6}$alkyl-heteroaryl.

As used herein, the term "heterocyclyl-$C_{1-6}$alkyl" refers to a radical of the formula: —$C_{1-6}$alkyl-heterocyclyl.

As used herein, the term "heterocyclyl-carbonyl" refers to a radical of the formula: —C(O)-heterocyclyl.

As used herein, the term "hydroxy-$C_{1-6}$alkyl" refers to a radical of the formula: —$C_{1-6}$alkyl-hydroxy, wherein $C_{1-6}$alkyl may be partially or completely substituted where allowed by available valences with one or more hydroxy radicals.

As used herein, the term "hydroxy-$C_{1-6}$alkyl-amino" refers to a radical of the formula: —NH—$C_{1-8}$alkyl-hydroxy, wherein the hydroxy-$C_{1-6}$alkyl portion is as previously defined and, wherein amino may be optionally further substituted as previously defined.

For the purposes of this invention, where one or more functionalities encompassing substituent variables for a compound of Formula (I) are incorporated into a compound of Formula (I), each functionality appearing at any location within the disclosed compound may be independently selected, and as appropriate, independently substituted. Also, when any variable (e.g., aryl, heterocyclyl, etc.) occurs more than one time in any substituent list or in Formula (I), its definition on each occurrence is independent of its definition at every other occurrence. Further, where a more generic substituent is set forth for any position in the compounds of the present invention, it is understood that the generic substituent may be replaced with more specific substituents, and the resulting compound is within the scope of the compounds of the present invention.

As used herein, the terms "substituted" or "optionally substituted" mean that the subject substituents are known to one skilled in the art to be chemical moieties that are appropriate for substitution at a designated atom position, replacing one or more hydrogens on the designated atom with a selection from the indicated group, provided that the designated atom's normal valency under the existing circumstances is not exceeded, and that the substitution results in a stable compound. Combinations of substituents and/or variables are permissible only if such combinations result in stable compounds. It should also be noted that any carbon as well as heteroatom with unsatisfied valences as described or shown herein is assumed to have a sufficient number of hydrogen atom(s) to satisfy the valences described or shown.

As used herein, the terms "stable compound' or "stable structure" mean a compound that is sufficiently robust to survive isolation to a useful degree of purity from a reaction mixture and formulations thereof into an efficacious therapeutic agent.

As used herein, the term "optionally substituted" further means optional substitution with the specified groups, radicals or moieties.

As used herein, the terms "enhance" and "increase" in the context of inclusion of exon 7 of SMN2 into mRNA transcribed from the SMN2 gene or in the level of expression of a protein by a host cell are used interchangeably.

BRIEF DESCRIPTION OF THE DRAWINGS

FIG. 2: DNA sequence of the minigene from the SMN2-G minigene construct (SEQ ID NO:19). Within the sequence shown in FIG. 2, the following subsequences can be found:
 1-70: 5'UTR (deg)
 71-79: start codon and BamHI site (atgggatcc)
 80-190: exon 6
 191-5959: intron 6
 5960-6014: exon 7 with G insert (position 6008)
 6015-6458: intron 7
 6459-6481: part of exon 8
 6482-8146: BamHI site, luciferase coding sequence starting with codon 2, NotI site, TAA stop codon
 8147-8266: 3'UTR (deg).

FIG. 3: DNA sequence of the minigene from the SMN2-A minigene construct (SEQ ID NO:20). Within the sequence shown in FIG. 1, the following subsequences can be found:
 1-70: 5'UTR (deg)
 71-79: start codon and BamHI site (atgggatcc)
 80-190: exon 6
 191-5959: intron 6

5960-6014: exon 7 with A insert (position 6008)
6015-6458: intron 7
6459-6481: part of exon 8
6482-8146: BamHI site, luciferase coding sequence starting with codon 2, NotI site, TAA stop codon
8147-8266: 3'UTR (deg).

Figure 4:
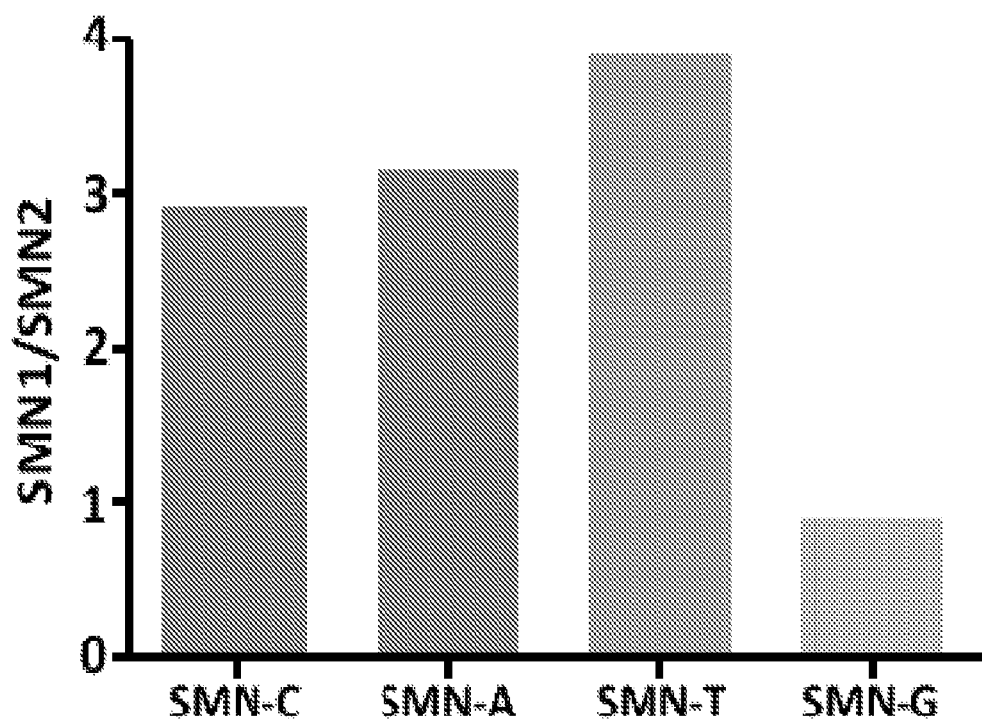

FIG. 4: Bar graphs showing the ratio of luciferase activity of corresponding SMN1 and SMN2 minigene constructs in transiently transfected HEK293H cells. HEK293H cells were transiently transfected with SMN1-A, SMN1-T, SMN1-C and SMN1-G versions of the SMN1 minigene construct. The luciferase activity in these cells was compared with the luciferase activity in HEK293H cells that were transiently transfected with the SMN2-A, SMN2-T, SMN2-C and SMN2-G versions of the SMN2 minigene construct. For example, to determine the ratio of luciferase activity, e.g., between HEK293H cells containing the two different C versions of the minigene construct, the luciferase activity values obtained for cells containing the SMN1-C construct were divided by the luciferase activity values obtained for cells containing the SMN2-C construct.

Figure 5:
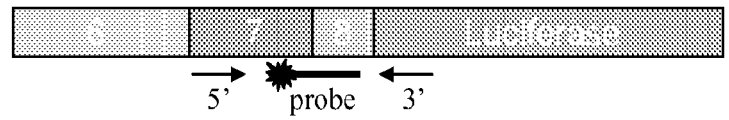

FIG. 5: Schematic drawing of SMN-qPCR secondary assay design. The 5' primer hybridizes to exon 7; the 3' primer hybridizes to luciferase; the probe hybridizes to the junction between exons 7 and 8. The primers and the probe produce a signal in real-time PCR only if the inclusion of exon 7 of SMN2 into mRNA transcribed from the SMN2 gene has been enhanced by a compound.

DETAILED DESCRIPTION OF THE INVENTION

The present invention provides nucleic acid constructs and screening assays for the identification and/or validation of compounds that enhance the inclusion of exon 7 of SMN2 into mRNA transcribed from the SMN2 gene.

The present invention provides compounds for use in methods for enhancing the expression of SMN in a human subject in need thereof and for treating SMA in a human subject in need thereof. A compound that enhances the inclusion of exon 7 of SMN2 into mRNA transcribed from the SMN2 gene increases levels of SMN protein produced from the SMN2 gene, and therefore, may increase SMN protein in SMA patients and thus, may provide a therapeutic benefit. In a specific embodiment, the compound binds directly to SMN2 pre-mRNA. In another embodiment, the compound binds to a regulatory protein(s) and/or a molecule(s) that binds and/or associates with SMN2 pre-mRNA, including, but not limited to a protein(s) needed for spliceosome formation. In another embodiment, the compound binds to a nucleotide regulatory sequence(s) of a gene(s) that encodes a protein(s) that binds and/or associates with SMN2 pre-mRNA.

In one embodiment, the present invention provides a method for enhancing the expression of SMN in a human subject in need thereof, comprising administering to the subject an effective amount of a compound of Formula (I) or a form thereof. In another embodiment, the present invention provides a use of a compound of Formula (I) or a form thereof for the preparation of a medicament that enhancing inclusion of exon 7 of SMN2 into mRNA transcribed from the SMN2 gene in a human subject in need thereof.

In one embodiment, the present invention provides a method for treating SMA in a human subject in need thereof, comprising administering to the subject an effective amount of a compound of Formula (I) or a form thereof. In another embodiment, the present invention provides a use of a compound of Formula (I) or a form thereof for the preparation of a medicament that treats SMA in a human subject in need thereof.

Embodiments of the present invention include a compound of Formula (I) having the following structure:

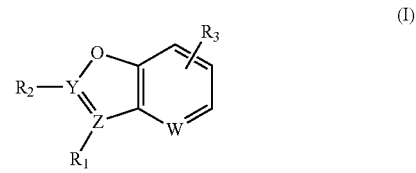

(I)

or a form thereof, wherein:

Y and Z are each independently selected from N or C, wherein Y and Z are each not simultaneously N or C;

W is N or C;

$R_1$ is selected from hydrogen or aryl, wherein aryl is optionally substituted with carboxyl and, wherein $R_1$ is absent when Z is N;

$R_2$ is selected from hydrogen, $C_{3-14}$cycloalkyl, aryl, heteroaryl or heterocyclyl, wherein aryl is optionally substituted with one, two, or three substituents each selected from halogen, carboxyl, $C_{1-6}$alkyl, $C_{1-6}$alkoxy, halo-$C_{1-6}$alkoxy, $C_{1-6}$alkoxy-carbonyl, amino or $C_{1-6}$alkyl-amino, or one substituent selected from halo-$C_{1-6}$alkyl-amino, hydroxy-$C_{1-6}$alkyl-amino, amino-carbonyl, $C_{1-6}$alkyl-amino-carbonyl, aryl, heteroaryl or heterocyclyl, optionally substituted on heterocyclyl with one or two oxo substituents, wherein heteroaryl is optionally substituted with one or two $C_{1-6}$alkyl substituents or one heterocyclyl substituent, wherein heterocyclyl is optionally substituted with one or two substituents each selected from halogen or $C_{1-6}$alkyl, and wherein $R_2$ is absent when Y is N; and $R_3$ is one, two, or three carbon atom substituents each selected from hydrogen, halogen, carboxyl, $C_{1-6}$alkyl, $C_{1-6}$alkoxy, amino, amino-$C_{1-6}$alkyl, $C_{1-6}$alkyl-carbonyl-amino, $C_{3-14}$cycloalkyl, $C_{3-14}$cycloalkyloxy, $C_{3-14}$cycloalkyl-$C_{1-6}$alkyl, aryl, aryloxy, aryloxy-$C_{1-6}$alkyl, heteroaryl, heteroaryl-$C_{1-6}$alkyl, heterocyclyl, heterocyclyl-$C_{1-6}$alkyl or heterocyclyl-carbonyl, wherein each instance of amino is optionally substituted with one or two substituents each selected from $C_{1-6}$alkyl, hydroxy-$C_{1-6}$alkyl, carboxy-$C_{1-6}$alkyl, aryl-$C_{1-6}$alkyl, heterocyclyl-$C_{1-6}$alkyl or aryl optionally substituted with one or two $C_{1-6}$alkyl substituents, wherein each instance of aryl is optionally substituted with one or two substituents each selected from halogen, $C_{1-6}$alkyl, halo-$C_{1-6}$alkyl, $C_{1-6}$alkoxy, halo-$C_{1-6}$alkoxy or aryl optionally substituted with one or two $C_{1-6}$alkyl substituents, and wherein each instance of heterocyclyl is optionally substituted with one or two substituents each selected from $C_{1-6}$alkyl or aryl optionally substituted with one or two $C_{1-6}$alkyl substituents, or is optionally substituted on one or two carbon atoms with an oxo substituent.

In some embodiments, a compound includes a compound of Formula (I) or a form thereof wherein:

$R_2$ is selected from hydrogen, aryl, heteroaryl or heterocyclyl, wherein aryl is optionally substituted with one or two substituents each selected from halogen, carboxyl, C$_{1-6}$alkyl, C$_{1-6}$alkoxy, halo-C$_{1-6}$alkoxy or C$_{1-6}$alkoxycarbonyl, or one substituent selected from halo-C$_{1-6}$alkyl-amino, hydroxy-C$_{1-6}$alkyl-amino, amino-carbonyl, aryl, heteroaryl or heterocyclyl optionally substituted with one oxo substituent, wherein heteroaryl is optionally substituted with one or two C$_{1-6}$alkyl substituents or one heterocyclyl substituent, wherein heterocyclyl is optionally substituted with two halogen substituents, and wherein R$_2$ is absent when Y is N; and R$_3$ is one, two, or three carbon atom substituents each selected from hydrogen, halogen, carboxyl, C$_{1-6}$alkyl, C$_{1-6}$alkoxy, amino, amino-C$_{1-6}$alkyl, C$_{1-6}$alkyl-carbonyl-amino, aryl, aryloxy, aryloxy-C$_{1-6}$alkyl, heteroaryl, heteroaryl-C$_{1-6}$alkyl, heterocyclyl or heterocyclyl-carbonyl, wherein each instance of amino is optionally substituted with one or two substituents each selected from C$_{1-6}$alkyl, hydroxy-C$_{1-6}$alkyl, carboxy-C$_{1-6}$alkyl, aryl-C$_{1-6}$alkyl, heterocyclyl-C$_{1-6}$alkyl or aryl optionally substituted with one or two C$_{1-6}$alkyl substituents, wherein each instance of aryl is optionally substituted with one or two substituents each selected from halogen, C$_{1-6}$alkyl, halo-C$_{1-6}$alkyl, C$_{1-6}$alkoxy or halo-C$_{1-6}$alkoxy, and wherein each instance of heterocyclyl is optionally substituted with one or two C$_{1-6}$alkyl substituents, or is optionally substituted on a carbon atom with an oxo substituent.

In some embodiments, a compound includes a compound of Formula (I) or a form thereof wherein:

R$_1$ is selected from hydrogen or phenyl, wherein phenyl is optionally substituted with carboxyl and, wherein R$_1$ is absent when Z is N;

R$_2$ is selected from hydrogen, phenyl, furanyl, thienyl, pyridinyl, 2,3-dihydro-benzofuranyl or benzo[1,3]dioxolyl, wherein phenyl is optionally substituted with one or two substituents each selected from halogen, carboxyl, C$_{1-6}$alkyl, C$_{1-6}$alkoxy, halo-C$_{1-6}$alkoxy or C$_{1-6}$alkoxycarbonyl, or one substituent selected from halo-C$_{1-6}$alkyl-amino, hydroxy-C$_{1-6}$alkyl-amino, amino-carbonyl, phenyl, pyrazolyl, azetidinyl, pyrrolidinyl or morpholinyl, optionally substituted on pyrrolidinyl with one oxo substituent, wherein furanyl, thienyl and pyridinyl is optionally substituted with one or two C$_{1-6}$alkyl substituents or one azetidinyl, pyrrolidinyl, piperidinyl, piperazinyl or morpholinyl substituent, wherein benzo[1,3]dioxolyl is optionally substituted with two halogen substituents, and wherein R$_2$ is absent when Y is N; and R$_3$ is one, two, or three carbon atom substituents each selected from hydrogen, halogen, carboxyl, C$_{1-6}$alkyl, C$_{1-6}$alkoxy, amino, amino-C$_{1-6}$alkyl, C$_{1-6}$alkyl-carbonyl-amino, phenyl, phenyloxy, phenyloxy-C$_{1-6}$alkyl, imidazolyl, pyrazolyl, 1H-1,2,4-triazolyl, benzofuranyl, imidazolyl-C$_{1-6}$alkyl, azetidinyl, pyrrolidinyl, piperidinyl, piperazinyl, morpholinyl, 1,4-diazepanyl, 2,3-dihydro-indolyl, 3,4-dihydroisoquinolin-(1H)-yl, 1,4-dioxa-8-azaspiro[4.5]decanyl, pyrrolidinyl-carbonyl or morpholinyl-carbonyl, wherein each instance of amino is optionally substituted with one or two substituents each selected from C$_{1-6}$alkyl, hydroxy-C$_{1-6}$alkyl, carboxy-C$_{1-6}$alkyl, phenyl-C$_{1-6}$alkyl, benzo[1,3]dioxolyl-C$_{1-6}$alkyl, or phenyl optionally substituted with one or two C$_{1-6}$alkyl substituents, wherein each instance of phenyl is optionally substituted with one or two substituents each selected from halogen, C$_{1-6}$alkyl, halo-C$_{1-6}$alkyl, C$_{1-6}$alkoxy or halo-C$_{1-6}$alkoxy, and wherein each instance of azetidinyl, pyrrolidinyl, piperazinyl, morpholinyl or 1,4-diazepanyl is optionally substituted with one or two C$_{1-6}$alkyl substituents, or is optionally substituted on one azetidinyl or pyrrolidinyl carbon atom with an oxo substituent.

In some embodiments, a compound includes a compound of Formula (I) or a form thereof selected from the group consisting of a compound of Formula (Ia), Formula (Ib), Formula (Ic), Formula (Id), Formula (Ie) and Formula (If) or forms thereof, wherein all substituent variables are as previously defined:

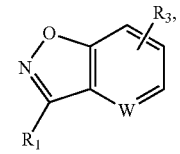

(Ia)

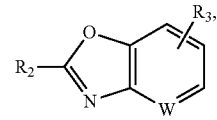

(Ib)

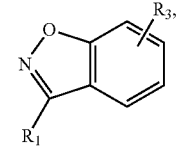

(Ic)

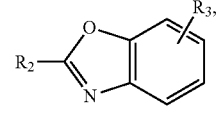

(Id)

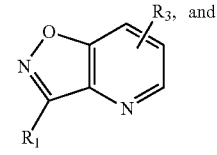

(Ie)

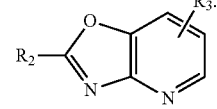

(If)

In some embodiments, a form of a compound of Formula (I), Formula (Ia), Formula (Ib), Formula (Ic), Formula (Id), Formula (Ie) or Formula (If) is selected from a pharmaceutically acceptable free acid, free base, salt, hydrate, solvate, clathrate, racemate, stereoisomer, or polymorph thereof.

In some embodiments, a compound of Formula (I) or a form thereof for use in the present invention is selected from the group consisting of:

1
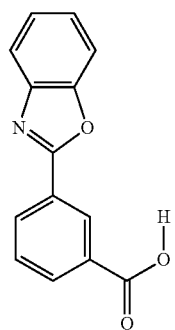
2
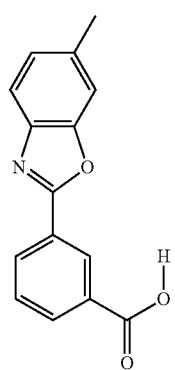
3
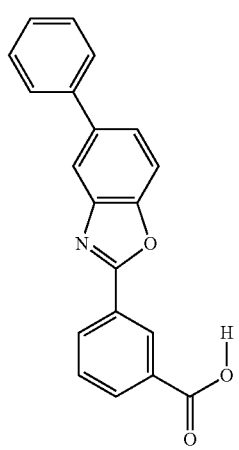
4
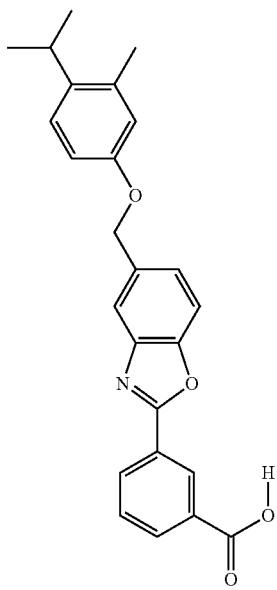
5
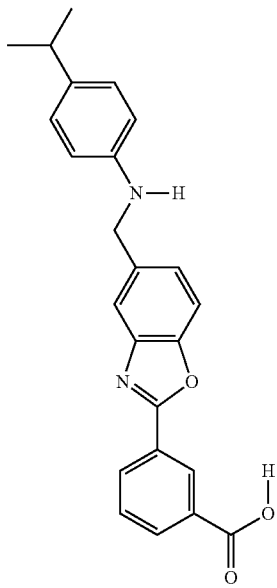
6
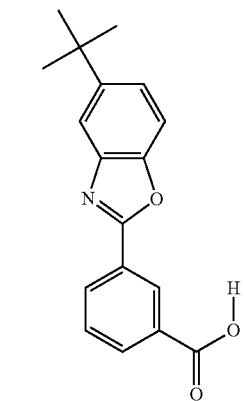

7
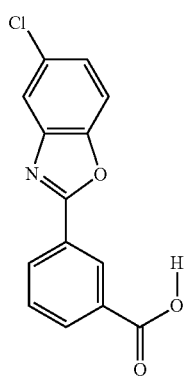
8
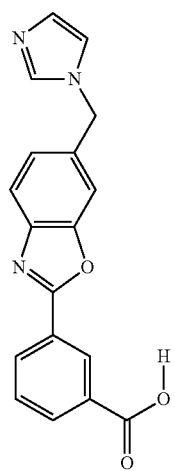
9
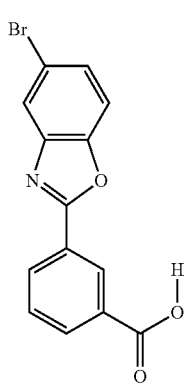
10
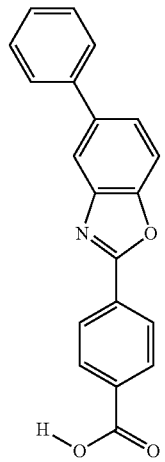
11
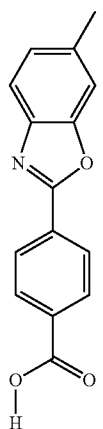
12
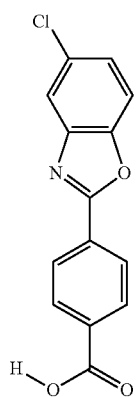

13
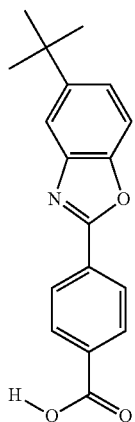
14
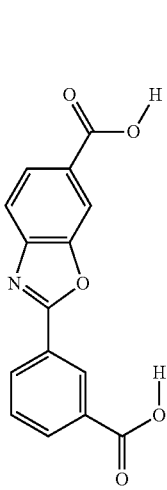
15
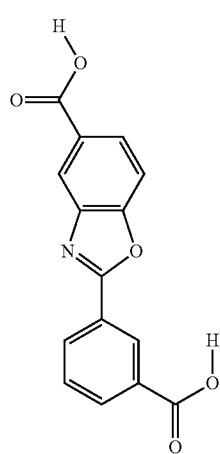
16
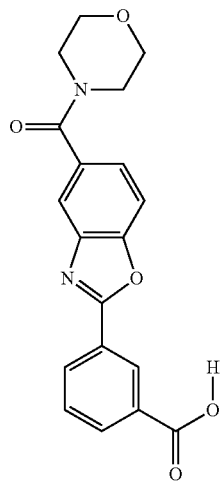
17
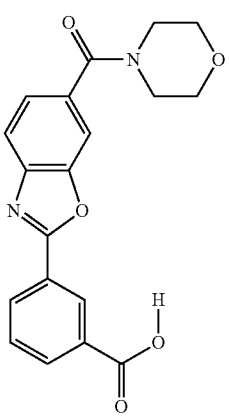
18
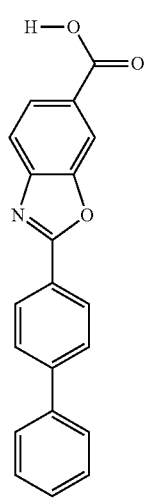

19
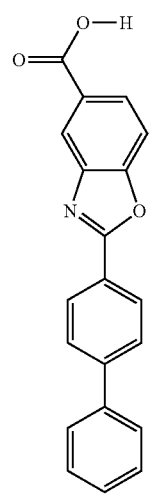
20
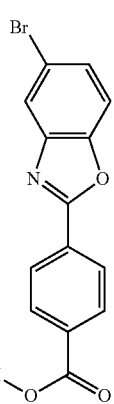
21
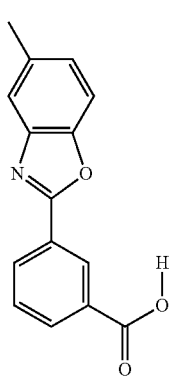
22
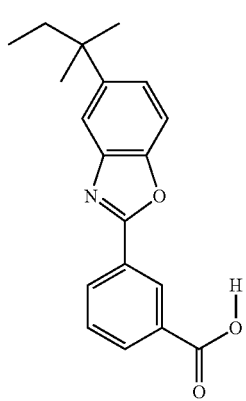
23
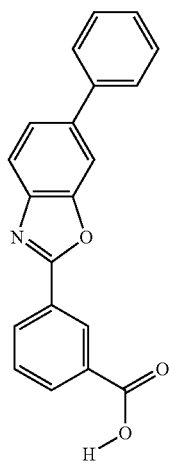
24
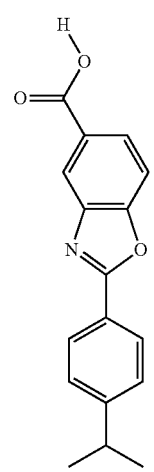
25
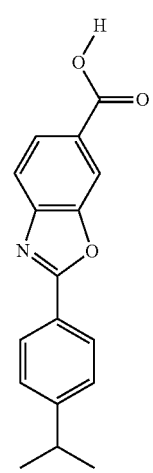

26
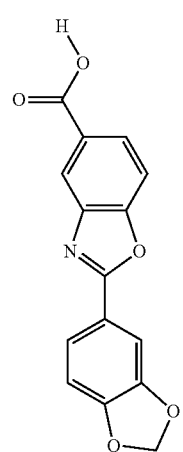
27
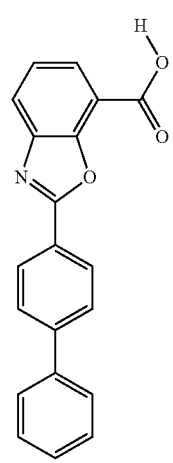
28
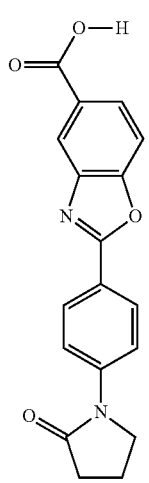
29
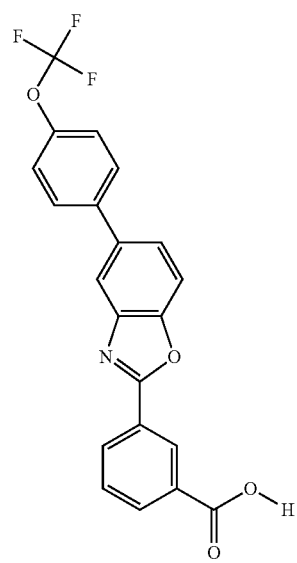
30
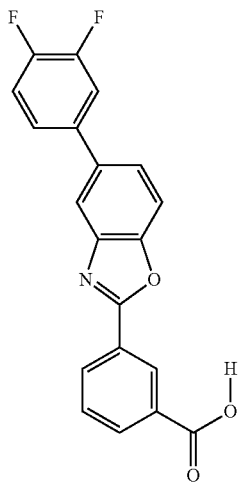
31
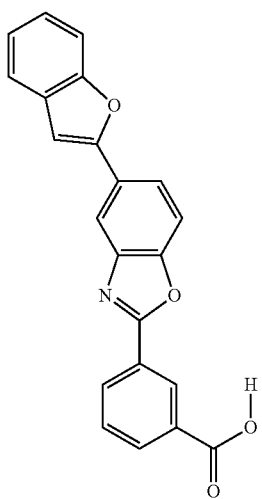

| 32 | 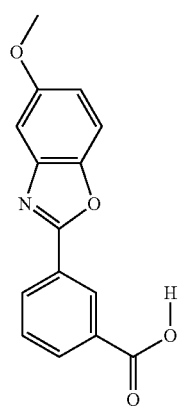 | 35 | 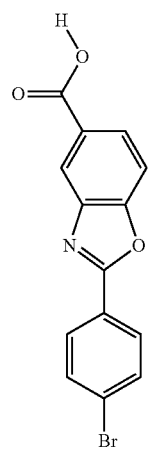 |
| 33 | 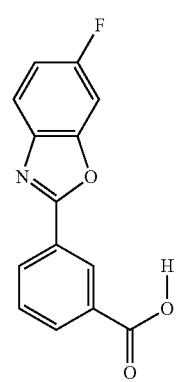 | 36 | 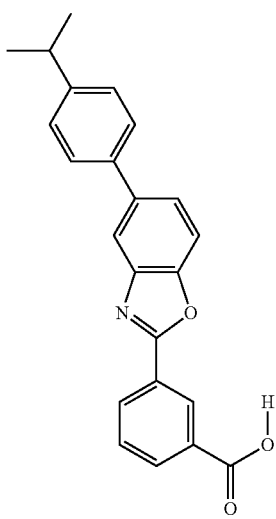 |
| 34 | 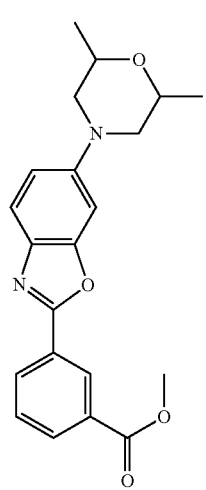 | 37 | 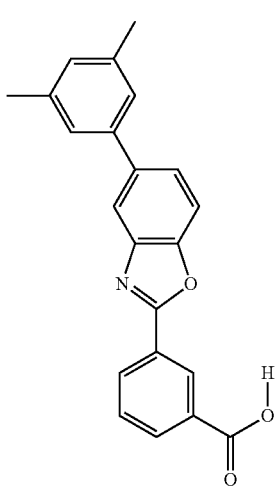 |

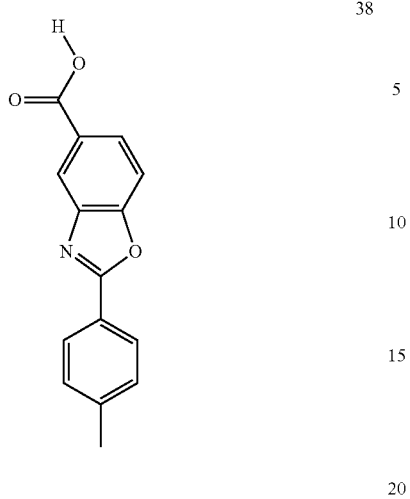
38
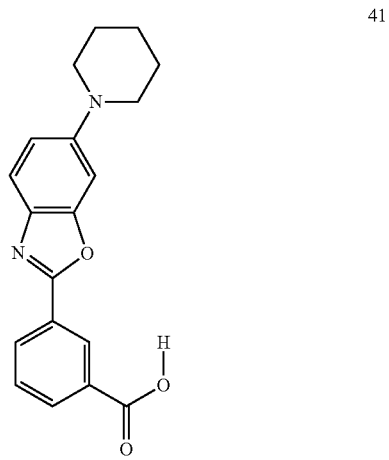
41
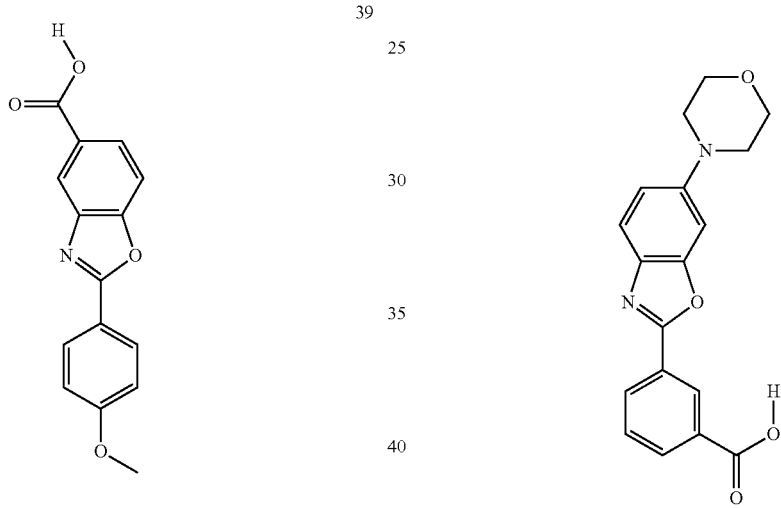
39
42
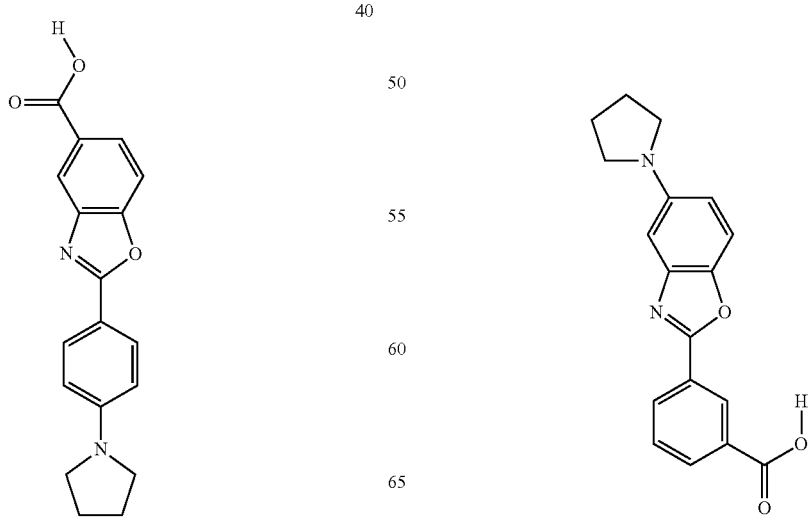
40
43

44
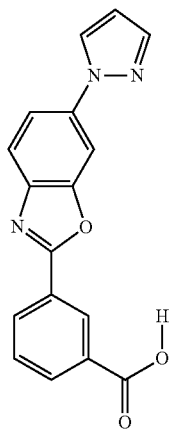
45
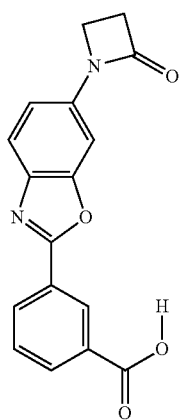
46
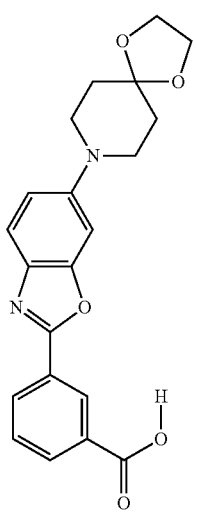
47
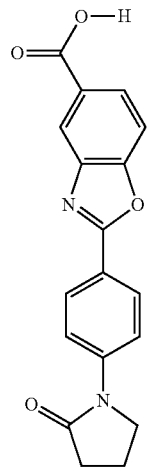
48
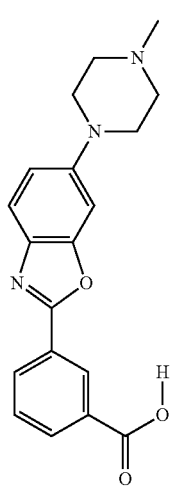
49
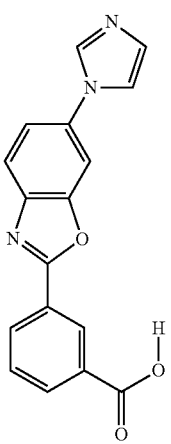

50
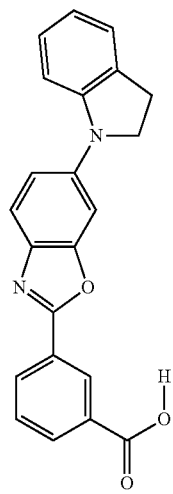
51
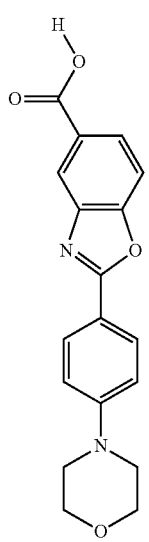
52
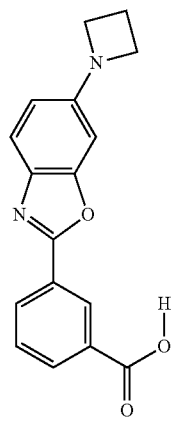
53
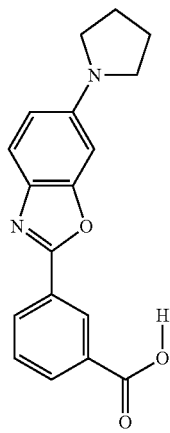
54
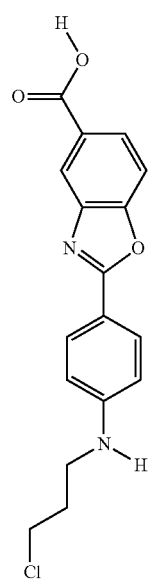
55
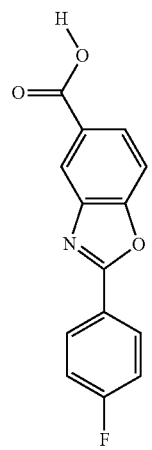

56
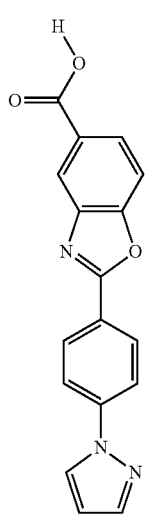
57
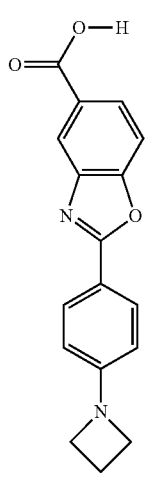
58
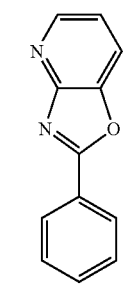
59
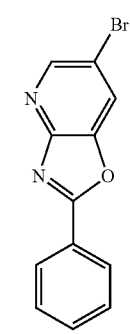
60
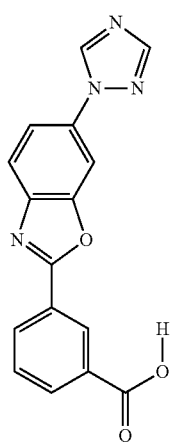
61
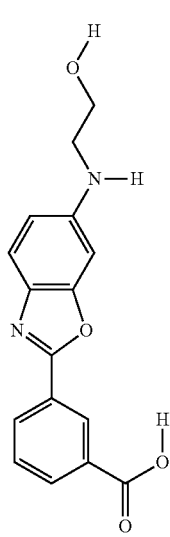
62
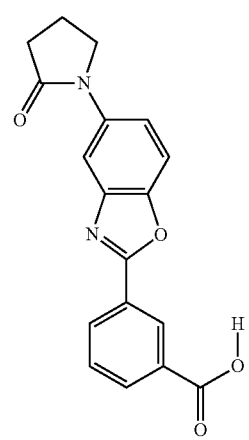

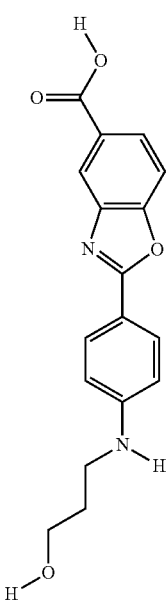
63
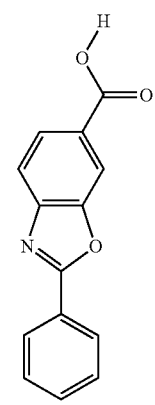
64
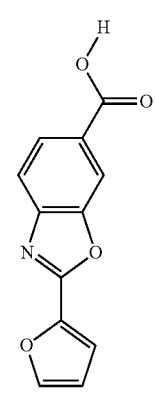
65
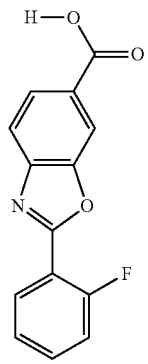
66
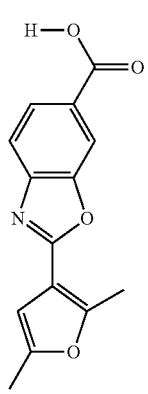
67
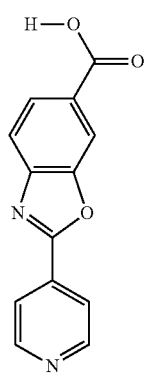
68
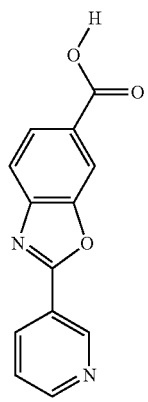
69

70
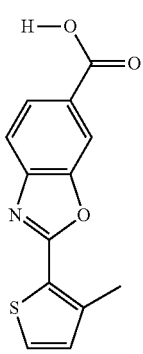
71
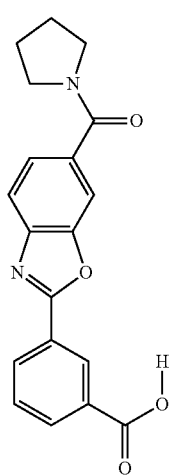
72
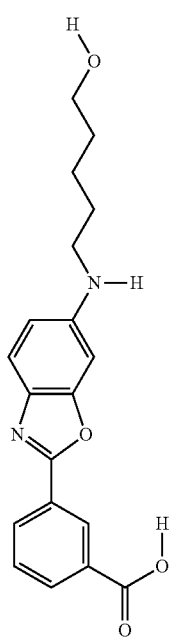
73
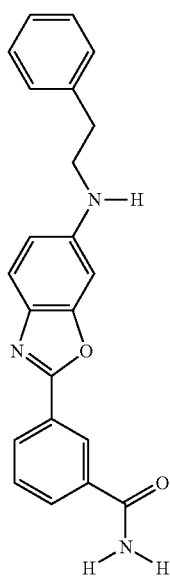
74
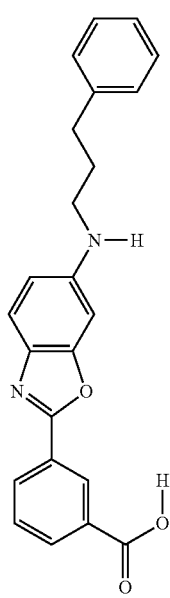
75
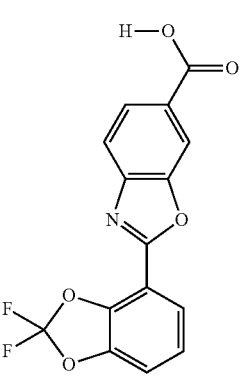

76 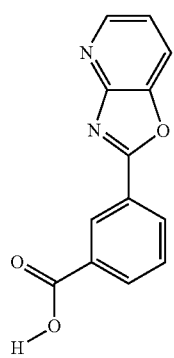
77 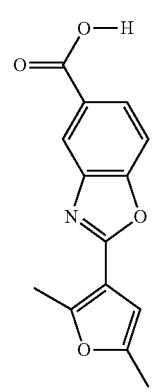
78 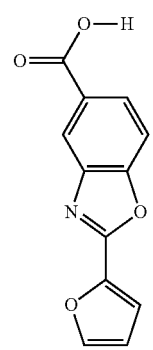
79 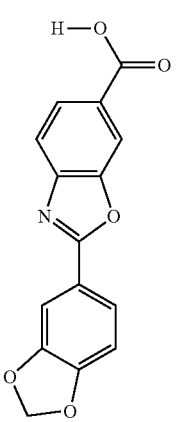
80 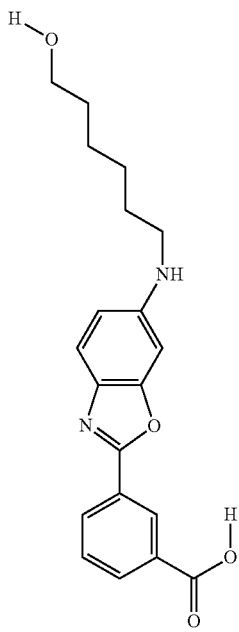
81 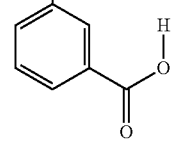
82 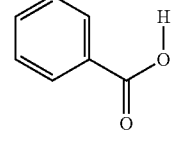

83
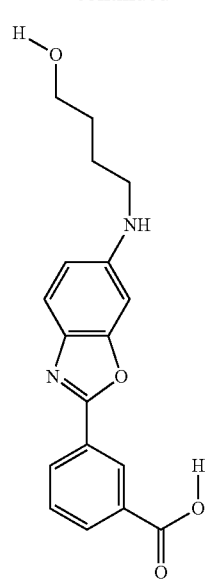
84
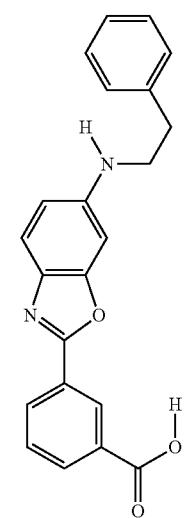
85
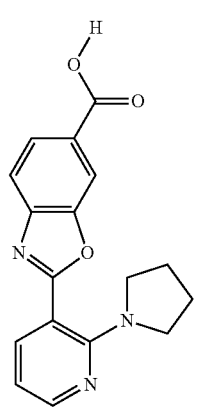
86
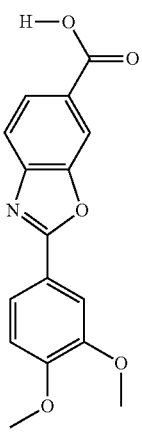
87
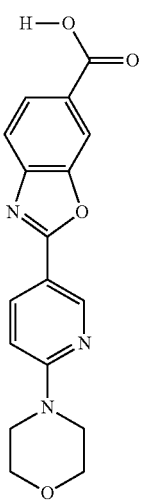
88
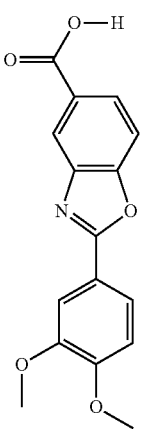

89
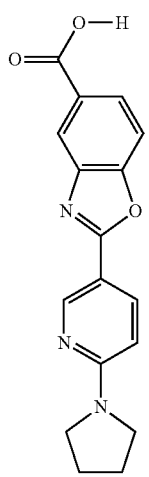
92
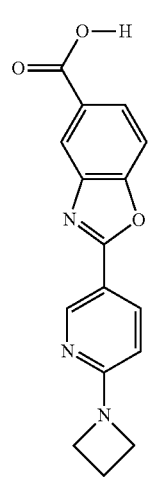
90
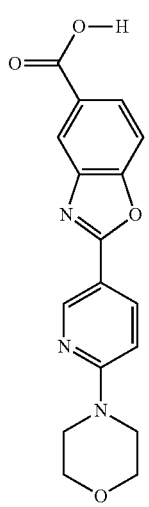
93
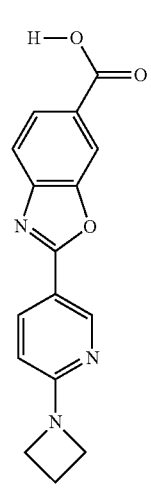
91
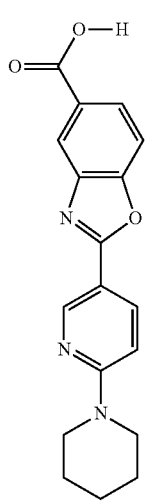
94
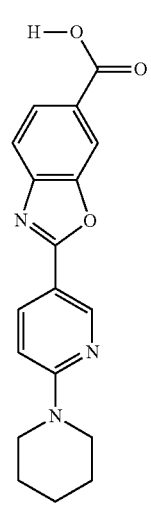

95 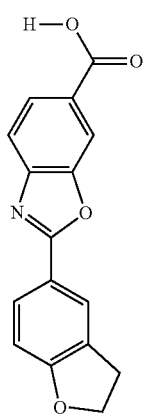
98 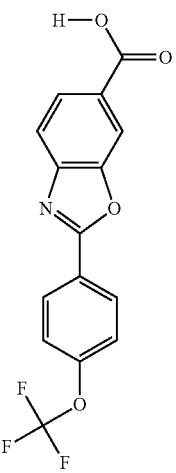
96 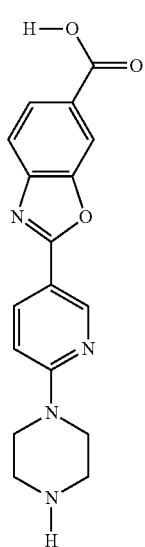
99 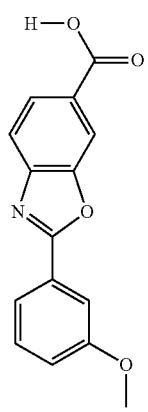
97 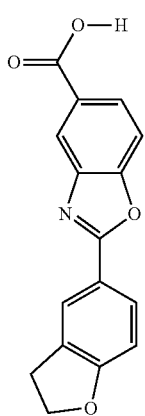
100 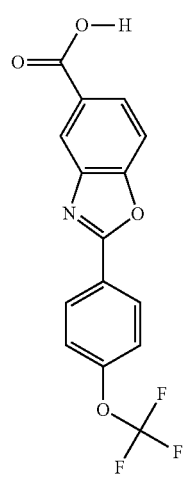

71
-continued
101 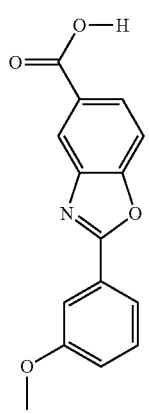
102 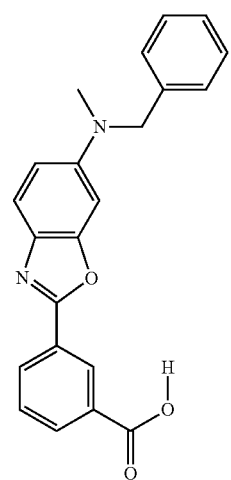
103 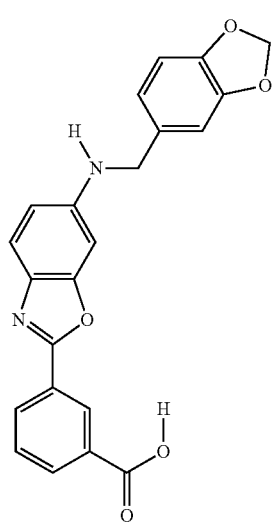
72
-continued
104 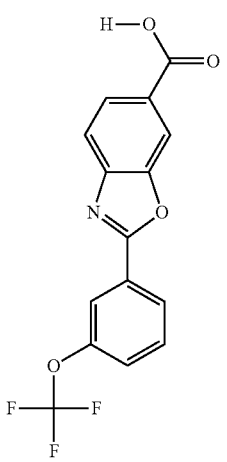
105 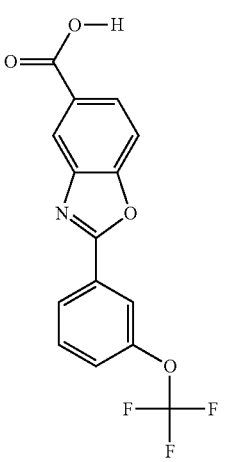
106 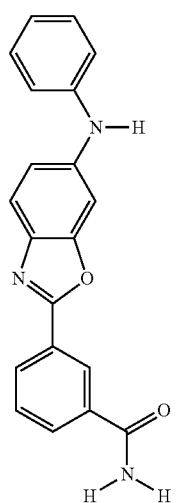

107 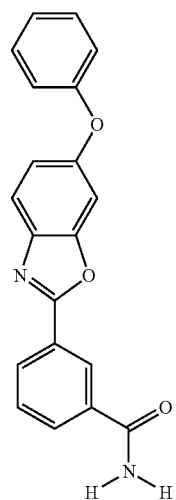
108 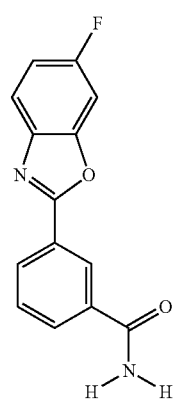
109 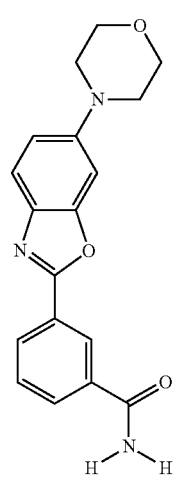
110 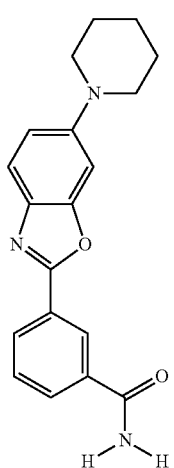
111 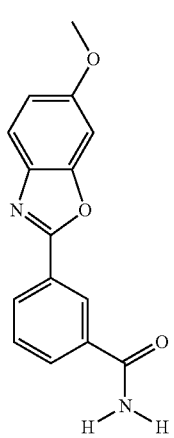
112 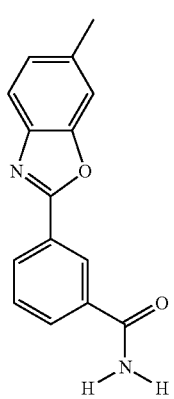

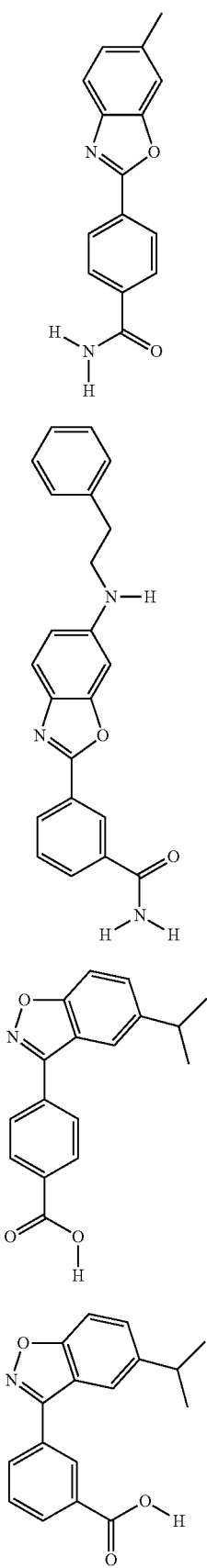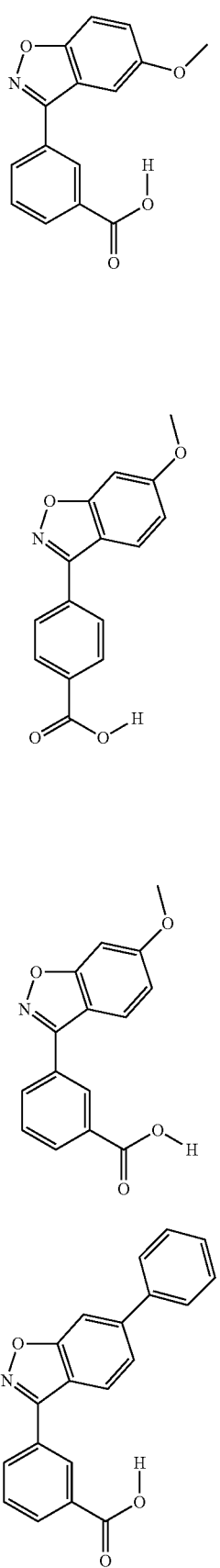

| 77 -continued | 78 -continued |
|---|---|
| 121 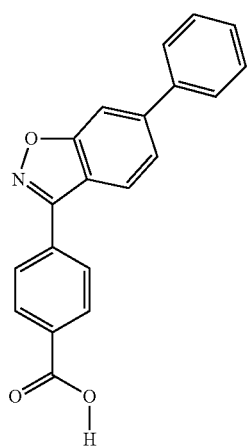 | 124 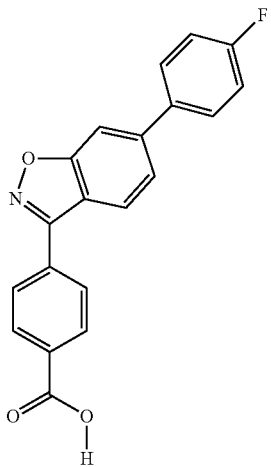 |
| 122 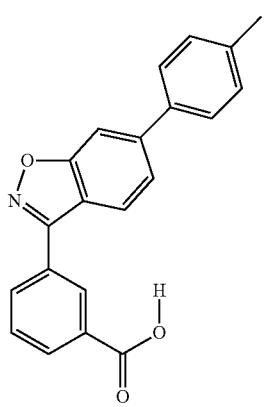 | 125 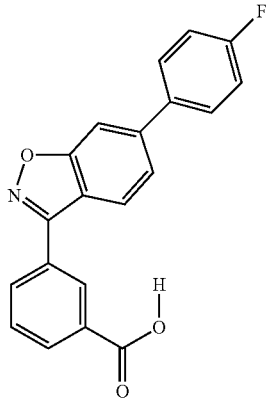 |
| 123 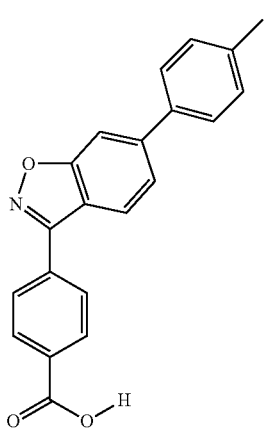 | 126 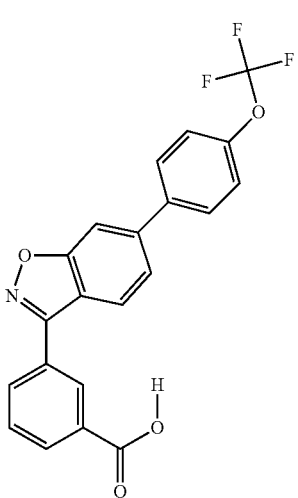 |

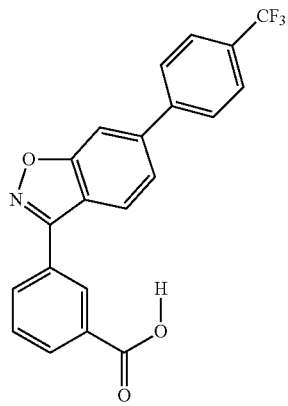

127

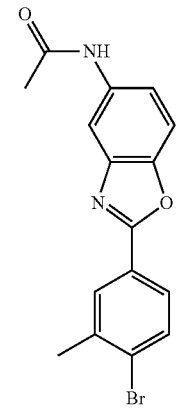

128

In some embodiments, a compound for use in the present invention is one of the following compounds:

| Cpd | Name |
|---|---|
| 1 | 3-benzooxazol-2-yl-benzoic acid, |
| 2 | 3-(6-methyl-benzooxazol-2-yl)-benzoic acid, |
| 3 | 3-(5-phenyl-benzooxazol-2-yl)-benzoic acid, |
| 4 | 3-[5-(4-isopropyl-3-methyl-phenoxymethyl)-benzooxazol-2-yl]-benzoic acid, |
| 5 | 3-{5-[(4-isopropyl-phenylamino)-methyl]-benzooxazol-2-yl}-benzoic acid, |
| 6 | 3-(5-tert-butyl-benzooxazol-2-yl)-benzoic acid, |
| 7 | 3-(5-chloro-benzooxazol-2-yl)-benzoic acid, |
| 8 | 3-(6-imidazol-1-ylmethyl-benzooxazol-2-yl)-benzoic acid, |
| 9 | 3-(5-bromo-benzooxazol-2-yl)-benzoic acid, |
| 10 | 4-(5-phenyl-benzooxazol-2-yl)-benzoic acid, |
| 11 | 4-(6-methyl-benzooxazol-2-yl)-benzoic acid, |
| 12 | 4-(5-chloro-benzooxazol-2-yl)-benzoic acid, |
| 13 | 4-(5-tert-butyl-benzooxazol-2-yl)-benzoic acid, |
| 14 | 2-(3-carboxy-phenyl)-benzooxazole-6-carboxylic acid, |
| 15 | 2-(3-carboxy-phenyl)-benzooxazole-5-carboxylic acid, |
| 16 | 3-[5-(morpholine-4-carbonyl)-benzooxazol-2-yl]-benzoic acid, |
| 17 | 3-[6-(morpholine-4-carbonyl)-benzooxazol-2-yl]-benzoic acid, |
| 18 | 2-biphenyl-4-yl-benzooxazole-6-carboxylic acid, |
| 19 | 2-biphenyl-4-yl-benzooxazole-5-carboxylic acid, |
| 20 | 4-(5-bromo-benzooxazol-2-yl)-benzoic acid, |
| 21 | 3-(5-methyl-benzooxazol-2-yl)-benzoic acid, |
| 22 | 3-[5-(1,1-dimethyl-propyl)-benzooxazol-2-yl]-benzoic acid, |
| 23 | 3-(6-Phenyl-benzooxazol-2-yl)-benzoic acid, |
| 24 | 2-(4-isopropyl-phenyl)-benzooxazole-5-carboxylic acid, |
| 25 | 2-(4-isopropyl-phenyl)-benzooxazole-6-carboxylic acid, |
| 26 | 2-benzo[1,3]dioxol-5-yl-benzooxazole-5-carboxylic acid, |
| 27 | 2-biphenyl-4-yl-benzooxazole-7-carboxylic acid, |
| 28 | 2-[4-(2-oxo-pyrrolidin-1-yl)-phenyl]-benzooxazole-5-carboxylic acid, |
| 29 | 3-[5-(4-trifluoromethoxy-phenyl)-benzooxazol-2-yl]-benzoic acid, |
| 30 | 3-[5-(3,4-difluoro-phenyl)-benzooxazol-2-yl]-benzoic acid, |
| 31 | 3-(5-benzofuran-2-yl-benzooxazol-2-yl)-benzoic acid, |
| 32 | 3-(5-methoxy-benzooxazol-2-yl)-benzoic acid, |
| 33 | 3-(6-fluoro-benzooxazol-2-yl)-benzoic acid, |
| 34 | 3-[6-(2,6-dimethyl-morpholin-4-yl)-benzooxazol-2-yl]-benzoic acid methyl ester, |
| 35 | 2-(4-bromo-phenyl)-benzooxazole-5-carboxylic acid, |
| 36 | 3-[5-(4-isopropyl-phenyl)-benzooxazol-2-yl]-benzoic acid, |
| 37 | 3-[5-(3,5-dimethyl-phenyl)-benzooxazol-2-yl]-benzoic acid, |
| 38 | 2-p-tolyl-benzooxazole-5-carboxylic acid, |
| 39 | 2-(4-methoxy-phenyl)-benzooxazole-5-carboxylic acid, |
| 40 | 2-(4-pyrrolidin-1-yl-phenyl)-benzooxazole-5-carboxylic acid, |
| 41 | 3-(6-piperidin-1-yl-benzooxazol-2-yl)-benzoic acid, |
| 42 | 3-(6-morpholin-4-yl-benzooxazol-2-yl)-benzoic acid, |
| 43 | 3-(5-pyrrolidin-1-yl-benzooxazol-2-yl)-benzoic acid, |
| 44 | 3-(6-pyrazol-1-yl-benzooxazol-2-yl)-benzoic acid, |
| 45 | 3-[6-(2-oxo-azetidin-1-yl)-benzooxazol-2-yl]-benzoic acid, |
| 46 | 3-[6-(1,4-dioxa-8-aza-spiro[4.5]dec-8-yl)-benzooxazol-2-yl]-benzoic acid, |
| 47 | 2-[4-(2-oxo-pyrrolidin-1-yl)-phenyl]-benzooxazole-5-carboxylic acid, |
| 48 | 3-[6-(4-methyl-piperazin-1-yl)-benzooxazol-2-yl]-benzoic acid, |
| 49 | 3-(6-imidazol-1-yl-benzooxazol-2-yl)-benzoic acid, |
| 50 | 3-[6-(2,3-dihydro-indol-1-yl)-benzooxazol-2-yl]-benzoic acid, |

-continued

| Cpd | Name |
|---|---|
| 51 | 2-(4-morpholin-4-yl-phenyl)-benzooxazole-5-carboxylic acid, |
| 52 | 3-(6-azetidin-1-yl-benzooxazol-2-yl)-benzoic acid, |
| 53 | 3-(6-pyrrolidin-1-yl-benzooxazol-2-yl)-benzoic acid, |
| 54 | 2-[4-(3-chloro-propylamino)-phenyl]-benzooxazole-5-carboxylic acid, |
| 55 | 2-(4-fluoro-phenyl)-benzooxazole-5-carboxylic acid, |
| 56 | 2-(4-pyrazol-1-yl-phenyl)-benzooxazole-5-carboxylic acid, |
| 57 | 2-(4-azetidin-1-yl-phenyl)-benzooxazole-5-carboxylic acid, |
| 58 | 2-phenyl-oxazolo[4,5-b]pyridine, |
| 59 | 6-bromo-2-phenyl-oxazolo[4,5-b]pyridine, |
| 60 | 3-(6-[1,2,4]triazol-1-yl-benzooxazol-2-yl)-benzoic acid, |
| 61 | 3-[6-(2-hydroxy-ethylamino)-benzooxazol-2-yl]-benzoic acid, |
| 62 | 3-[5-(2-oxo-pyrrolidin-1-yl)-benzooxazol-2-yl]-benzoic acid, |
| 63 | 2-[4-(3-hydroxy-propylamino)-phenyl]-benzooxazole-5-carboxylic acid, |
| 64 | 2-phenyl-benzooxazole-6-carboxylic acid, |
| 65 | 2-furan-2-yl-benzooxazole-6-carboxylic acid, |
| 66 | 2-(2-fluoro-phenyl)-benzooxazole-6-carboxylic acid, |
| 67 | 2-(2,5-dimethyl-furan-3-yl)-benzooxazole-6-carboxylic acid, |
| 68 | 2-pyridin-4-yl-benzooxazole-6-carboxylic acid, |
| 69 | 2-pyridin-3-yl-benzooxazole-6-carboxylic acid, |
| 70 | 2-(3-methyl-thiophen-2-yl)-benzooxazole-6-carboxylic acid, |
| 71 | 3-[6-(pyrrolidine-1-carbonyl)-benzooxazol-2-yl]-benzoic acid, |
| 72 | 3-[6-(5-hydroxy-pentylamino)-benzooxazol-2-yl]-benzoic acid, |
| 73 | 3-(6-phenethylamino-benzooxazol-2-yl)-benzamide, |
| 74 | 3-[6-(3-phenyl-propylamino)-benzooxazol-2-yl]-benzoic acid, |
| 75 | 2-(2,2-difluoro-benzo[1,3]dioxol-4-yl)-benzooxazole-6-carboxylic acid, |
| 76 | 3-oxazolo[4,5-b]pyridin-2-yl-benzoic acid, |
| 77 | 2-(2,5-dimethyl-furan-3-yl)-benzooxazole-5-carboxylic acid, |
| 78 | 2-furan-2-yl-benzooxazole-5-carboxylic acid, |
| 79 | 2-benzo[1,3]dioxol-5-yl-benzooxazole-6-carboxylic acid, |
| 80 | 3-[6-(6-hydroxy-hexylamino)-benzooxazol-2-yl]-benzoic acid, |
| 81 | 3-[6-(4-methyl-[1,4]diazepan-1-yl)-benzooxazol-2-yl]-benzoic acid, |
| 82 | 3-(6-phenoxy-benzooxazol-2-yl)-benzoic acid, |
| 83 | 3-[6-(4-hydroxy-butylamino)-benzooxazol-2-yl]-benzoic acid, |
| 84 | 3-(6-phenethylamino-benzooxazol-2-yl)-benzoic acid, |
| 85 | 2-(2-pyrrolidin-1-yl-pyridin-3-yl)-benzooxazole-6-carboxylic acid, |
| 86 | 2-(3,4-dimethoxy-phenyl)-benzooxazole-6-carboxylic acid, |
| 87 | 2-(6-morpholin-4-yl-pyridin-3-yl)-benzooxazole-6-carboxylic acid, |
| 88 | 2-(3,4-dimethoxy-phenyl)-benzooxazole-5-carboxylic acid, |
| 89 | 2-(6-pyrrolidin-1-yl-pyridin-3-yl)-benzooxazole-5-carboxylic acid, |
| 90 | 2-(6-morpholin-4-yl-pyridin-3-yl)-benzooxazole-5-carboxylic acid, |
| 91 | 2-(3,4,5,6-tetrahydro-2H-[1,2']bipyridinyl-5'-yl)-benzooxazole-5-carboxylic acid, |
| 92 | 2-(6-azetidin-1-yl-pyridin-3-yl)-benzooxazole-5-carboxylic acid, |
| 93 | 2-(6-azetidin-1-yl-pyridin-3-yl)-benzooxazole-6-carboxylic acid, |
| 94 | 2-(3,4,5,6-tetrahydro-2H-[1,2']bipyridinyl-5'-yl)-benzoxazole-6-carboxylic acid, |
| 95 | 2-(2,3-dihydro-benzofuran-5-yl)-benzooxazole-6-carboxylic acid, |
| 96 | 2-(6-piperazin-1-yl-pyridin-3-yl)-benzooxazole-6-carboxylic acid, |
| 97 | 2-(2,3-dihydro-benzofuran-5-yl)-benzooxazole-5-carboxylic acid, |
| 98 | 2-(4-trifluoromethoxy-phenyl)-benzooxazole-6-carboxylic acid, |
| 99 | 2-(3-methoxy-phenyl)-benzooxazole-6-carboxylic acid, |
| 100 | 2-(4-trifluoromethoxy-phenyl)-benzooxazole-5-carboxylic acid, |
| 101 | 2-(3-methoxy-phenyl)-benzooxazole-5-carboxylic acid, |
| 102 | 3-[6-(benzyl-methyl-amino)-benzooxazol-2-yl]-benzoic acid, |
| 103 | 3-{6-[(benzo[1,3]dioxol-5-ylmethyl)-amino]-benzooxazol-2-yl}-benzoic acid, |
| 104 | 2-(3-trifluoromethoxy-phenyl)-benzooxazole-6-carboxylic acid, |
| 105 | 2-(3-trifluoromethoxy-phenyl)-benzooxazole-5-carboxylic acid, |
| 106 | 3-(6-phenylamino-benzooxazol-2-yl)-benzamide, |
| 107 | 3-(6-phenoxy-benzooxazol-2-yl)-benzamide, |
| 108 | 3-(6-fluoro-benzooxazol-2-yl)-benzamide, |
| 109 | 3-(6-morpholin-4-yl-benzooxazol-2-yl)-benzamide, |
| 110 | 3-(6-piperidin-1-yl-benzooxazol-2-yl)-benzamide, |
| 111 | 3-(6-methoxy-benzooxazol-2-yl)-benzamide, |
| 112 | 3-(6-methyl-benzooxazol-2-yl)-benzamide, |
| 113 | 4-(6-methyl-benzooxazol-2-yl)-benzamide, |
| 114 | 3-(6-phenethylamino-benzooxazol-2-yl)-benzamide, |
| 115 | 4-(5-isopropyl-benzo[d]isoxazol-3-yl)-benzoic acid, |
| 116 | 3-(5-isopropyl-benzo[d]isoxazol-3-yl)-benzoic acid, |
| 117 | 3-(5-methoxy-benzo[d]isoxazol-3-yl)-benzoic acid, |
| 118 | 4-(6-methoxy-benzo[d]isoxazol-3-yl)-benzoic acid, |
| 119 | 3-(6-methoxy-benzo[d]isoxazol-3-yl)-benzoic acid, |
| 120 | 3-(6-phenyl-benzo[d]isoxazol-3-yl)-benzoic acid, |
| 121 | 4-(6-phenyl-benzo[d]isoxazol-3-yl)-benzoic acid, |
| 122 | 3-(6-p-tolyl-benzo[d]isoxazol-3-yl)-benzoic acid, |
| 123 | 4-(6-p-tolyl-benzo[d]isoxazol-3-yl)-benzoic acid, |
| 124 | 4-[6-(4-fluoro-phenyl)-benzo[d]isoxazol-3-yl]-benzoic acid, |
| 125 | 3-[6-(4-fluoro-phenyl)-benzo[d]isoxazol-3-yl]-benzoic acid, |
| 126 | 3-[6-(4-trifluoromethoxy-phenyl)-benzo[d]isoxazol-3-yl]-benzoic acid, |

| Cpd | Name |
| --- | --- |
| 127 | 3-[6-(4-trifluoromethyl-phenyl)-benzo[d]isoxazol-3-yl]-benzoic acid, and |
| 128 | N-[2-(4-bromo-3-methyl-phenyl)-benzooxazol-5-yl]-acetamide. |

In some embodiments, a compound for use in the present invention is one of the following compounds:

| Cpd | Name |
| --- | --- |
| 2 | 3-(6-methyl-benzooxazol-2-yl)-benzoic acid, |
| 6 | 3-(5-tert-butyl-benzooxazol-2-yl)-benzoic acid, |
| 8 | 3-(6-imidazol-1-ylmethyl-benzooxazol-2-yl)-benzoic acid, |
| 11 | 4-(6-methyl-benzooxazol-2-yl)-benzoic acid, |
| 18 | 2-biphenyl-4-yl-benzooxazole-6-carboxylic acid, |
| 19 | 2-biphenyl-4-yl-benzooxazole-5-carboxylic acid, |
| 21 | 3-(5-methyl-benzooxazol-2-yl)-benzoic acid, |
| 22 | 3-[5-(1,1-dimethyl-propyl)-benzooxazol-2-yl]-benzoic acid, |
| 23 | 3-(6-Phenyl-benzooxazol-2-yl)-benzoic acid, |
| 24 | 2-(4-isopropyl-phenyl)-benzooxazole-5-carboxylic acid, |
| 26 | 2-benzo[1,3]dioxol-5-yl-benzooxazole-5-carboxylic acid, |
| 28 | 2-[4-(2-oxo-pyrrolidin-1-yl)-phenyl]-benzooxazole-5-carboxylic acid, |
| 29 | 3-[5-(4-trifluoromethoxy-phenyl)-benzooxazol-2-yl]-benzoic acid, |
| 30 | 3-[5-(3,4-difluoro-phenyl)-benzooxazol-2-yl]-benzoic acid, |
| 31 | 3-(5-benzofuran-2-yl-benzooxazol-2-yl)-benzoic acid, |
| 32 | 3-(5-methoxy-benzooxazol-2-yl)-benzoic acid, |
| 35 | 2-(4-bromo-phenyl)-benzooxazole-5-carboxylic acid, |
| 36 | 3-[5-(4-isopropyl-phenyl)-benzooxazol-2-yl]-benzoic acid, |
| 37 | 3-[5-(3,5-dimethyl-phenyl)-benzooxazol-2-yl]-benzoic acid, |
| 38 | 2-p-tolyl-benzooxazole-5-carboxylic acid, |
| 39 | 2-(4-methoxy-phenyl)-benzooxazole-5-carboxylic acid, |
| 41 | 3-(6-piperidin-1-yl-benzooxazol-2-yl)-benzoic acid, |
| 42 | 3-(6-morpholin-4-yl-benzooxazol-2-yl)-benzoic acid, |
| 43 | 3-(5-pyrrolidin-1-yl-benzooxazol-2-yl)-benzoic acid, |
| 44 | 3-(6-pyrazol-1-yl-benzooxazol-2-yl)-benzoic acid, |
| 48 | 3-[6-(4-methyl-piperazin-1-yl)-benzooxazol-2-yl]-benzoic acid, |
| 51 | 2-(4-morpholin-4-yl-phenyl)-benzooxazole-5-carboxylic acid, |
| 52 | 3-(6-azetidin-1-yl-benzooxazol-2-yl)-benzoic acid, |
| 54 | 2-[4-(3-chloro-propylamino)-phenyl]-benzooxazole-5-carboxylic acid, |
| 55 | 2-(4-fluoro-phenyl)-benzooxazole-5-carboxylic acid, |
| 57 | 2-(4-azetidin-1-yl-phenyl)-benzooxazole-5-carboxylic acid, |
| 65 | 2-furan-2-yl-benzooxazole-6-carboxylic acid, |
| 66 | 2-(2-fluoro-phenyl)-benzooxazole-6-carboxylic acid, |
| 67 | 2-(2,5-dimethyl-furan-3-yl)-benzooxazole-6-carboxylic acid, |
| 69 | 2-pyridin-3-yl-benzooxazole-6-carboxylic acid, |
| 71 | 3-[6-(pyrrolidine-1-carbonyl)-benzooxazol-2-yl]-benzoic acid, |
| 73 | 3-(6-phenethylamino-benzooxazol-2-yl)-benzamide, |
| 77 | 2-(2,5-dimethyl-furan-3-yl)-benzooxazole-5-carboxylic acid, |
| 81 | 3-[6-(4-methyl-[1,4]diazepan-1-yl)-benzooxazol-2-yl]-benzoic acid, |
| 82 | 3-(6-phenoxy-benzooxazol-2-yl)-benzoic acid, |
| 89 | 2-(6-pyrrolidin-1-yl-pyridin-3-yl)-benzooxazole-5-carboxylic acid, |
| 90 | 2-(6-morpholin-4-yl-pyridin-3-yl)-benzooxazole-5-carboxylic acid, |
| 91 | 2-(3,4,5,6-tetrahydro-2H-[1,2']bipyridinyl-5'-yl)-benzooxazole-5-carboxylic acid, |
| 93 | 2-(6-azetidin-1-yl-pyridin-3-yl)-benzooxazole-6-carboxylic acid, |
| 100 | 2-(4-trifluoromethoxy-phenyl)-benzooxazole-5-carboxylic acid, |
| 102 | 3-[6-(benzyl-methyl-amino)-benzooxazol-2-yl]-benzoic acid, |
| 105 | 2-(3-trifluoromethoxy-phenyl)-benzooxazole-5-carboxylic acid, |
| 106 | 3-(6-phenylamino-benzooxazol-2-yl)-benzamide, |
| 110 | 3-(6-piperidin-1-yl-benzooxazol-2-yl)-benzamide, |
| 111 | 3-(6-methoxy-benzooxazol-2-yl)-benzamide, |
| 112 | 3-(6-methyl-benzooxazol-2-yl)-benzamide, and |
| 128 | N-[2-(4-bromo-3-methyl-phenyl)-benzooxazol-5-yl]-acetamide. |

In some embodiments, a compound for use in the present invention is one of the following compounds:

| Cpd | Name |
|---|---|
| 24 | 2-(4-isopropyl-phenyl)-benzooxazole-5-carboxylic acid, |
| 32 | 3-(5-methoxy-benzooxazol-2-yl)-benzoic acid, |
| 38 | 2-p-tolyl-benzooxazole-5-carboxylic acid, |
| 41 | 3-(6-piperidin-1-yl-benzooxazol-2-yl)-benzoic acid, |
| 66 | 2-(2-fluoro-phenyl)-benzooxazole-6-carboxylic acid, |
| 89 | 2-(6-pyrrolidin-1-yl-pyridin-3-yl)-benzooxazole-5-carboxylic acid, and |
| 128 | N-[2-(4-bromo-3-methyl-phenyl)-benzooxazol-5-yl]-acetamide. |

The present invention includes a compound: N-[2-(4-bromo-3-methyl-phenyl)-benzooxazol-5-yl]-acetamide.

Nucleic Acid Constructs

Nucleic Acid Constructs Containing a Minigene

The present invention provides for a nucleic acid construct comprising a minigene, wherein the minigene comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN, wherein either a single adenine, thymine or cytosine residue is inserted after nucleic acid residue 48 of exon 7 of SMN2, or a single nucleotide is inserted after nucleic acid residue 45, 46, or 47 of exon 7 of SMN2, and (ii) a reporter gene fused in frame to the fragment of the nucleic acid residues of exon 8 of SMN, wherein the reporter gene does not have a start codon. In the nucleic acid constructs comprising minigenes provided herein, the fragment of the nucleic acid residues of exon 8 in the minigenes cannot contain a stop codon.

In some embodiments, the minigene has a start codon (e.g., ATG or a non-canonical start codon) added to the 5' end of exon 6 of SMN or a fragment thereof. In one embodiment, a single adenine, thymine or cytosine residue is inserted after nucleic acid residue 48 of exon 7 of SMN2. In an alternative embodiment, a single nucleotide residue is inserted after nucleic acid 45, 46 or 47 of exon 7 of SMN2. In one embodiment, the single nucleotide residue inserted after nucleic acid 45, 46 or 47 is adenine, thymine or cytosine. In another embodiment, the single nucleotide residue inserted after nucleic acid 45, 46 or 47 is guanine.

In one embodiment, the nucleic acid construct comprises a minigene, wherein the minigene comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, and a fragment of the nucleic acid residues of exon 8 of SMN, wherein either a single adenine, thymine or cytosine residue is inserted after nucleic acid residue 48 of exon 7 of SMN2, or a single nucleotide is inserted after nucleic acid residue 45, 46, or 47 of exon 7 of SMN2, and (ii) a reporter gene fused in frame to a fragment of the nucleic acid residues of exon 8 of SMN, wherein the reporter gene does not have a start codon.

In a specific embodiment, the invention provides for a nucleic acid construct comprising a minigene, wherein the minigene comprises, in 5' to 3' order: (i) a start codon, the nucleic acid residues of exon 6 of SMN, the nucleic acid residues of intron 6 of SMN, the nucleic acid residues of exon 7 of SMN2, the nucleic acid residues of intron 7 of SMN, and the first 23 nucleic acid residues of exon 8, wherein a single adenine, thymine or cytosine residue is inserted after nucleic acid residue 48 of exon 7 of SMN2, and (ii) a reporter gene fused in frame to the 23 nucleic acid residues of exon 8 of SMN, wherein the reporter gene does not have a start codon.

In a specific embodiment, the invention provides for a nucleic acid construct comprising a minigene, wherein the minigene comprises, in 5' to 3' order: (i) a start codon, the nucleic acid residues of exon 6 of SMN, the nucleic acid residues of intron 6 of SMN, the nucleic acid residues of exon 7 of SMN2, the nucleic acid residues of intron 7 of SMN, and the first 21 nucleic acid residues of exon 8, wherein a single adenine, thymine or cytosine residue is inserted after nucleic acid residue 48 of exon 7 of SMN2, and (ii) a reporter gene fused in frame to the 23 nucleic acid residues of exon 8 of SMN, wherein the reporter gene does not have a start codon.

In another specific embodiment, the nucleic acid construct comprises a minigene, wherein the minigene comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2. In one aspect, the minigene comprises a start codon 5' to the nucleic acid residues of exon 6 of SMN, wherein the first codon of the coding sequence of the reporter gene and the start codon of the minigene are in the same open reading frame.

In another specific embodiment, the nucleic acid construct comprises a minigene, wherein the minigene comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first start codon of the fragment of the nucleic acid residues of exon 6 of SMN and the first codon of the coding sequence of the reporter gene are in the same open reading frame.

In another specific embodiment, the nucleic acid construct comprises a minigene, wherein the minigene comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first codon of the coding sequence of the reporter gene and the first start codon of the minigene are in the same open reading frame.

In another specific embodiment, the nucleic acid construct comprises a minigene, wherein the minigene comprises, in 5' to 3' order: nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first amino acid sequence include a start codon; (iii) the nucleic acid residues encoding the first and second amino acid sequences permit removal of an intron via mRNA splicing, and (iv) the first codon of the coding sequence of the reporter gene and the start codon of the nucleic acid residues encoding the first amino acid sequence are in the same open reading frame.

In another specific embodiment, the nucleic acid construct comprises a minigene, wherein the minigene comprises, in 5' to 3' order: a start codon, nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first and second amino acid sequences permit removal of an intron via mRNA splicing, and (iii) the first codon of the coding sequence of the reporter gene and the first start codon of the minigene are in the same open reading frame. In certain embodiments, the nucleic acid sequences encoding the first and second amino acid sequence are identical. In other embodiments, the first and second amino acid sequences encoded by the first and second nucleic acid sequences are identical. Those of skill in the art will understand that, due to the degeneracy of the genetic code, different nucleic acid sequences can code for the identical amino acid sequence.

The present invention also provides a nucleic acid construct comprising a minigene, wherein the minigene comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN, wherein a single guanine residue is inserted after nucleic acid residue 48 of exon 7 of SMN2, and (ii) a reporter gene fused in frame to a fragment of the nucleic acid residues of exon 8 of SMN, wherein the reporter gene does not have a start codon. In some embodiments, the minigene has a start codon (e.g., ATG or a non-canonical start codon) added to the 5' end of exon 6 of SMN or a fragment thereof. In certain embodiments, the minigene comprises a fragment of exon 8 of SMN having a number of nucleic acid residues other than 21 from the 5'-terminus. In some embodiments, the fragment is composed of more than the first 21 nucleotides of exon 8 of SMN. In other embodiments, the fragment is composed of less than the first 21 nucleotides of exon 8 of SMN.

The present invention also provides a nucleic acid construct comprising a minigene, wherein the minigene comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN, wherein a single guanine residue is inserted after nucleic acid residue 48 of exon 7 of SMN2, and (ii) a reporter gene fused in frame to a fragment of the nucleic acid residues of exon 8 of SMN, wherein the reporter gene does not have a start codon. In some embodiments, the minigene has a start codon (e.g., ATG or a non-canonical start codon) added to the 5' end of exon 6 of SMN or a fragment thereof. In certain embodiments, the minigene comprises a fragment of exon 8 of SMN having a number of nucleic acid residues other than 23 from the 5'-terminus. In some embodiments, the fragment is composed of more than the first 23 nucleotides of exon 8 of SMN. In other embodiments, the fragment is composed of less than the first 23 nucleotides of exon 8 of SMN.

In a specific embodiment, the nucleic acid construct comprises a minigene, wherein the minigene comprises, in 5' to 3' order: (i) a start codon, the nucleic acid residues of exon 6 of SMN2, the nucleic acid residues of intron 6 of SMN2, the nucleic acid residues of exon 7 of SMN2, the nucleic acid residues of intron 7 of SMN2, and the first 21 or 23 nucleic acid residues of exon 8 of SMN2, wherein a single guanine residue is inserted after nucleic acid residue 48 of exon 7 of SMN2, and (ii) a reporter gene (e.g., a luciferase reporter gene) fused in frame to the 21 or 23 nucleic acid residues of exon 8 of SMN2, wherein the reporter gene does not have a start codon.

In another specific embodiment, the nucleic acid construct comprises a minigene, wherein the minigene comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a reporter gene lacking a start codon, wherein a single guanine residue is inserted after nucleic acid residue 48 of exon 7 of SMN2. In one aspect, the minigene comprises a start codon 5' to the nucleic acid residues of exon 6 of SMN, wherein the first codon of the coding sequence of the reporter gene and the start codon of the minigene are in the same open reading frame.

In another specific embodiment, the nucleic acid construct comprises a minigene, wherein the minigene comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein a single guanine residue is inserted after nucleic acid residue 48 of exon 7 of SMN2, and wherein the first start codon of the fragment of the nucleic acid residues of exon 6 of SMN and the first codon of the coding sequence of the reporter gene are in the same open reading frame.

In another specific embodiment, the nucleic acid construct comprises a minigene, wherein the minigene comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein a single guanine residue is inserted after nucleic acid residue 48 of exon 7 of SMN2, and wherein the first codon of the coding sequence of the reporter gene and the first start codon of the minigene are in the same open reading frame.

In another specific embodiment, the nucleic acid construct comprises a minigene, wherein the minigene comprises, in 5' to 3' order: nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) wherein a single guanine residue is inserted after nucleic acid residue 48 of exon 7 of SMN2; (ii) the nucleic acid residues encoding the first amino acid sequence include a start codon; (iii) the nucleic acid residues encoding the first and second amino acid sequences permit removal of an intron via mRNA splicing, and (iv) the first codon of the coding sequence of the reporter gene and the start codon of the nucleic acid residues encoding the first amino acid sequence are in the same open reading frame.

In another specific embodiment, the nucleic acid construct comprises a minigene, wherein the minigene comprises, in 5' to 3' order: a start codon, nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) a single guanine residue is inserted after nucleic acid residue 48 of exon 7 of SMN2; (ii) the nucleic acid residues encoding the first and second amino acid sequences permit removal of an intron via mRNA splicing, and (iii) the first codon of the coding sequence of the reporter gene and the first start codon of the minigene are in the same open reading frame. In certain embodiments, the nucleic acid sequences encoding the first and second amino acid sequence are identical. In other embodiments, the first and second amino acid sequences encoded by the first and second nucleic acid sequences are identical. Those of skill in the art will understand that, due to the degeneracy of the genetic code, different nucleic acid sequences can code for the identical amino acid sequence.

In some embodiments, the nucleic acid residues of exon 6 or fragment thereof, the nucleic acid residues of intron 6 or a fragment thereof, the nucleic acid residues of intron 7 or a fragment thereof and/or a fragment of the nucleic acid residues of exon 8 are from the SMN1 gene. In other embodiments, the nucleic acid residues of exon 6 or a fragment thereof, the nucleic acid residues of intron 6 or a fragment thereof, the nucleic acid residues of intron 7 or a fragment thereof and/or a fragment of the nucleic acid residues of exon 8 are from the SMN2 gene.

In certain embodiments, the nucleic acid residues of exon 7 of SMN1 rather than the nucleic acid residues of exon 7 of SMN2 are used in a nucleic acid construct described herein. In some embodiments, a nucleic acid construct comprises a minigene, wherein the minigene comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN1 or a fragment thereof, the nucleic acid residues of intron 7 of SMN or a fragment thereof, and a fragment of the nucleic acid residues of exon 8 of SMN, wherein either a single adenine, thymine or cytosine residue is inserted after nucleic acid residue 48 of exon 7 of SMN1, or a single nucleotide is inserted after nucleic acid residue 45, 46, or 47 of exon 7 of SMN1, and (ii) a reporter gene fused in frame to the nucleic acid residues of exon 8 of SMN or a fragment thereof, wherein the reporter gene does not have a start codon. In some embodiments, the minigene has a start codon added to the 5' end of exon 6 of SMN or a fragment thereof.

In one specific embodiment, the nucleic acid construct comprises a minigene, wherein the minigene comprises, in 5' to 3' order: (i) a start codon, the nucleic acid residues of exon 6 of SMN2, the nucleic acid residues of intron 6 of SMN2, the nucleic acid residues of exon 7 of SMN1, the nucleic acid residues of intron 7 of SMN2, and the first 23 nucleic acid residues of exon 8 of SMN2, wherein a single adenine, thymine or cytosine residue is inserted after nucleic acid residue 48 of exon 7 of SMN1, and (ii) a reporter gene (e.g., a luciferase reporter gene) fused in frame to the first 23 nucleic acid residues of exon 8 of SMN2, wherein the reporter gene does not have a start codon.

In addition to the nucleic acid residues of exon 6 of SMN or a fragment thereof, the nucleic acid residues of intron 6 of SMN or a fragment thereof, the nucleic acid residues of exon 7 of SMN or a fragment thereof, the nucleic acid residues of intron 7 of SMN or a fragment thereof, a fragment of the nucleic acid residues of exon 8 of SMN and the reporter gene, the nucleic acid constructs may comprise one or more regulatory elements. In some embodiments, one or more of the transcriptional regulatory elements that are endogenous to SMN1 or SMN2 may be used to regulate the transcription of the minigene. In other embodiments, one or more transcriptional regulatory elements that are heterologous to SMN1 and/or SMN2 are used to control minigene transcription. Accordingly, any transcriptional regulatory element(s) known to those skilled in the art are intended to be included within the scope of the present invention for use in controlling transcription of the instant minigene. Non-limiting examples of the types of transcriptional regulatory element(s) include a constitutive promoter, a tissue-specific promoter or an inducible promoter. In a specific embodiment, the transcription of the minigene is controlled, at least in part, by one or more mammalian (in some embodiments, human) transcriptional regulatory element(s). In a specific embodiment, the transcription of the minigene is controlled, at least in part, by a strong promoter, such as CMV. The transcriptional regulatory elements may be operably linked to the minigene.

The nucleic acid constructs of the present invention may be part of or may be a vector that provides post-transcriptional regulatory elements and/or transcriptional regulatory elements. The vector chosen will depend upon a variety of factors, including, without limitation, the strength of the transcriptional regulatory elements and the host cell to be used to express the minigene.

In a specific embodiment, the nucleic acid construct comprises a promoter operably linked to the minigene, origins of replication from one or more species, and, optionally, one or more selectable markers (e.g., an antibiotic resistance gene), wherein the minigene comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN, wherein either a single adenine, thymine or cytosine residue is inserted after nucleic acid residue 48 of exon 7 of SMN2, or a single nucleotide is inserted after nucleic acid residue 45, 46 or 47 of exon 7 of SMN2, and (ii) a reporter gene fused in frame to a fragment of the nucleic acid residues of exon 8 of SMN, wherein the reporter gene does not have a start codon. In a specific embodiment, the nucleic acid construct is a CMV vector, such as pcDNA™ 3.1/Hygro (Invitrogen Corp., Carlsbad, Calif.). In other embodiments, the nucleic acid construct is a pT7 vector, a lac vector (e.g., a lac promoter-containing vector), a pCEP4 vector or a 5.0/FRT vector.

In a specific embodiment, the nucleic acid construct comprises a promoter operably linked to the minigene, origins of replication from one or more species, and, optionally, one or more selectable markers (e.g., an antibiotic resistance gene), wherein the minigene comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2. In one aspect, the minigene comprises a start codon 5' to the nucleic acid residues of exon 6 of SMN, wherein the first codon of the coding sequence of the reporter gene and the start codon of the minigene are in the same open reading frame.

In a specific embodiment, the nucleic acid construct comprises a promoter operably linked to the minigene, origins of replication from one or more species, and, optionally, one or more selectable markers (e.g., an antibiotic resistance gene), wherein the minigene comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first start codon of the fragment of the nucleic acid residues of exon 6 of SMN and the first codon of the coding sequence of the reporter gene are in the same open reading frame.

In a specific embodiment, the nucleic acid construct comprises a promoter operably linked to the minigene, origins of replication from one or more species, and, optionally, one or more selectable markers (e.g., an antibiotic resistance gene), wherein the minigene comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first codon of the coding sequence of the reporter gene and the first start codon of the minigene are in the same open reading frame.

In a specific embodiment, the nucleic acid construct comprises a promoter operably linked to the minigene, origins of replication from one or more species, and, optionally, one or more selectable markers (e.g., an antibiotic resistance gene), wherein the minigene comprises, in 5' to 3' order: nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first amino acid sequence include a start codon; (iii) the nucleic acid residues encoding the first and second amino acid sequences permit removal of an intron via mRNA splicing, and (iv) the first codon of the coding sequence of the reporter gene and the start codon of the nucleic acid residues encoding the first amino acid sequence are in the same open reading frame.

In a specific embodiment, the nucleic acid construct comprises a promoter operably linked to the minigene, origins of replication from one or more species, and, optionally, one or more selectable markers (e.g., an antibiotic resistance gene), wherein the minigene comprises, in 5' to 3' order: a start codon, nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first and second amino acid sequences permit removal of an intron via mRNA splicing, and (iii) the first codon of the coding sequence of the reporter gene and the first start codon of the minigene are in the same open reading frame.

In some embodiments, a nucleic acid construct described herein is isolated.

Reporter Genes

Any reporter gene well-known to one of skill in the art may be used in the nucleic acid constructs of the present invention to identify or validate whether a compound enhances the inclusion of exon 7 of SMN2 into mRNA transcribed from the SMN2 gene. Reporter genes refer to a nucleotide sequence encoding a protein that is readily detectable either by its presence or activity. Reporter genes may be obtained and the nucleotide sequence of the reporter gene determined by any method well-known to one of skill in the art. In certain embodiments, a nucleic acid sequence that codes for the coding sequence of a reporter gene is used in the nucleic acid constructs described herein. In some embodiments, a nucleic acid sequence that encodes a reporter gene is used in the nucleic acid constructs described herein.

Examples of reporter genes include, but are not limited to, nucleotide sequences encoding luciferase (e.g., firefly luciferase, *renilla* luciferase, genetically modified luciferase, and click beetle luciferase), green fluorescent protein ("GFP") (e.g., green fluorescent protein, yellow fluorescent protein, red fluorescent protein, cyan fluorescent protein, and blue fluorescent protein), beta-galactosidase ("β-gal"), beta-glucoronidase, beta-lactamase, chloramphenicol acetyltransferase ("CAT"), and alkaline phosphatase ("AP"). Commercially available vectors encoding reporter genes, e.g., luciferase, can be used to obtain the reporter genes (e.g., Chroma-Luc™ Vectors manufactured by Promega, Madison, Wis.).

In a specific embodiment, a reporter gene utilized in the nucleic acid constructs is easily detected and indicates an activity which is not normally found in the cell or organism of interest. In a specific embodiment, a reporter gene utilized in the instant nucleic acid constructs is not, per se, SMN1 or SMN2.

Cells and Transfection Techniques

A host cell may be transformed or transfected with a nucleic acid construct described herein. In one embodiment, the host cell is transiently transfected with a nucleic acid construct. In an alternative embodiment, the host cell is stably transfected with a nucleic acid construct. In certain embodiments, more than one nucleic acid construct may be transfected into a host cell. In one specific embodiment, the host cell is a mammalian cell. In another specific embodiment, the host cell is a human cell. In another embodiment, host cells are a cell line. In another embodiment, the host cells are primary cells isolated from a tissue or other biological sample of interest. Host cells that can be used in the methods of the present invention include, but are not limited to, hybridomas, pre-B cells, HEK293 cells, HEK293T cells, HEK293H cells, HeLa cells, HepG2 cells, K562 cells, NIH/3T3 cells, MCF7 cells, SkBr3 cells, BT474 cells, the human type I SMA fibroblast cells GM03813, GM09677, GM00232, or B lymphocyte GM10684, or neuroblastoma cells lines such as MC-IXC, SK-N-MC, SK-N-MC, SK-N-DZ, SH-SY5Y, and BE(2)-C. In one embodiment, the host cells are immortalized cell lines derived from a source, e.g., a tissue, specific to SMA. In one embodiment, the host cells are stem cells.

Transformation may be by any known method for introducing polynucleotides into a host cell. The transformation procedure used will depend upon the host to be transformed. Such methods are well-known to one of skill in the art.

In a specific embodiment, stable cell lines containing a nucleic acid construct of interest are generated for high throughput screening (HTS). Such stable cells lines may be generated by introducing a nucleic acid construct comprising a selectable marker, allowing the cells to grow for 1-2 days in an enriched medium, and then growing the cells on a selective medium. The selectable marker in the recombinant plasmid confers resistance to the selection and allows cells to stably integrate the plasmid into their chromosomes and grow to form foci which in turn can be cloned and expanded into cell lines.

In one embodiment, a cell is engineered to contain or comprise a nucleic acid construct comprising a minigene, wherein the minigene comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 or a fragment thereof, and a fragment of the nucleic acid residues of exon 8 of SMN, wherein either a single adenine, thymine or cytosine residue is inserted after nucleic acid residue 48 of exon 7 of SMN2, or a single nucleotide is inserted after nucleic acid residue 45, 46 or 47 of exon 7 of SMN2, and (ii) a reporter gene fused in frame to the nucleic acid residues of exon 8 of SMN or a fragment thereof, wherein the reporter gene does not have a start codon. In a specific embodiment, the minigene has a start codon added to the 5' end of the nucleic acid residues of exon 6 of SMN or a fragment thereof.

In another embodiment, a cell is engineered to contain or comprise a first nucleic acid construct and a second nucleic acid construct, wherein (a) the first nucleic acid construct comprises a first minigene, which comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN, wherein either a single adenine, thymine or cytosine residue is inserted after nucleic acid residue 48 of exon 7 of SMN2, or a single nucleotide is inserted after nucleic acid residue 45, 46, or 47 of exon 7 of SMN2, and (ii) a first reporter gene fused in frame to a fragment of the nucleic acid residues of exon 8 of SMN, wherein the first reporter gene does not have a start codon; and wherein (b) the second nucleic acid construct comprises a second minigene which comprises, in 5' to 3' order, (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN, wherein a single guanine residue is inserted after nucleic acid residue 48 of exon 7 of SMN2, and (ii) a second reporter gene fused in frame to a fragment of the nucleic acid residues of exon 8 of SMN, wherein the second reporter gene does not have a start codon. In one specific embodiment, the first minigene and the second minigene have a start codon added to the 5' end of the nucleic acid residues of exon 6 of SMN or a fragment thereof. In another specific embodiment, the first and the second reporter genes are different. In a specific embodiment, the fragment of the nucleic acid residues of exon 8 comprises the first 21 or 23 nucleic acid residues of exon 8.

In another embodiment, a cell is engineered to contain or comprise a first nucleic acid construct a second nucleic acid construct, wherein (a) the first nucleic acid construct comprises a first minigene which comprises, in 5' to 3' order: (i) a start codon, the nucleic acid residues of exon 6 of SMN or a fragment thereof, the nucleic acid residues of intron 6 of SMN, the nucleic acid residues of exon 7 of SMN2, the nucleic acid residues of intron 7 of SMN, and the first 23 nucleic acid residues of exon 8 of SMN, wherein either a single adenine, thymine or cytosine residue is inserted after nucleic acid residue 48 of exon 7 of SMN2, or a single nucleotide is inserted after nucleic acid residue 45, 46 or 47 of exon 7 of SMN2, and (ii) a first reporter gene fused to the 23 nucleic acid residues of exon 8 of SMN, wherein the first reporter gene does not have a start codon; and wherein (b) the second nucleic acid construct comprises a second minigene which comprises, in 5' to 3' order: (i) a start codon, the nucleic acid residues of exon 6 of SMN or a fragment thereof, the nucleic acid residues of intron 6 of SMN, the nucleic acid residues of exon 7 of SMN2, the nucleic acid residues of intron 7 of SMN, and the 23 nucleic acid residues of exon 8 of SMN, wherein a single guanine residue is inserted after nucleic acid residue 48 of exon 7 of SMN2, and (ii) a second reporter gene fused in frame to the first 23 nucleic acid residues of exon 8 of SMN, wherein the second reporter gene does not have a start codon.

In another embodiment, a cell is engineered to contain or comprise a first nucleic acid construct and a second nucleic acid construct, wherein (a) the first nucleic acid construct comprises a first minigene which comprises, in 5' to 3' order: (i) the nucleic acid residues of exon 6 of SMN or a fragment thereof, the nucleic acid residues of intron 6 of SMN, the nucleic acid residues of exon 7 of SMN2, the nucleic acid residues of intron 7 of SMN, and the first 21 nucleic acid residues of exon 8 of SMN, wherein either a single adenine, thymine or cytosine residue is inserted after nucleic acid residue 48 of exon 7 of SMN2, or a single nucleotide is inserted after nucleic acid residue 45, 46 or 47 of exon 7 of SMN2, and (ii) a first reporter gene fused in frame to the 21 nucleic acid residues of exon 8 of SMN, wherein the first reporter gene does not have a start codon; and wherein (b) the second nucleic acid construct comprises a second minigene which comprises, in 5' to 3' order: (i) the nucleic acid residues of exon 6 of SMN or a fragment thereof, the nucleic acid residues of intron 6 of SMN, the nucleic acid residues of exon 7 of SMN2, the nucleic acid residues of intron 7 of SMN, and the first 21 nucleic acid residues of exon 8 of SMN, wherein a single guanine residue is inserted after nucleic acid residue 48 of exon 7 of SMN2, and (ii) a second reporter gene fused in frame to the 21 nucleic acid residues of exon 8 of SMN, wherein the second reporter gene does not have a start codon. In one specific embodiment, the first minigene and the second minigene have a start codon added to the 5' end of the nucleic acid residues of exon 6 of SMN or a fragment thereof. In another specific embodiment, the first and second reporter genes are different.

In another embodiment, a cell is engineered to contain or comprise a nucleic acid construct comprising a minigene, wherein the minigene comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2. In one aspect, the minigene comprises a start codon 5' to the nucleic acid residues of exon 6 of SMN, wherein the first codon of the coding sequence of the reporter gene and the start codon of the minigene are in the same open reading frame.

In another embodiment, a cell is engineered to contain or comprise a nucleic acid construct comprising a minigene, wherein the minigene comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first start codon of the fragment of the nucleic acid residues of exon 6 of SMN and the first codon of the coding sequence of the reporter gene are in the same open reading frame.

In another embodiment, a cell is engineered to contain or comprise a nucleic acid construct comprising a minigene, wherein the minigene comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first codon of the coding sequence of the reporter gene and the first start codon of the minigene are in the same open reading frame.

In another embodiment, a cell is engineered to contain or comprise a nucleic acid construct comprising a minigene, wherein the minigene comprises, in 5' to 3' order: nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first amino acid sequence include a start codon; (iii) the nucleic acid residues encoding the first and second amino acid sequences permit removal of an intron via mRNA splicing, and (iv) the first codon of the coding sequence of the reporter gene and the start codon of the nucleic acid residues encoding the first amino acid sequence are in the same open reading frame.

In another embodiment, a cell is engineered to contain or comprise a nucleic acid construct comprising a minigene, wherein the minigene comprises, in 5' to 3' order: a start codon, nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first and second amino acid sequences permit removal of an intron via mRNA splicing, and (iii) the first codon of the coding sequence of the reporter gene and the first start codon of the minigene are in the same open reading frame.

Screening Assays
Cell-Based Assays

Host cells transformed or transfected with a nucleic acid construct described herein are used to identify or validate compounds that modulate inclusion of exon 7 of SMN2 into mRNA transcribed from the SMN2 gene, and thus modulate the levels of SMN protein produced from the SMN2 gene. In a specific embodiment, the host cells are stably transfected with a nucleic acid construct.

In one embodiment, the present invention includes a method for the identification of a compound that modulates inclusion of exon 7 of SMN2 into mRNA transcribed from the SMN2 gene comprising the steps of: (a) contacting a compound with a host cell containing a nucleic acid construct comprising a minigene, wherein the minigene comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN, wherein either a single adenine, thymine or cytosine residue is inserted after nucleic acid residue 48 of exon 7 of SMN2, or a single nucleotide is inserted after nucleic acid residue 45, 46, or 47 of exon 7 of SMN2, and (ii) a reporter gene fused in frame to a fragment of the nucleic acid residues of exon 8 of SMN, wherein the reporter gene does not have a start codon; and (b) measuring the activity of a fusion protein expressed from the minigene. In a specific embodiment, the minigene has a start codon added to the 5' end of the nucleic acid residues of exon 6 of SMN or a fragment thereof. A change in the activity of the fusion protein expressed by host cell in the presence of the compound compared to (i) a previously determined reference range; or (ii) the activity of the fusion protein expressed by the host cell in the absence of the compound in such an assay; or (iii) the activity of the fusion protein expressed by host cell in the presence of a negative control in such an assay indicates that a particular compound modulates inclusion of exon 7 of SMN2 into mRNA transcribed from the SMN2 gene. In a specific embodiment, the change in the activity of the fusion protein is a significant alteration.

A compound that increases the inclusion of exon 7 of SMN2 into mRNA transcribed from the SMN2 gene, and thus increases levels of SMN protein produced from the SMN2 gene, will result in an increase in the activity of a fusion protein expressed by the host cell compared (i) to the activity of the fusion protein expressed by the host cell in the absence of the compound, and/or compared (ii) to the activity of the fusion protein expressed by the host cell in the presence of a negative control, and/or (iii) a previously determined reference range for a negative control.

In contrast, a compound that does not increase the inclusion of exon 7 of SMN2 into mRNA transcribed from the SMN2 gene will not significantly alter the level of activity of the fusion protein expressed by the host cell compared to (i) the level of activity of the fusion protein expressed by the host cell in the absence of the compound, (ii) the level of activity of fusion protein expressed by the host cell in the presence of a negative control, and/or (iii) a previously determined reference range for a negative control.

In some embodiments, in addition to, or as an alternative to, detecting the activity of the fusion protein encoded by the minigene, the amount of the fusion protein can be detected. In accordance with such embodiments, a change in the amount of the fusion protein expressed by the host cell in the presence of the compound when compared to (i) a previously determined reference range for a negative control, (ii) the amount of the fusion protein expressed by the host cell in the absence of the compound in such an assay, and/or (iii) the amount of the fusion protein expressed by the host cell in the presence of a negative control in such an assay indicates that a particular compound modulates inclusion of exon 7 of SMN2 into mRNA transcribed from the SMN2 gene. In a specific embodiment, the change in the amount of the fusion protein is a significant alteration.

A compound that increases the inclusion of exon 7 of SMN2 into mRNA transcribed from the SMN2 gene, and thus increases levels of SMN protein produced from the SMN2 gene, will result in an increase in the amount of the fusion protein expressed by the host cell compared (i) the amount of the fusion protein when the host cell is not contacted with the compound, (ii) compared with the amount of the fusion protein when the host cell is contacted with a negative control, and/or (iii) a previously determined reference range for a negative control.

In contrast, a compound that does not increase the inclusion of exon 7 of SMN2 into mRNA transcribed from the SMN2 gene will not significantly alter the amount of the fusion protein expressed by the host cell compared to (i) the amount of the fusion protein expressed by the host cell in the absence of the compound, (ii) the amount of fusion protein expressed by the host cell in the presence of a negative control, and/or (iii) a previously determined reference range for a negative control.

In another embodiment, an assay of the present invention includes a method for the identification of a compound that increases the inclusion of exon 7 of SMN2 into mRNA transcribed from the SMN2 gene comprising the steps of: (a) contacting a compound with a host cell containing a nucleic acid construct comprising a minigene, wherein the minigene comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; and (b) detecting the activity or amount of a fusion protein encoded by the minigene, wherein an increase in the activity or amount of the fusion protein expressed by the host cell in the presence of the compound relative to the activity or amount of the fusion protein expressed by the host cell in the absence of the compound or the presence of a negative control compound, or relative to a previously determined reference range indicates that the compound increases the inclusion of exon 7 of SMN2 into mRNA transcribed from the SMN2 gene. In one aspect, the minigene comprises a start codon 5' to the nucleic acid residues of exon 6 of SMN, wherein the first codon of the coding sequence of the reporter gene and the start codon of the minigene are in the same open reading frame.

In another embodiment, an assay of the present invention includes a method for the identification of a compound that increases the inclusion of exon 7 of SMN2 into mRNA transcribed from the SMN2 gene comprising the steps of: (a) contacting a compound with a host cell containing a nucleic acid construct comprising a minigene, wherein the minigene comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first start codon of the fragment of the nucleic acid residues of exon 6 of SMN and the first codon of the coding sequence of the reporter gene are in the same open reading frame; and (b) detecting the activity or amount of a fusion protein encoded by the minigene, wherein an increase in the activity or amount of the fusion protein expressed by the host cell in the presence of the compound relative to the activity or amount of the fusion protein expressed by the host cell in the absence of the compound or the presence of a negative control compound, or relative to a previously determined reference range indicates that the compound increases the inclusion of exon 7 of SMN2 into mRNA transcribed from the SMN2 gene.

In another embodiment, an assay of the present invention includes a method for the identification of a compound that increases the inclusion of exon 7 of SMN2 into mRNA transcribed from the SMN2 gene comprising the steps of: (a) contacting a compound with a host cell containing a nucleic acid construct comprising a minigene, wherein the minigene comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first codon of the coding sequence of the reporter gene and the first start codon of the minigene are in the same open reading frame; and (b) detecting the activity or amount of a fusion protein encoded by the minigene, wherein an increase in the activity or amount of the fusion protein expressed by the host cell in the presence of the compound relative to the activity or amount of the fusion protein expressed by the host cell in the absence of the compound or the presence of a negative control compound, or relative to a previously determined reference range indicates that the compound increases the inclusion of exon 7 of SMN2 into mRNA transcribed from the SMN2 gene.

In another embodiment, an assay of the present invention includes a method for the identification of a compound that increases the inclusion of exon 7 of SMN2 into mRNA transcribed from the SMN2 gene comprising the steps of: (a) contacting a compound with a host cell containing a nucleic acid construct comprising a minigene, wherein the minigene comprises, in 5' to 3' order: nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first amino acid sequence include a start codon; (iii) the nucleic acid residues encoding the first and second amino acid sequences permit removal of an intron via mRNA splicing, and (iv) the first codon of the coding sequence of the reporter gene and the start codon of the nucleic acid residues encoding the first amino acid sequence are in the same open reading frame; and (b) detecting the activity or amount of a fusion protein encoded by the minigene, wherein an increase in the activity or amount of the fusion protein expressed by the host cell in the presence of the compound relative to the activity or amount of the fusion protein expressed by the host cell in the absence of the compound or the presence of a negative control compound, or relative to a previously determined reference range indicates that the compound increases the inclusion of exon 7 of SMN2 into mRNA transcribed from the SMN2 gene.

In another embodiment, an assay of the present invention includes a method for the identification of a compound that increases the inclusion of exon 7 of SMN2 into mRNA transcribed from the SMN2 gene comprising the steps of: (a) contacting a compound with a host cell containing a nucleic acid construct comprising a minigene, wherein the minigene comprises, in 5' to 3' order: a start codon, nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first and second amino acid sequences permit removal of an intron via mRNA splicing, and (iii) the first codon of the coding sequence of the reporter gene and the first start codon of the minigene are in the same open reading frame; and (b) detecting the activity or amount of a fusion protein encoded by the minigene, wherein an increase in the activity or amount of the fusion protein expressed by the host cell in the presence of the compound relative to the activity or amount of the fusion protein expressed by the host cell in the absence of the compound or the presence of a negative control compound, or relative to a previously determined reference range indicates that the compound increases the inclusion of exon 7 of SMN2 into mRNA transcribed from the SMN2 gene.

In some embodiments, in addition to, or as alternative to, detecting the amount and/or activity of the fusion protein, the amount of mRNA transcript containing exon 7 of SMN2 or a fragment thereof transcribed from the minigene can be detected. In accordance with such embodiments, a change in the amount of the mRNA containing exon 7 of SMN2 or a fragment thereof transcript transcribed from the minigene when the cell is contacted with the compound compared to a previously determined reference range, the amount of mRNA transcript containing exon 7 of SMN2 or a fragment thereof transcribed from the minigene when the host cell is not contacted with the compound, and/or the amount of mRNA transcript containing exon 7 of SMN2 or a fragment thereof transcribed from the minigene when the host cell is contacted with a negative control. In a specific embodiment, the change in the amount of mRNA transcript containing exon 7 of SMN2 or a fragment thereof is a significant alteration. A compound that increases the inclusion of the complete, intact, non-truncated sequence of exon 7 of SMN2 into mRNA transcribed from the SMN2 gene will have an increased amount of mRNA transcript containing exon 7 of SMN2 or a fragment thereof transcribed from the minigene when compared to a previously determined reference range for a negative control, the amount of mRNA transcript containing exon 7 of SMN2 or a fragment thereof transcribed from the minigene when the host cell is not contacted with the compound, and/or the amount of mRNA transcript containing exon 7 of SMN2 or a fragment thereof transcribed from the minigene when the host cell is contacted with a negative control. In contrast, a compound that does not increase the inclusion of exon 7 of SMN2 into mRNA transcribed from the SMN2 gene will not significantly alter the amount of mRNA transcript containing exon 7 of SMN2 or a fragment thereof transcribed from the minigene compared to the amount of mRNA transcript containing exon 7 of SMN2 or a fragment thereof transcribed from the minigene when the host cell is not contacted with the compound, the amount of mRNA transcript containing exon 7 of SMN2 or a fragment thereof transcribed from the minigene when the host cell is contacted with a negative control and/or a previously determined reference range for a negative control.

In one specific embodiment, a negative control (e.g., DMSO at 0.5-1.0%, or PBS, or another agent that is known to have no effect on the expression of the reporter gene) and a positive control (e.g., an agent that modulates exon 7 splicing of SMN2) are included in the cell-based assays described herein.

In certain embodiments, to generate a positive control construct, those nucleic acid constructs described herein which recite the insertion of a single adenine, thymine, or cytosine residue after nucleic acid residue 48 of the nucleic acid residues of exon 7 of SMN2, or the insertion of a single nucleotide after nucleic acid residue 45, 46, or 47 of the nucleic acid residues of exon 7 of SMN2, use the nucleic acid residues of exon 7 of SMN1 in place of the nucleic acid residues of exon 7 of SMN2. In one specific embodiment, a nucleic acid construct may be used as a positive control for the cell-based assays described herein, wherein the method for validating that a compound modulates the inclusion of exon 7 of SMN2 into mRNA transcribed from the SMN2 gene comprises contacting the compound with a host cell containing a positive control nucleic acid construct comprising a minigene, wherein the minigene comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN1 or a fragment thereof, the nucleic acid residues of intron 7 of SMN or a fragment thereof, and a fragment of the nucleic acid residues of exon 8 of SMN, wherein either a single adenine, thymine or cytosine residue is inserted after nucleic acid residue 48 of exon 7 of SMN1, or a single nucleotide is inserted after nucleic acid residue 45, 46 or 47 of exon 7 of SMN1; and (ii) a reporter gene fused in frame to the nucleic acid residues of exon 8 of SMN or a fragment thereof, wherein the reporter gene does not have a start codon. In a specific embodiment, the minigene has a start codon added to the 5' end of exon 6 of SMN or a fragment thereof. The mRNA transcript transcribed from the minigene will contain, in part, the complete, intact, non-truncated sequence of exon 7 of SMN1 regardless of whether or not the host cell is contacted with a compound. Thus, the fusion protein encoded by the minigene will be detectable in the presence or absence of a compound.

In another specific embodiment, a nucleic acid construct may be used as a positive control for the cell-based assays described herein, wherein the method for validating that a compound modulates the inclusion of exon 7 of SMN2 into mRNA transcribed from the SMN2 gene comprises contacting the compound with a host cell containing a positive control nucleic acid construct comprising a minigene, wherein the minigene comprises, in 5' to 3' order: a start codon, the nucleic acid residues of exon 6 SMN, the nucleic acid residues of intron 6 of SMN, the nucleic acid residues of exon 7 of SMN1, the nucleic acid residues of intron 7 of SMN, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN1, or a single nucleotide is inserted after nucleic acid residue 45, 46 or 47 of exon 7 of SMN1, and wherein the first codon of the coding sequence of the reporter gene and the start codon of the minigene are in the same open reading frame.

In certain embodiments, to generate a negative control construct, a single guanine is inserted after nucleic acid residue 48 of the nucleic acid residues of exon 7 of SMN2 in a nucleic acid construct described herein as opposed to the insertion of a single adenine, thymine, or cytosine residue inserted after nucleic acid residue 48 of the nucleic acid residues of exon 7 of SMN2 or a single nucleotide inserted after nucleic residue 45, 46, or 47 of the nucleic acid residues of exon 7 of SMN2. In one specific embodiment, a nucleic acid construct may be used as a negative control for the cell-based assays described herein, wherein the method for validating that a compound modulates the inclusion of exon 7 of SMN2 into mRNA transcribed from the SMN2 gene comprises contacting the compound with a host cell containing a negative control nucleic acid construct comprising a minigene, wherein the minigene comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 or a fragment thereof, and a fragment of the nucleic acid residues of exon 8 of SMN, wherein a guanine is inserted after nucleic acid residue 48 of exon 7 of SMN2, and (ii) a reporter gene fused in frame to the nucleic acid residues of exon 8 of SMN or a fragment thereof, wherein the reporter gene does not have a start codon. In a specific embodiment, the minigene has a start codon added to the 5' end of the nucleic acid residues of exon 6 of SMN or a fragment thereof. This host cell can be used as a negative control to exclude compounds that do not increase the inclusion of exon 7 of SMN2 into mRNA transcribed from the SMN2 gene.

In another specific embodiment, a nucleic acid construct may be used as a negative control for the cell-based assays described herein, wherein the method for validating that a compound modulates the inclusion of exon 7 of SMN2 into mRNA transcribed from the SMN2 gene comprises contacting the compound with a host cell containing a negative control nucleic acid construct comprising a minigene, wherein the minigene comprises, in 5' to 3' order: a start codon, the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a reporter gene lacking a start codon, wherein a guanine is inserted after nucleic acid residue 48 of exon 7 of SMN2, and wherein the first codon of the coding sequence of the reporter gene and the start codon of the minigene are in the same open reading frame.

In a specific embodiment, the host cell used as a negative control in a cell-based assay contains a nucleic acid construct comprising a minigene, wherein the minigene comprises, in 5' to 3' order: (i) a start codon, the nucleic acid residues of exon 6 of SMN2, the nucleic acid residues of intron 6 of SMN2, the nucleic acid residues of exon 7 of SMN2, the nucleic acid residues of intron 7 of SMN2, and the first 23 nucleic acid residues of exon 8 of SMN2, wherein a guanine is inserted after nucleic acid residue 48 of exon 7 of SMN2, and (ii) a reporter gene (e.g., luciferase reporter gene) fused in frame to the 23 nucleic acid residues of exon 8 of SMN or a fragment thereof, wherein the reporter gene does not have a start codon.

In certain embodiments, the host cell used as a negative control in a cell-based assay contains a nucleic acid construct comprising a minigene, wherein the minigene comprises, in 5' to 3' order: (i) the nucleic acid residues of exon 6 of SMN2, the nucleic acid residues of intron 6 of SMN2, the nucleic acid residues of exon 7 of SMN2, the nucleic acid residues of intron 7 of SMN2, and the first 21 nucleic acid residues of exon 8 of SMN2, wherein a guanine is inserted after nucleic acid residue 48 of exon 7 of SMN2, and (ii) a reporter gene (e.g., a luciferase reporter gene) fused in frame to the 21 nucleic acid residues of exon 8 of SMN, wherein the reporter gene does not have a start codon.

The step of contacting a compound with a host cell containing the nucleic acid construct may be conducted under conditions approximating or mimicking physiologic conditions. In a specific embodiment, a compound is added to the cells in the presence of an appropriate growth medium for said cells. In another embodiment, a compound is added to the cells in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but not limited to, KCl, NaCl, and/or $MgCl_2$. The optimal concentration of each salt used in the aqueous solution is dependent on the host cells and compounds used and can be determined using routine experimentation.

A compound is contacted with a host cell containing the nucleic acid construct for a specific period of time. For example, the compound may be contacted with the host cell containing the nucleic acid construct for a time period of about 1 minute, 2 minutes, 3 minutes, 4, minutes, 5, minutes, 10 minutes, 15 minutes, 20 minutes, 30 minutes, 1 hour, 2 hours, 3 hours, 4 hours, 5 hours, 10 hours, 15 hours, 20 hours, 1 day, 2 days, 3 days, 4 days, 5 days, or 1 week. In a specific embodiment, contact is over a time period of about 12 hours to about 15 hours, or about 14 hours to about 18 hours, i.e., overnight.

In one embodiment, a method for identifying a compound that modulates inclusion of exon 7 of SMN2 into mRNA transcribed from the SMN2 gene comprises the steps of: (a) expressing in a host cell a nucleic acid construct comprising a minigene, wherein the minigene comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN, wherein either a single adenine, thymine or cytosine residue is inserted after nucleic acid residue 48 of exon 7 of SMN2, or a single nucleotide is inserted after nucleic acid residue 45, 46 or 47 of exon 7 of SMN2, and (ii) a reporter gene fused in frame to the nucleic acid residues of exon 8 of SMN or a fragment thereof, wherein the reporter gene does not have a start codon; (b) contacting said host cell with a compound; and (c) detecting the activity of the fusion protein encoded by the minigene, wherein a compound that modulates inclusion of exon 7 of SMN2 into mRNA transcribed from the SMN2 gene is identified if the activity of the fusion protein expressed by the host cell in the presence of a compound is altered relative to a previously determined reference range, or relative to the activity of the fusion protein expressed by the host cell in the absence of said compound or the presence of a negative control (e.g., PBS or DMSO). In a specific embodiment, the alteration in the activity of the fusion protein is a significant alteration.

In some embodiments, in addition to, or as an alternative to, detecting the activity of the fusion protein, the amount of the fusion protein can be detected. In accordance with such embodiments, a compound that modulates inclusion of exon 7 of SMN2 into mRNA transcribed from SMN2 gene is identified if the amount of the fusion protein expressed by the host cell in the presence of a compound is altered relative to a previously determined reference range, or relative to the amount of the fusion protein expressed by the host cell in the absence of the compound or the presence of a negative control.

In accordance with the foregoing embodiments, a previously determined reference range would be the amount and/or activity of the fusion protein obtained for a negative control. In a specific embodiment, the minigene has a start codon added to the 5' end of exon 6 of SMN or a fragment thereof.

In some embodiments, in addition to, or as an alternative to, detecting the amount and/or activity of the fusion protein, the amount of mRNA containing exon 7 of SMN2 or a fragment thereof transcribed from the minigene can be detected. In accordance with such embodiments, a compound that modulates inclusion of exon 7 of SMN2 into mRNA transcribed from the SMN2 gene is identified if the compound alters the amount of a mRNA transcript containing exon 7 of SMN2 or a fragment thereof transcribed from the minigene relative to a previously determined reference range or the amount of such a mRNA transcript containing exon 7 of SMN2 or a fragment thereof in the absence of the compound or the presence of a negative control.

In a specific embodiment, the present invention includes a method for identifying a compound that increases the inclusion of exon 7 of SMN2 into mRNA transcribed from the SMN2 gene comprising the steps of: (a) contacting a compound with a host cell expressing a nucleic acid construct comprising a minigene, wherein the minigene comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN, wherein either a single adenine, thymine or cytosine residue is inserted after nucleic acid residue 48 of exon 7 of SMN2, or a single nucleotide is inserted after nucleic acid residue 45, 46, or 47 of exon 7 of SMN2, and (ii) a reporter gene fused in frame to the nucleic acid residues of exon 8 of SMN or a fragment thereof, wherein the reporter gene does not have a start codon; and (b) detecting the amount or activity of the fusion protein encoded by the minigene, wherein a compound that increases the inclusion of exon 7 of SMN2 into mRNA transcribed from the SMN2 gene is identified if the amount or activity of the fusion protein expressed by the host cell in the presence of the compound is increased relative to a previously determined reference range, or relative to the amount or activity of the fusion protein when the host cell is not contacted with the compound, or relative to the activity of the fusion protein when the host cell is contacted with a negative control (e.g., PBS or DMSO). In a specific embodiment, the minigene has a start codon added to the 5' end of exon 6 of SMN or a fragment thereof. In accordance with these embodiments, a previously determined reference range would be the amount or activity obtained for a negative control. In some embodiments, both the amount and activity of the fusion protein are detected.

In some embodiments, the present invention includes a method for identifying a compound that increases the inclusion of exon 7 of SMN2 into mRNA transcribed from the SMN2 gene comprising the steps of: (a) contacting a compound with a host cell expressing a nucleic acid construct comprising a minigene, wherein the minigene comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, and the nucleic acid residues of intron 7 of SMN or a fragment thereof, and a fragment of the nucleic acid residues of exon 8 of SMN, wherein either a single adenine, thymine or cytosine residue is inserted after nucleic acid residue 48 of exon 7 of SMN2, or a single nucleotide is inserted after nucleic acid residue 45, 46 or 47 or exon 7 of SMN2, and (ii) a reporter gene fused in frame to the nucleic acid residues of exon 8 of SMN or a fragment thereof, wherein the reporter gene does not have a start codon; and (b) detecting the amount or activity of the fusion protein encoded by the minigene, wherein a compound that increases the inclusion of exon 7 of SMN2 into mRNA transcribed from the SMN2 gene is identified if the amount or activity of the fusion protein when the host cell is contacted with the compound is greater than the amount or activity of the fusion protein obtained when a negative control is contacted with the host cell, and/or equivalent or not significantly lower (e.g., not less than 25%, 15%, 10% or 5% lower) than the amount or activity of the fusion protein obtained when a positive control is contacted with the host cell. In a specific embodiment, the minigene has a start codon added to the 5' end of the nucleic acid residues of exon 6 of SMN or a fragment thereof. In some embodiments, both the amount and activity of the fusion protein are detected.

In a specific embodiment, the present invention includes a method for identifying a compound that increases the inclusion of exon 7 of SMN2 into mRNA transcribed from the SMN2 gene comprising the steps of: (a) contacting a compound with a host cell expressing a nucleic acid construct comprising a minigene, wherein the minigene comprises, in 5' to 3' order: (i) a start codon, the nucleic acid residues of exon 6 of SMN, the nucleic acid residues of intron 6 of SMN, the nucleic acid residues of exon 7 of SMN2, the nucleic acid residues of intron 7 of SMN and the first 23 nucleic acid residues of exon 8 of SMN, wherein a single adenine, thymine or cytosine residue is inserted after nucleic acid residue 48 of exon 7 of SMN2, and (ii) a luciferase reporter gene fused in frame to the 23 nucleic acid residues of exon 8 of SMN, wherein the luciferase reporter gene does not have a start codon; and (b) detecting the luciferase reporter activity, wherein a compound that increases the inclusion of exon 7 of SMN2 into mRNA transcribed from the SMN2 gene is identified if the luciferase reporter activity expressed by the host cell in the presence of a compound is increased relative to activity of the luciferase expressed by the host cell in the presence of 0.5%-1% DMSO.

In certain embodiments, the present invention includes a method for identifying a compound that increases the inclusion of exon 7 of SMN2 into mRNA transcribed from the SMN2 gene comprising the steps of: (a) contacting a compound with a host cell expressing a nucleic acid construct comprising a minigene, wherein the minigene comprises, in 5' to 3' order: (i) the nucleic acid residues of exon 6 of SMN, the nucleic acid residues of intron 6 of SMN, the nucleic acid residues of exon 7 of SMN2, the nucleic acid residues of intron 7 of SMN and the first 21 nucleic acid residues of exon 8 of SMN, wherein a single adenine, thymine or cytosine residue is inserted after nucleic acid residue 48 of exon 7 of SMN2, and (ii) a luciferase reporter gene fused in frame to the 21 nucleic acid residues of exon 8 of SMN, wherein the luciferase reporter gene does not have a start codon; and (b) detecting the luciferase reporter activity, wherein a compound that increases the inclusion of exon 7 of SMN2 into mRNA transcribed from the SMN2 gene is identified if the luciferase reporter activity in the presence of a compound is increased relative to the activity of the luciferase reporter gene in the presence of 0.5%-1% DMSO.

In another embodiment, the present invention includes a method for identifying and validating a compound that modulates inclusion of exon 7 of SMN2 into mRNA transcribed from the SMN2 gene comprising the steps of: (a) contacting a first concentration of a compound with a first host cell containing a first nucleic acid construct comprising a first minigene which comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN, wherein either a single adenine, thymine or cytosine residue is inserted after nucleic acid residue 48 of exon 7 of SMN2, or a single nucleotide is inserted after nucleic acid residue 45, 46, or 47 of exon 7 of SMN2, and (ii) a first reporter gene fused in frame to the nucleic acid residues of exon 8 of SMN or a fragment thereof, wherein the first reporter gene does not have a start codon; (b) detecting the amount or activity of a first fusion protein encoded by the first minigene; and (c) comparing the amount or activity of the first fusion protein expressed by the first host cell with the amount or activity of a second fusion protein expressed by a second host cell contacted with a second concentration of the compound, wherein said first and second concentrations are stoichiometrically equivalent, and, wherein the second host cell contains a second nucleic acid construct comprising a second minigene which comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN, wherein a single guanine residue is inserted after nucleic acid residue 48 of exon 7 of SMN2, and (ii) a second reporter gene fused in frame to the nucleic acid residues of exon 8 of SMN or a fragment thereof, wherein the second reporter gene does not have a start codon, and wherein a compound that modulates inclusion of exon 7 of SMN2 into mRNA transcribed from the SMN2 gene is identified and validated if the amount or the activity of the first fusion protein expressed by the first host cell is altered in the presence of the compound relative to the amount or the activity of the first fusion protein expressed by the first host cell in the absence of the compound or the presence of a negative control, and the amount or the activity of the second fusion protein expressed by the second host cell is not significantly altered in the presence of the compound relative to the amount or activity of the second fusion protein expressed by the second host cell in the absence of compound or the presence of a negative control. In a specific embodiment, the first and second minigenes have a start codon added to the 5' end of exon 6 of SMN or a fragment thereof. In a specific embodiment, the alteration in the amount or activity of the first fusion protein is a significant alteration. In certain embodiments, the fragment of exon 8 of SMN of the second minigene is composed of more or less than the first 21 nucleotides of exon 8 of SMN.

In another embodiment, an assay of the present invention includes a method for the identification and/or validation of a compound that increases the inclusion of exon 7 of SMN2 into mRNA transcribed from the SMN2 gene comprising the steps of: (a) contacting a first concentration of a compound with a first host cell containing a first nucleic acid construct which comprises a first minigene, wherein the first minigene comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a first reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (b) detecting the activity or amount of a first fusion protein encoded by the first minigene; and (c) comparing the activity or amount of the first fusion protein with the activity or amount of a second fusion protein expressed by a second host cell contacted with a second concentration of the compound, wherein the first and second concentrations of the compound are equivalent, and wherein the second host cell contains a second nucleic acid construct comprising a second minigene encoding the second fusion protein which comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a second reporter gene lacking a start codon, wherein a single guanine residue is inserted after nucleic acid residue 48 of exon 7 of SMN2; wherein a compound that increases the inclusion of exon 7 of SMN2 into mRNA transcribed from the SMN2 gene is identified and/or validated if the activity or amount of the first fusion protein expressed by the first host cell is increased in the presence of the compound relative to the activity or amount of the first fusion protein expressed by the first host cell in the absence of the compound or the presence of a negative control (e.g., PBS or DMSO), and the activity or amount of the second fusion protein expressed by the second host cell is not significantly altered in the presence of the compound relative to the absence of the compound or the presence of a negative control (e.g., PBS or DMSO). In one aspect, the first and second minigenes each comprise a start codon 5' to the nucleic acid residues of exon 6 of SMN, wherein the first codon of the coding sequence of the first reporter gene and the start codon of the first minigene are in the same open reading frame, and wherein the first codon of the coding sequence of the second reporter gene and the start codon of the second minigene are in the same open reading frame.

In another embodiment, an assay of the present invention includes a method for the identification and/or validation of a compound that increases the inclusion of exon 7 of SMN2 into mRNA transcribed from the SMN2 gene comprising the steps of: (a) contacting a first concentration of a compound with a first host cell containing a first nucleic acid construct which comprises a first minigene, wherein the first minigene comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a first reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first codon of the coding sequence of the first reporter gene and the first start codon of the nucleic acid residues of exon 6 of SMN or a fragment thereof of the first minigene are in the same open reading frame; (b) detecting the activity or amount of a first fusion protein encoded by the first minigene; and (c) comparing the activity or amount of the first fusion protein with the activity or amount of a second fusion protein expressed by a second host cell contacted with a second concentration of the compound, wherein the first and second concentrations of the compound are equivalent, and wherein the second host cell contains a second nucleic acid construct comprising a second minigene encoding the second fusion protein which comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a second reporter gene lacking a start codon, wherein a single guanine residue is inserted after nucleic acid residue 48 of exon 7 of SMN2, and wherein the first codon of the coding sequence of the second reporter gene and the first start codon of the nucleic acid residues of exon 6 of SMN or a fragment thereof of the second minigene are in the same open reading frame; wherein a compound that increases the inclusion of exon 7 of SMN2 into mRNA transcribed from the SMN2 gene is identified and/or validated if the activity or amount of the first fusion protein expressed by the first host cell is increased in the presence of the compound relative to the activity or amount of the first fusion protein expressed by the first host cell in the absence of the compound or the presence of a negative control (e.g., PBS or DMSO), and the activity or amount of the second fusion protein expressed by the second host cell is not significantly altered in the presence of the compound relative to the absence of the compound or the presence of a negative control (e.g., PBS or DMSO).

In another embodiment, an assay of the present invention includes a method for the identification and/or validation of a compound that increases the inclusion of exon 7 of SMN2 into mRNA transcribed from the SMN2 gene comprising the steps of: (a) contacting a first concentration of a compound with a first host cell containing a first nucleic acid construct which comprises a first minigene, wherein the first minigene comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a first reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first codon of the coding sequence of the first reporter gene and the first start codon of the first minigene are in the same open reading frame; (b) detecting the activity or amount of a first fusion protein encoded by the first minigene; and (c) comparing the activity or amount of the first fusion protein with the activity or amount of a second fusion protein expressed by a second host cell contacted with a second concentration of the compound, wherein the first and second concentrations of the compound are equivalent, and wherein the second host cell contains a second nucleic acid construct comprising a second minigene encoding the second fusion protein which comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a second reporter gene lacking a start codon, wherein a single guanine residue is inserted after nucleic acid residue 48 of the nucleic acid residues of exon 7 of SMN2, and wherein the first codon of the coding sequence of the second reporter gene and the first start codon of the second minigene are in the same open reading frame; wherein a compound that increases the inclusion of exon 7 of SMN2 into mRNA transcribed from the SMN2 gene is identified and/or validated if the activity or amount of the first fusion protein expressed by the first host cell is increased in the presence of the compound relative to the activity or amount of the first fusion protein expressed by the first host cell in the absence of the compound or the presence of a negative control (e.g., PBS or DMSO), and the activity or amount of the second fusion protein expressed by the second host cell is not significantly altered in the presence of the compound relative to the absence of the compound or the presence of a negative control (e.g., PBS or DMSO).

In another embodiment, an assay of the present invention includes a method for the identification and/or validation of a compound that increases the inclusion of exon 7 of SMN2 into mRNA transcribed from the SMN2 gene comprising the steps of: (a) contacting a first concentration of a compound with a first host cell containing a first nucleic acid construct which comprises a first minigene, wherein the first minigene comprises, in 5' to 3' order: nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a first reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first amino acid sequence include a start codon; (iii) the nucleic acid residues encoding the first and second amino acid sequences permit removal of an intron via mRNA splicing, and (iv) the first codon of the coding sequence of the first reporter gene and the first start codon of the first amino acid sequence are in the same open reading frame; (b) detecting the activity or amount of a first fusion protein encoded by the first minigene; and (c) comparing the activity or amount of the first fusion protein with the activity or amount of a second fusion protein expressed by a second host cell contacted with a second concentration of the compound, wherein the first and second concentrations of the compound are equivalent, and wherein second host cell contains a second nucleic acid construct comprising a second minigene encoding the second fusion protein which comprises, in 5' to 3' order: nucleic acid residues encoding a third amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a fourth amino acid sequence, and the nucleic acid residues of the coding sequence of a second reporter gene lacking a start codon, wherein (i) a single guanine residue is inserted after nucleic acid residue 48 of the nucleic acid residues of exon 7 of SMN2; (ii) the nucleic acid residues encoding the third amino acid sequence include a start codon; (iii) the nucleic acid residues encoding the third and fourth amino acid sequences permit removal of an intron via mRNA splicing, and (iv) the first codon of the coding sequence of the second reporter gene and the first start codon of the third amino acid sequence are in the same open reading frame; wherein a compound that increases the inclusion of exon 7 of SMN2 into mRNA transcribed from the SMN2 gene is identified and/or validated if the activity or amount of the first fusion protein expressed by the first host cell is increased in the presence of the compound relative to the activity or amount of the first fusion protein expressed by the first host cell in the absence of the compound or the presence of a negative control (e.g., PBS or DMSO), and the activity or amount of the second fusion protein expressed by the second host cell is not significantly altered in the presence of the compound relative to the absence of the compound or the presence of a negative control (e.g., PBS or DMSO).

In another embodiment, an assay of the present invention includes a method for the identification and/or validation of a compound that increases the inclusion of exon 7 of SMN2 into mRNA transcribed from the SMN2 gene comprising the steps of: (a) contacting a first concentration of a compound with a first host cell containing a first nucleic acid construct which comprises a first minigene, wherein the first minigene comprises, in 5' to 3' order: a start codon, nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a first reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first and second amino acid sequences permit removal of an intron via mRNA splicing, and (iii) the first codon of the coding sequence of the first reporter gene and the first start codon of the first minigene are in the same open reading frame; (b) detecting the activity or amount of a first fusion protein encoded by the first minigene; and (c) comparing the activity or amount of the first fusion protein with the activity or amount of a second fusion protein expressed by a second host cell contacted with a second concentration of the compound, wherein the first and second concentrations of the compound are equivalent, and wherein the second host cell contains a second nucleic acid construct comprising a second minigene encoding the second fusion protein which comprises, in 5' to 3' order: a start codon, nucleic acid residues encoding a third amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a fourth amino acid sequence, and the nucleic acid residues of the coding sequence of a second reporter gene lacking a start codon, wherein (i) a single guanine residue is inserted after nucleic acid residue 48 of the nucleic acid residues of exon 7 of SMN2; (ii) the nucleic acid residues encoding the third and fourth amino acid sequences permit removal of an intron via mRNA splicing, and (iii) the first codon of the coding sequence of the second reporter gene and the start codon of the second minigene are in the same open reading frame; wherein a compound that increases the inclusion of exon 7 of SMN2 into mRNA transcribed from the SMN2 gene is identified and/or validated if the activity or amount of the first fusion protein expressed by the first host cell is increased in the presence of the compound relative to the activity or amount of the first fusion protein expressed by the first host cell in the absence of the compound or the presence of a negative control (e.g., PBS or DMSO), and the activity or amount of the second fusion protein expressed by the second host cell is not significantly altered in the presence of the compound relative to the absence of the compound or the presence of a negative control (e.g., PBS or DMSO).

In a specific embodiment, the first cell and the second cell are the same cell type. In some embodiments, the first cell and the second cell are the same cell type and are obtained from the same source or clone. In some embodiments, the first reporter gene and the second reporter gene are the same reporter gene. In other embodiments, the first reporter gene and second reporter gene are different reporter genes. A compound that increases the inclusion of exon 7 of SMN2 into mRNA transcribed from the SMN2 gene will result in a Fold Activation derived from a higher ratio of the First Activation:

$$\text{First Activation} = \frac{\text{the amount or the activity of the first fusion protein expressed by the first host cell in the presence of the compound}}{\text{the amount or the activity of the first fusion protein expressed by the first host cell in the absence of the compound or the presence of a negative control}}$$

compared to the ratio of the Second Activation:

$$\text{Second Activation} = \frac{\text{the amount or the activity of the second fusion protein expressed by the second host cell in the presence of the compound}}{\text{the amount or the activity of the second fusion protein expressed by the second host cell in the absence of the compound or the presence of a negative control}}$$

In some embodiments, both the amount and activity of the first and second fusion proteins are detected. Accordingly, as used herein, the Fold Activation for a compound that modulates the inclusion of exon 7 of SMN2 into mRNA transcribed from the SMN2 gene is a ratio of the First Activation divided by the Second Activation.

In certain embodiments, in addition to, or as an alternative to, detecting the amount or activity of the first and second fusion proteins, the amount of mRNA transcript containing exon 7 of SMN2 or a fragment thereof transcribed from the first and second minigenes can be detected. In accordance with such embodiments, a compound that modulates inclusion of exon 7 of SMN2 into mRNA transcribed from the SMN2 gene is identified and validated if the compound alters the amount of mRNA transcript containing exon 7 of SMN2 or a fragment thereof transcribed from the first minigene relative to the amount of mRNA transcript containing exon 7 of SMN2 or a fragment thereof transcribed from the first minigene in the absence of the compound or in the presence of a negative control, but the compound does not significantly alter the amount of mRNA transcript containing exon 7 of SMN2 or a fragment thereof transcribed from the second minigene relative to the amount of mRNA transcript containing exon 7 of SMN2 or a fragment thereof transcribed from the second minigene in the absence of the compound or the presence of a negative control. In a specific embodiment, the alteration in the amount of mRNA transcript containing exon 7 of SMN2 or a fragment thereof transcribed from the first minigene is a significant alteration. A compound that increases the inclusion of exon 7 of SMN2 into mRNA transcribed from the SMN2 gene is identified and validated if the amount of mRNA transcript containing exon 7 of SMN2 or a fragment thereof transcribed from the first minigene in the presence of the compound relative to the amount of mRNA transcript containing exon 7 of SMN2 or a fragment thereof transcribed from the first minigene in the absence of the compound or the presence of a negative control is greater than the amount of mRNA transcript containing exon 7 of SMN2 or a fragment thereof transcribed from the second minigene in the presence of the compound relative to the amount of mRNA transcript containing exon 7 of SMN2 or a fragment thereof transcribed from the second minigene in the absence of the compound or the presence of a negative control.

In another embodiment, the present invention includes a method for identifying and validating a compound that modulates inclusion of exon 7 of SMN2 into mRNA transcribed from the SMN2 gene comprising the steps of: (a) contacting a compound with a host cell containing a first nucleic acid construct and a second nucleic acid construct, wherein (1) the first nucleic acid construct comprises a first minigene which comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN, wherein either a single adenine, thymine or cytosine residue is inserted after nucleic acid residue 48 of exon 7 of SMN2, or a single nucleotide is inserted after nucleic acid residue 45, 46 or 47 of exon 7 of SMN2, and (ii) a first reporter gene fused in frame to the nucleic acid residues of exon 8 of SMN or a fragment thereof, wherein the first reporter gene does not have a start codon, and wherein (2) the second nucleic acid construct comprises a second minigene which comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN, wherein a single guanine residue is inserted after nucleic acid residue 48 of exon 7 of SMN2, and (ii) a second reporter gene fused in frame to the nucleic acid residues of exon 8 of SMN or a fragment thereof, wherein the second reporter gene does not have a start codon and second reporter gene is different than the first reporter gene; (b) detecting the amount or activity of the first fusion protein encoded by the first minigene and detecting the amount or activity of the second fusion protein encoded by the second minigene; and (c) comparing the amount or activity of the first fusion protein with the amount or activity of the second fusion protein, wherein a compound that modulates inclusion of exon 7 of SMN2 into mRNA transcribed from the SMN2 gene is identified and validated if the amount or activity of the first fusion protein expressed by the host cell is altered in the presence of the compound relative to the amount or activity of the first fusion protein expressed by the host cell in the absence of the compound or the presence of a negative control; and the amount or activity of the second fusion protein expressed by the host cell is not significantly altered in the presence of the compound relative to the amount or activity of the second fusion protein expressed by the host cell in the absence of the compound or the presence of a negative control. In a specific embodiment, the alteration in the amount or activity of the first fusion protein is a significant alteration.

In a specific embodiment, the first and second minigenes have a start codon added to the 5' end of exon 6 of SMN or a fragment thereof. In some embodiments, the fragment of exon 8 of SMN of the second minigene is composed of more or less than the first 21 nucleotides of exon 8 of SMN. A compound that increases the inclusion of exon 7 of SMN2 into mRNA transcribed from the SMN2 gene, and thus increases levels of SMN protein produced from the SMN2 gene, will result in an increased amount or activity of the first fusion protein expressed by the host cell relative to the amount or activity of the first fusion protein expressed by the host cell in the absence of the compound or the presence of a negative control, but the compound will not significantly alter the amount or activity of the second fusion protein expressed by the host cell relative to the amount or activity of the second fusion protein expressed by the host cell in the absence of the compound or the presence of a negative control. In some embodiments, both the amount and activity of the fusion protein are detected.

In some embodiments, in addition to, or as an alternative to, detecting the amount or activity of the first and second fusion proteins, the amount of mRNA transcripts containing exon 7 of SMN2 or a fragment thereof transcribed from the first and second minigenes is detected. In accordance with such embodiments, a compound that modulates the inclusion of exon 7 of SMN2 into mRNA transcribed from the SMN2 gene is identified or validated if the compound alters the amount of mRNA transcript containing exon 7 of SMN2 or a fragment thereof transcribed from the first minigene relative to the amount of mRNA transcript containing exon 7 of SMN2 or a fragment thereof transcribed from the first minigene in the absence of the compound, but the compound does not significantly alter the amount of the mRNA transcript containing exon 7 of SMN2 or a fragment thereof transcribed from the second minigene relative to the amount obtained in the absence of the compound. In a specific embodiment, the alteration in the amount of the mRNA transcript containing exon 7 of SMN2 or a fragment thereof transcribed from the first minigene is a significant alteration.

A compound that enhances the inclusion of exon 7 of SMN2 into mRNA transcribed from the SMN2 gene is identified and validated if: (i) the amount of mRNA transcript containing exon 7 of SMN2 or a fragment thereof transcribed from the first minigene is increased in the presence of the compound relative to the amount of mRNA transcript containing exon 7 of SMN2 or a fragment thereof transcribed from the first minigene in the absence of the compound or the presence of a negative control; and (ii) the amount of mRNA transcript containing exon 7 of SMN2 or a fragment thereof is not significantly altered in the presence of the compound relative to the amount of mRNA transcript of SMN2 or a fragment thereof transcribed from the second minigene in the absence of the compound or the presence of a negative control.

In another embodiment, the present invention includes a method for identifying and validating a compound that modulates inclusion of exon 7 of SMN2 into mRNA transcribed from the SMN2 gene comprising the steps of: (a) contacting a compound with a host cell containing a first nucleic acid construct and a second nucleic acid construct, wherein (1) the first nucleic acid construct comprises a first minigene which comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN, wherein either a single adenine, thymine or cytosine residue is inserted after nucleic acid residue 48 of exon 7 of SMN2, or a single nucleotide is inserted after nucleic acid residue 45, 46 or 47 of exon 7 of SMN2, and (ii) a first reporter gene fused in frame to the nucleic acid residues of exon 8 of SMN or a fragment thereof, wherein the first reporter gene does not have a start codon, and wherein (2) the second nucleic acid construct comprises a second minigene which comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN, wherein a single guanine residue is inserted after nucleic acid residue 48 of exon 7 of SMN2, and (2) a second reporter gene fused in frame to the nucleic acid residues of exon 8 of SMN or a fragment thereof, wherein the second reporter gene does not have a start codon and the second reporter gene is different from the first reporter gene (e.g., first reporter gene is a luciferase reporter gene and the second reporter gene is a green fluorescent protein reporter gene); (b) detecting the amount or activity of the first fusion protein and the amount or activity of the second fusion protein encoded by the first and second minigenes, respectively; and (c) comparing a first ratio obtained by dividing the amount or activity of the first fusion protein expressed by the host cell by the amount or activity of the second fusion protein expressed by the host cell, each detected in the presence of the compound or in the presence of a positive control, with a second ratio obtained by dividing the amount or activity of the first fusion protein expressed by the host cell by the amount or activity of the second fusion protein expressed by the host cell, each detected in the absence of the compound or in the presence of a negative control, wherein a compound that modulates inclusion of exon 7 of SMN2 into mRNA transcribed from the SMN2 gene is identified and validated if the first ratio is different than the second ratio. A compound that enhances the inclusion of exon 7 of SMN2 into mRNA transcribed from the SMN2 gene is identified and validated if the first ratio is greater than second ratio. In a specific embodiment, the first and second minigenes have a start codon added to the 5' end of exon 6 of SMN or a fragment thereof.

In another embodiment, an assay of the present invention includes a method for the identification and/or validation of a compound that increases the inclusion of exon 7 of SMN2 into mRNA transcribed from the SMN2 gene comprising the steps of: (a) contacting a compound with a host cell containing: (i) a first nucleic acid construct comprising a first minigene which comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a first reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; and (ii) a second nucleic acid construct comprising a second minigene which comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, and a fragment of exon 8 of SMN, and the nucleic acid residues of the coding sequence of a second reporter gene lacking a start codon, wherein (i) a single guanine residue is inserted after nucleic acid residue 48 of exon 7 of SMN2, and (ii) the second reporter gene is different than the first reporter gene; (b) detecting the activity or amount of a first fusion protein encoded by the first minigene and the activity or amount of a second fusion protein encoded by the second minigene; and (c) comparing the activity or amount of the first fusion protein with the activity or amount of the second fusion protein;

wherein a compound that increases the inclusion of exon 7 of SMN2 into mRNA transcribed from the SMN2 gene is identified and/or validated if the activity or amount of the first fusion protein expressed by the host cell is increased in the presence of the compound relative to the activity or amount of the first fusion protein expressed by the host cell in the absence of the compound or the presence of a negative control (e.g., PBS or DMSO), and the activity or amount of the second fusion protein expressed by the host cell is not significantly altered in the presence of the compound relative to the absence of the compound or the presence of a negative control (e.g., PBS or DMSO). In one aspect, the first and second minigenes each comprise a start codon 5' to the nucleic acid residues of exon 6 of SMN, wherein the first codon of the coding sequence of the first reporter gene and the start codon of the first minigene are in the same open reading frame, and wherein the first codon of the coding sequence of the second reporter gene and the start codon of the second minigene are in the same open reading frame.

In another embodiment, an assay of the present invention includes a method for the identification and/or validation of a compound that increases the inclusion of exon 7 of SMN2 into mRNA transcribed from the SMN2 gene comprising the steps of: (a) contacting a compound with a host cell containing: (i) a first nucleic acid construct comprising a first minigene which comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a first reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first codon of the coding sequence of the first reporter gene and the first start codon of the nucleic acid residues of exon 6 of SMN or a fragment thereof of the first minigene are in the same open reading frame; and (ii) a second nucleic acid construct comprising a second minigene which comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a second reporter gene lacking a start codon, wherein a single guanine residue is inserted after nucleic acid residue 48 of the nucleic acid residues of exon 7 of SMN2, and wherein the first codon of the coding sequence of the second reporter gene and the first start codon of the nucleic acid residues of exon 6 of SMN or a fragment thereof of the second minigene are in the same open reading frame; (b) detecting the activity or amount of a first fusion protein encoded by the first minigene and the activity or amount of a second fusion protein encoded by the second minigene; and (c) comparing the activity or amount of the first fusion protein with the activity or amount of the second fusion protein; wherein a compound that increases the inclusion of exon 7 of SMN2 into mRNA transcribed from the SMN2 gene is identified and/or validated if the activity or amount of the first fusion protein expressed by the host cell is increased in the presence of the compound relative to the activity or amount of the first fusion protein expressed by the host cell in the absence of the compound or the presence of a negative control (e.g., PBS or DMSO), and the activity or amount of the second fusion protein expressed by the host cell is not significantly altered in the presence of the compound relative to the absence of the compound or the presence of a negative control (e.g., PBS or DMSO).

In another embodiment, an assay of the present invention includes a method for the identification and/or validation of a compound that increases the inclusion of exon 7 of SMN2 into mRNA transcribed from the SMN2 gene comprising the steps of: (a) contacting a compound with a host cell containing: (i) a first nucleic acid construct comprising a first minigene which comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a first reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first codon of the coding sequence of the first reporter gene and the first start codon of the first minigene are in the same open reading frame; and (ii) a second nucleic acid construct comprising a second minigene which comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a second reporter gene lacking a start codon, wherein a single guanine residue is inserted after nucleic acid residue 48 of the nucleic acid residues of exon 7 of SMN2, and wherein the first codon of the coding sequence of the second reporter gene and the first start codon of the second minigene are in the same open reading frame; (b) detecting the activity or amount of a first fusion protein encoded by the first minigene and the activity or amount of a second fusion protein encoded by the second minigene; and (c) comparing the activity or amount of the first fusion protein with the activity or amount of the second fusion protein; wherein a compound that increases the inclusion of exon 7 of SMN2 into mRNA transcribed from the SMN2 gene is identified and/or validated if the activity or amount of the first fusion protein expressed by the host cell is increased in the presence of the compound relative to the activity or amount of the first fusion protein expressed by the host cell in the absence of the compound or the presence of a negative control (e.g., PBS or DMSO), and the activity or amount of the second fusion protein expressed by the host cell is not significantly altered in the presence of the compound relative to the absence of the compound or the presence of a negative control (e.g., PBS or DMSO).

In another embodiment, an assay of the present invention includes a method for the identification and/or validation of a compound that increases the inclusion of exon 7 of SMN2 into mRNA transcribed from the SMN2 gene comprising the steps of: (a) contacting a compound with a host cell containing: (1) a first nucleic acid construct comprising a first minigene which comprises, in 5' to 3' order: nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a first reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first amino acid sequence includes a start codon; (iii) the nucleic acid residues encoding the first and second amino acid sequences permit removal of an intron via mRNA splicing, and (iv) the first codon of the coding sequence of the first reporter gene and the first start codon of the first amino acid sequence are in the same open reading frame; and (2) a second nucleic acid construct comprising a second minigene which comprises, in 5' to 3' order: nucleic acid residues encoding a third amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a fourth amino acid sequence, and the nucleic acid residues of the coding sequence of a second reporter gene lacking a start codon, wherein (i) a single guanine residue is inserted after nucleic acid residue 48 of the nucleic acid residues of exon 7 of SMN2; (ii) the nucleic acid residues encoding the third amino acid sequence include a start codon, (iii) the nucleic acid residues encoding the third and fourth amino acid sequences permit removal of an intron via mRNA splicing, (iv) the first codon of the coding sequence of the second reporter gene and the first start codon of the third amino acid sequence are in the same open reading frame, and (v) the second reporter gene is different than the first reporter gene; (b) detecting the activity or amount of a first fusion protein encoded by the first minigene and the activity or amount of a second fusion protein encoded by the second minigene; and (c) comparing the activity or amount of the first fusion protein with the activity or amount of the second fusion protein; wherein a compound that increases the inclusion of exon 7 of SMN2 into mRNA transcribed from the SMN2 gene is identified and/or validated if the activity or amount of the first fusion protein expressed by the host cell is increased in the presence of the compound relative to the activity or amount of the first fusion protein expressed by the host cell in the absence of the compound or the presence of a negative control (e.g., PBS or DMSO), and the activity or amount of the second fusion protein expressed by the host cell is not significantly altered in the presence of the compound relative to the absence of the compound or the presence of a negative control (e.g., PBS or DMSO). In one aspect, the first minigene comprises a start codon 5' to the nucleic acid residues encoding a first amino acid sequence and the second minigene comprises a start codon 5' to the nucleic acid residues encoding a third amino acid sequence, wherein the first codon of the coding sequence of the first reporter gene and the start codon of the first minigene are in the same open reading frame, and wherein the first codon of the coding sequence of the second reporter gene and the start codon of the second minigene are in the same open reading frame.

In another embodiment, an assay of the present invention includes a method for the identification and/or validation of a compound that increases the inclusion of exon 7 of SMN2 into mRNA transcribed from the SMN2 gene comprising the steps of: (a) contacting a compound with a host cell containing: (1) a first nucleic acid construct comprising a first minigene which comprises, in 5' to 3' order: a start codon, nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a first reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first and second amino acid sequences permit removal of an intron via mRNA splicing, and (iii) the first codon of the coding sequence of the first reporter gene and the first start codon of the first minigene are in the same open reading frame; and (2) a second nucleic acid construct comprising a second minigene which comprises, in 5' to 3' order: a start codon, nucleic acid residues encoding a third amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a fourth amino acid sequence, and the nucleic acid residues of the coding sequence of a second reporter gene lacking a start codon, wherein (i) a single guanine residue is inserted after nucleic acid residue 48 of the nucleic acid residues of exon 7 of SMN2; (ii) the nucleic acid residues encoding the third and fourth amino acid sequences permit removal of an intron via mRNA splicing, (iii) the first codon of the coding sequence of the second reporter gene and the first start codon of the second minigene are in the same open reading frame, and (iv) the second reporter gene is different than the first reporter gene; (b) detecting the activity or amount of a first fusion protein encoded by the first minigene and the activity or amount of a second fusion protein encoded by the second minigene; and (c) comparing the activity or amount of the first fusion protein with the activity or amount of the second fusion protein; wherein a compound that increases the inclusion of exon 7 of SMN2 into mRNA transcribed from the SMN2 gene is identified and/or validated if the activity or amount of the first fusion protein expressed by the host cell is increased in the presence of the compound relative to the activity or amount of the first fusion protein expressed by the host cell in the absence of the compound or the presence of a negative control (e.g., PBS or DMSO), and the activity or amount of the second fusion protein expressed by the host cell is not significantly altered in the presence of the compound relative to the absence of the compound or the presence of a negative control (e.g., PBS or DMSO). In certain embodiments, the nucleic acid sequences encoding the first, second, third, and fourth amino acid sequences are identical. In other embodiments, the first, second, third, and fourth amino acid sequences encoded by the first, second, third, and fourth nucleic acid sequences nucleic acid are identical. Those of skill in the art will understand that, due to the degeneracy of the genetic code, different nucleic acid sequences can code for the identical amino acid sequence.

The expression of the fusion protein encoded by the nucleic acid construct in the cell-based assays described herein may be detected by any technique well-known to one of skill in the art. For example, techniques well-known to one of skill in the art for detecting reporter proteins can be used to detect the amount and activity of fusion proteins. Methods for detecting the expression of a reporter protein will vary with the reporter gene used. Assays for the various reporter genes are well-known to one of skill in the art. To assess whether a compound modulates inclusion of exon 7 of SMN2 into mRNA transcribed from the SMN2 gene, the level of RNA transcript containing exon 7 of SMN2 or a fragment thereof may be detected using techniques well-known to one of skill in the art. For example, total RNA may be isolated from cells containing a nucleic acid construct described above, followed by cDNA synthesis and quantitative RT PCR analysis. In one embodiment, forward and reverse primer pairs are used in quantitative RT PCR analysis. The forward primer is designed to bind to exon 6 or the exon 6/exon 7 junction, and the reverse primer is designed to bind to exon 8 or the reporter gene, depending on whether alternative splicing is detected in mRNA transcripts transcribed from the endogenous SMN2 gene or a minigene described herein. A quantitative RT PCR probe is designed to bind to exon 7 or the exon 6/exon 7 junction or the exon 7/exon 8 junction.

In a specific embodiment, a method based on quantitative real-time PCR is used wherein the 5' primer binds to nucleic acid sequences within exon 7 and the 3' primer binds to nucleic acid sequences in the reporter gene, and wherein a probe complementary to sequences found in the 3' region of exon 7 and the 5' region of exon 8 hybridizes to the junction region between exon 7 and exon 8 to measure the levels of mRNA transcripts containing exon 7 of SMN2 or a fragment thereof produced from a minigene described herein. An example of the aforementioned real-time PCR assay is described herein, and a schematic drawing of the sequences in the SMN2 minigene-reporter gene construct bound by the primers and the probe is shown in FIG. 5.

Cell-Free Assays

The present invention provides for the use of the nucleic acid construct described herein in a cell-free assay. Techniques for use of various nucleic acid constructs in a cell-free assay are generally known to those skilled in the art. Accordingly, techniques for the use of the instant nucleic acid construct in a cell-free assay will employ, unless otherwise indicated, routine conventional techniques of molecular biology, microbiology, and recombinant DNA manipulation and production.

In certain embodiments, the present invention includes a method for identifying and/or validating a compound that modulates inclusion of exon 7 of SMN2 into mRNA transcribed from the SMN2 gene comprising: (a) contacting a compound with a composition comprising a cell-free extract and a pre-mRNA transcript encoded by a minigene of a nucleic acid construct described herein or a nucleic acid construct described herein; and (b) measuring the amount of mRNA transcripts containing exon 7 of SMN2 or a fragment thereof. In one embodiment, the present invention includes a method for identifying or validating a compound that modulates inclusion of exon 7 of SMN2 into mRNA transcribed from the SMN2 gene comprising the steps of: (a) contacting a compound with a cell-free extract containing a pre-mRNA comprising, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN, and (b) measuring the amount of the mRNA transcripts containing exon 7 of SMN2 or a fragment thereof.

In a specific embodiment, the pre-mRNA has a start codon added to the 5' end of exon 6 of SMN or a fragment thereof. A compound that alters inclusion of exon 7 of SMN2 into mRNA transcribed from the SMN2 gene is identified or validated if the amount of mRNA transcript containing exon 7 of SMN2 or a fragment thereof obtained when the cell-free extract is contacted with the compound is altered relative to the amount of mRNA transcript containing exon 7 of SMN2 or a fragment thereof obtained when the cell-free extract is not contacted with the compound or is contacted with a negative control, or relative to a previously determined reference range, that is the amount of mRNA transcript containing exon 7 of SMN2 or a fragment thereof obtained for a negative control. In a specific embodiment, the alteration in the amount of mRNA transcript containing exon 7 of SMN2 or a fragment thereof is a significant alteration. In a specific embodiment, a negative control (e.g., DMSO, PBS or another agent that is known to have no effect on splicing of exon 7 of SMN2) and a positive control (e.g., an agent that is known to have an effect on exon 7 splicing of SMN2) are included in the cell-free assays described herein.

In some embodiments, the terms "significantly altered" and "significant alteration" refer to a difference in values for a measurement taken of replicate wells of a sample under the same conditions with the exception of one variable, which difference is statistically significant. In a specific embodiment, a difference is statistically significant if the p-value is less than 0.1, 0.05, 0.01, or 0.001.

In a specific embodiment, the present invention includes a method for identifying or validating a compound that increases the inclusion of exon 7 of SMN2 into mRNA transcribed from the SMN2 gene comprising the steps of: (a) contacting a compound with a cell-free extract containing a pre-mRNA comprising, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN; and (b) measuring the amount of mRNA transcripts containing exon 7 of SMN2 or a fragment thereof, wherein a compound that increases the inclusion of exon 7 of SMN2 into mRNA transcribed from the SMN2 gene is identified or validated if the compound increases the amount of mRNA transcript containing exon 7 of SMN2 or a fragment thereof obtained relative to the amount of mRNA transcript containing exon 7 of SMN2 or a fragment thereof obtained when the cell-free extract is not contacted with the compound or is contacted with a negative control (e.g., DMSO, PBS and the like), or relative to a previously determined reference range that is the amount of the mRNA transcript containing exon 7 of SMN2 or a fragment thereof obtained for a negative control. In one specific embodiment, the pre-mRNA has a start codon added to the 5' end of exon 6 of SMN or a fragment thereof.

In certain embodiments, the present invention includes a method for identifying or validating a compound that modulates inclusion of exon 7 of SMN2 into mRNA transcribed from the SMN2 gene comprising the steps of: (a) contacting a compound with a cell-free extract containing a pre-mRNA comprising, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, and the nucleic acid residues of intron 7 of SMN or a fragment thereof, and a fragment of the nucleic acid residues of exon 8 of SMN, wherein either a single adenine, thymine or cytosine residue is inserted after nucleic acid residue 48 of exon 7 of SMN2, or a single nucleotide is inserted after nucleic acid residue 45, 46 or 47 of exon 7 of SMN2; and (b) measuring the amount of mRNA transcripts containing exon 7 of SMN2 or a fragment thereof, wherein a compound that modulates inclusion of exon 7 of SMN2 into mRNA transcribed from the SMN2 gene is identified or validated if the compound alters the amount of mRNA transcript containing exon 7 of SMN2 or a fragment thereof relative to the amount of mRNA transcript containing exon 7 of SMN2 or a fragment thereof obtained when the cell-free extract is not contacted with the compound or is contacted with a negative control (e.g., DMSO, PBS and the like), or relative to a previously determined reference range that is the amount of mRNA transcript containing exon 7 of SMN2 or a fragment thereof obtained for a negative control. In a specific embodiment, the alteration in the amount of mRNA transcript containing exon 7 of SMN2 or a fragment thereof is a significant alteration.

In one specific embodiment, the pre-mRNA has a start codon added to the 5' end of exon 6 of SMN or a fragment thereof. In another embodiment, the pre-mRNA further comprises nucleic acid residues encoding a reporter gene fused in frame to the nucleic acid residues of exon 8 of SMN or a fragment thereof, wherein the reporter gene does not have a start codon.

In one embodiment, the present invention includes a method for identifying or validating a compound that enhances the inclusion of exon 7 of SMN2 into mRNA transcribed from the SMN2 gene comprising the steps of: (a) contacting a compound with a cell-free extract containing a pre-mRNA comprising, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof, and a fragment of the nucleic acid residues of exon 8 of SMN, wherein either a single adenine, thymine or cytosine residue is inserted after nucleic acid residue 48 of exon 7 of SMN2, or a single nucleotide is inserted after nucleic acid residue 45, 46 or 47 or exon 7 of SMN2; and (b) measuring the amount of mRNA transcript containing exon 7 of SMN2 or a fragment thereof, wherein a compound that enhances the inclusion of exon 7 of SMN2 into mRNA transcribed from the SMN2 gene is identified or validated if the compound increases the amount of mRNA transcript containing exon 7 of SMN2 or a fragment thereof obtained in the cell-free extract relative to the amount of mRNA transcript containing exon 7 of SMN2 or a fragment thereof obtained when the cell-free extract is not contacted with the compound or is contacted with a negative control (e.g., DMSO, PBS and the like), or relative to a previously determined reference range that is the amount of mRNA transcript obtained for a negative control.

In one specific embodiment, the pre-mRNA has a start codon added to the 5' end of exon 6 of SMN or a fragment thereof. In another embodiment, the pre-mRNA further comprises nucleic acid residues encoding a reporter gene fused in frame to the nucleic acid residues of exon 8 of SMN or a fragment thereof, wherein the reporter gene does not have a start codon.

In another embodiment, an assay of the present invention includes a method for the identification of a compound that increases the inclusion of exon 7 of SMN2 into mRNA transcribed from the SMN2 gene comprising the steps of: (a) contacting a compound with a composition comprising a cell-free extract and a pre-mRNA transcript encoded by a minigene of a nucleic acid construct or a nucleic acid construct, wherein the minigene comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2. In one aspect, the minigene comprises a start codon 5' to the nucleic acid residues of exon 6 of SMN, wherein the first codon of the coding sequence of the reporter gene and the start codon of the minigene are in the same open reading frame.

In another embodiment, an assay of the present invention includes a method for the identification of a compound that increases the inclusion of exon 7 of SMN2 into mRNA transcribed from the SMN2 gene comprising the steps of: (a) contacting a compound with a composition comprising a cell-free extract and a pre-mRNA transcript encoded by a minigene of a nucleic acid construct or a nucleic acid construct, wherein the minigene comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first start codon of the fragment of the nucleic acid residues of exon 6 of SMN and the first codon of the coding sequence of the reporter gene are in the same open reading frame.

In another embodiment, an assay of the present invention includes a method for the identification of a compound that increases the inclusion of exon 7 of SMN2 into mRNA transcribed from the SMN2 gene comprising the steps of: (a) contacting a compound with a composition comprising a cell-free extract and a pre-mRNA transcript encoded by a minigene of a nucleic acid construct or a nucleic acid construct, wherein the minigene comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first codon of the coding sequence of the reporter gene and the first start codon of the minigene are in the same open reading frame.

In another embodiment, an assay of the present invention includes a method for the identification of a compound that increases the inclusion of exon 7 of SMN2 into mRNA transcribed from the SMN2 gene comprising the steps of: (a) contacting a compound with a composition comprising a cell-free extract and a pre-mRNA transcript encoded by a minigene of a nucleic acid construct or a nucleic acid construct, wherein the minigene comprises, in 5' to 3' order: nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first amino acid sequence include a start codon; (iii) the nucleic acid residues encoding the first and second amino acid sequences permit removal of an intron via mRNA splicing, and (iv) the first codon of the coding sequence of the reporter gene and the start codon of the nucleic acid residues encoding the first amino acid sequence are in the same open reading frame.

In another embodiment, an assay of the present invention includes a method for the identification of a compound that increases the inclusion of exon 7 of SMN2 into mRNA transcribed from the SMN2 gene comprising the steps of: (a) contacting a compound with a composition comprising a cell-free extract and a pre-mRNA transcript encoded by a minigene of a nucleic acid construct or a nucleic acid construct, wherein the minigene comprises, in 5' to 3' order: a start codon, nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first and second amino acid sequences permit removal of an intron via mRNA splicing, and (iii) the first codon of the coding sequence of the reporter gene and the first start codon of the minigene are in the same open reading frame.

In some embodiments, as an alternative to, or in addition to, measuring the amount of mRNA transcript containing exon 7 of SMN2 or a fragment thereof, the amount or activity of the protein encoded by the pre-mRNA or nucleic acid construct can be detected. A compound that enhances the inclusion of exon 7 of SMN2 into mRNA transcribed from the SMN2 gene is identified or validated if the amount or activity of the protein encoded by the pre-mRNA or nucleic acid construct is increased in the presence of the compound relative to the amount or activity of the protein in the absence of the compound or the presence of a negative control, or a previously determined reference range.

The step of contacting a compound with a cell-free extract containing a nucleic acid construct or a pre-mRNA transcript as described herein or a composition containing a cell-free extract and a nucleic acid construct or a pre-mRNA transcript, may be conducted under conditions approximating or mimicking physiologic conditions. In a specific embodiment, a compound is added to the cell-free extract in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but not limited to, KCl, NaCl, $MgCl_2$, Tris-HCl, and/or Hepes. The optimal concentration of each salt used in the aqueous solution is dependent on the cell-free extract and compounds used and can be determined using routine experimentation.

A compound may be contacted with a cell-free extract containing a nucleic acid construct or a pre-mRNA or a composition containing a cell-free extract and a pre-mRNA transcript described herein or a nucleic acid construct described herein for a specific period of time. For example, a compound may be contacted with a cell-free extract containing a pre-mRNA for a time period of about 2 minutes, 5 minutes, 10 minutes, 15 minutes, 20 minutes, 30 minutes, 45 minutes, 1 hour, 2 hours, 3 hours, 4 hours, 8 hours, 10 hours, 12 hours, 14 hours, 16 hours, 18 hours or 24 hours. In some embodiments, the compound is contacted with a cell-free containing a pre-mRNA for a time period in a range of from about 1 minute to about 2 hours, from about 1 minute to about 1 hour, from about 1 minute to about 45 minutes, from about 1 minute to about 30 minutes, or from about 1 minute to about 15 minutes.

The effect of a compound on inclusion of exon 7 of SMN2 into mRNA transcribed from the SMN2 gene can be determined by assaying the amounts of mRNA transcripts containing exon 7 of SMN2 or a fragment thereof using techniques well-known to one of skill in the art. In a specific embodiment, the amounts of mRNA transcripts containing exon 7 of SMN2 or a fragment thereof may be determined by quantitative RT PCR. In one embodiment, 5' and 3' primer pairs are used in quantitative RT PCR analysis. The 5' primer is designed to bind to exon 6 or the exon 6/exon 7 junction, and the 3' primer is designed to bind to exon 8. A quantitative RT PCR probe is designed to bind to exon 7 or the exon 6/exon 7 junction or the exon 7/exon 8 junction. The ratio between mRNA transcripts containing exon 7 of SMN2 or a fragment thereof to other mRNA transcripts obtained in the assay may be determined by quantitative RT PCR.

Nucleic Acid Constructs for In Vitro Splicing Assays

A pre-mRNA suitable for use in an in vitro splicing assay may generally be prepared by in vitro run-off transcription. The present invention provides nucleic acid constructs that may be prepared by in vitro run-off transcription.

In one embodiment, the nucleic acid construct comprises, in 5' or 3' order: (i) a bacteriophage promoter; and (ii) a minigene comprising the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN2 or a fragment thereof, and the nucleic acid residues of intron 7 of SMN or a fragment thereof, and a fragment of the nucleic acid residues of exon 8 of SMN. In another embodiment, the nucleic acid construct comprises, in 5' to 3' order: (i) a bacteriophage promoter, (ii) a minigene comprising the nucleic acid residues of exon 6 of SMN or a fragment thereof, the nucleic acid residues of intron 6 of SMN or a fragment thereof, the nucleic acid residues of exon 7 of SMN2 or a fragment thereof, and the nucleic acid residues of intron 7 of SMN or a fragment thereof, and a fragment of the nucleic acid residues of exon 8 of SMN, wherein either a single adenine, thymine or cytosine residue is inserted after nucleic acid residue 48 of exon 7 of SMN2, or a single nucleotide is inserted after nucleic acid residue 45, 46 or 47 or exon 7 of SMN2 and (iii) a reporter gene fused in frame to the nucleic acid residues of exon 8 of SMN or a fragment thereof, wherein the reporter gene does not have a start codon.

In one specific embodiment, a start codon is added to the 5' end of exon 6 of SMN or a fragment thereof. In another embodiment, the bacteriophage promoter may be derived from T3, SP6, or T7 bacteriophage, or any other bacteriophage commonly used for in vitro transcription. Additionally, such nucleic acid constructs may be part of a vector that provides restriction endonuclease sites that are not present in the nucleic acid construct and may be used to linearize the vector.

Pre-mRNA Preparation

Any technique well-known to one skilled in the art may be used to generate pre-mRNAs suitable for use in cell-free systems. For example, a pre-mRNA can be made in run-off transcription of a linearized plasmid containing a bacteriophage promoter and a minigene wherein the bacteriophage promoter drives transcription of said minigene. Bacteriophage promoters from a T3, SP6 or T7 bacteriophage or any other suitable promoter may be used together with the respective RNA polymerase derived from the corresponding bacteriophage.

Vectors described herein are linearized with a restriction enzyme prior to in vitro run-off transcription, wherein the restriction sites for the restriction enzyme are located outside of the minigene nucleic acid construct contained in the vector. In a specific embodiment, the restriction enzyme creates 5' overhangs.

A pre-mRNA may be labeled by including one, two or more labeled ribonucleotides encoded in the vector. In a specific embodiment, one labeled ribonucleotide is present in the transcription reaction mixture. In a more specific embodiment, one $^{32}$P-labeled ribonucleotide is present in the transcription reaction mixture.

A capped pre-mRNA is more stable than an uncapped pre-mRNA. In addition, splicing occurs more efficiently with a capped pre-mRNA. In one embodiment, a dinucleotide primer is included in the plasmid to produce capped pre-mRNA. In a specific embodiment, the dinucleotide primer is mGpppG or GpppG.

A pre-mRNA from in vitro transcription may be purified by phenol extraction and ethanol precipitation or any technique well-known to one of skill in the art to yield a substantially pure pre-mRNA suitable for use in in vitro run-off transcription.

Cell-Free Extracts

Any technique well-known to one skilled in the art may be used to generate a whole cell extract or a nuclear extract suitable for use in in vitro splicing (otherwise referred to herein as cell-free extracts). In certain embodiments, the cell-free extracts are suitable for in vitro transcription and in vitro splicing. In some embodiments, the cell-free extracts are suitable for in vitro transcription, in vitro splicing, and in vitro translation.

The cell-free extract may be isolated from cells of any species origin. For example, the cell-free extract may be isolated from human cells (e.g., HEK293 or HeLa cells). In one embodiment, the human cells that can be used in the methods of the present invention are HeLa cells, HEK293 cells, fibroblasts, neuroblastoma cells or cell lines, motor neuron cells or cell lines, human stem cells or cell lines. In an alternative embodiment, murine cells are used such as mouse embryonic stem cells or cell lines. In a specific embodiment, cell-free extracts prepared from SMA patient cells or cell lines are used in the in vitro splicing reactions, such as a cell-free extract from the GM03813 cell line.

Compounds

Using the cell-based assays described herein, applicants have identified certain compounds that modulate inclusion of exon 7 of SMN2 into mRNA transcribed from the SMN2 gene. Further, any compound can be tested for its ability to modulate inclusion of exon 7 of SMN2 into mRNA transcribed from the SMN2 gene and to increase levels of SMN protein produced from the SMN2 gene using the screening assays described herein. Non-limiting examples of compounds include small molecules, peptides, proteins, and nucleic acids. In a specific embodiment, the compound is a small molecule. In a specific embodiment, the compound is a compound of Formula (I).

In one embodiment, a compound that modulates inclusion of exon 7 of SMN2 into mRNA transcribed from the SMN2 gene binds directly to SMN2 pre-mRNA. In another embodiment, a compound that modulates inclusion of exon 7 of SMN2 into mRNA transcribed from the SMN2 gene does not bind directly to SMN2 mRNA. In another embodiment, a compound that modulates inclusion of exon 7 of SMN2 into mRNA transcribed from the SMN2 gene binds to a protein that modulates inclusion of exon 7 of SMN2 into mRNA transcribed from the SMN2 gene. In yet another embodiment, a compound that modulates inclusion of exon 7 of SMN2 into mRNA transcribed from the SMN2 gene binds to a nucleotide regulatory sequence of a gene that encodes a protein that modulates inclusion of exon 7 of SMN2 into mRNA transcribed from the SMN2 gene.

In certain embodiments, a compound that modulates inclusion of exon 7 of SMN2 into mRNA transcribed from the SMN2 gene is not sodium vanadate. In some embodiments, a compound that modulates inclusion of exon 7 of SMN2 into mRNA transcribed from the SMN2 gene is not a chemotherapeutic agent. In some embodiments, a compound that modulates inclusion of exon 7 of SMN2 into mRNA transcribed from the SMN2 gene is not aclarubicin In a certain embodiments, the compound is a nucleic acid. In one embodiment, the compound is an antisense oligonucleotide. In another embodiment, the compound is an interfering RNA (RNAi) or microRNA (miRNA). RNAi comprises dsRNA that inhibits the expression of genes with complementary nucleotide sequences (Hannon G J. 2002. Science 418(6894):244-510). In another embodiment, the compound is a small interfering RNA (siRNA), about 20-25 residues in length. In animals, microRNAs (miRNA) are single-stranded RNA molecules that are complementary to the UTR regions of specific messenger RNA (mRNA) and typically inhibit protein translation of the mRNA (Ambros V., 2001. Cell 107(7):823-6; Bartel. Cell 116:281 (2004); Bartel. Cell 136: 215 (2009)). In a specific embodiment, the miRNA is about 20-25 residues in length. In another embodiment, a compound is a ribozyme. Ribozymes are RNA molecules possessing endoribonuclease activity. Ribozymes are engineered to cleave any RNA species site-specifically in the background of cellular RNA. The cleavage renders the mRNA unstable and prevents protein expression.

Assays for Detecting the Amount of mRNA Transcripts and the Amount and/or Activity of Proteins Encoded by SMN1 and SMN2

Compounds identified or validated in the assays described herein that modulate inclusion of exon 7 of SMN2 into mRNA transcribed from the SMN2 gene may be further tested in in vitro assays or in vivo assays well-known to one of skill in the art or described herein for the effect of said compounds on splicing of the SMN2 pre-mRNA. The selectivity of a particular compound's effect on exon inclusion in the pre-mRNA of one or more other genes (in a specific embodiment, a plurality of genes) can also be determined utilizing assays well-known to one of skill in the art or described herein. For example, quantitative RT PCR and primer pairs spanning an alternatively spliced exon and its neighboring exon may be used to determine inclusion of the alternatively spliced exon in a variety of genes. Another approach that may be used employs microarray technology where genes with alternative splice variants are represented by specific probe sets representing each splice variant. In another example, a cell-based assay may be used, wherein host cells containing minigene constructs of genes with alternative splice variants are brought into contact with the compound, wherein the compound modulates splicing when the expression of the mRNA and/or protein encoded by the minigene or the activity of the protein encoded by the minigene in the presence of the compound is altered relative to the expression of the mRNA and/or protein encoded by the minigene or the activity of the protein encoded by the minigene in the absence of the compound or relative to the presence of a negative control (e.g., PBS or DMSO and the like).

The expression of the gene products of SMN1 and SMN2 can be readily detected, e.g., by quantifying the protein and/or RNA encoded by such genes.

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One skilled in the art would be knowledgeable as to the parameters that can be modified to increase the binding of the antibody to an antigen and decrease the background (e.g., pre-clearing the cell lysate with sepharose beads).

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), incubating the membrane with primary antibody (the antibody of interest) diluted in blocking buffer, washing the membrane in washing buffer, incubating the membrane with a secondary antibody (which recognizes the primary antibody, e.g., an anti-human antibody) conjugated to an enzymatic substrate (e.g., horseradish peroxidase or alkaline phosphatase) or radioactive isotope (e.g., $^{32}$P or $^{125}$I)-labeled molecule diluted in blocking buffer, washing the membrane in wash buffer, and detecting the presence of the antigen. One of skill in the art would be knowledgeable as to the experimental variables that can be modified to increase the signal detected and to reduce the background signal.

ELISAs comprise preparing a solution of the antigen (for example, a cell lysate containing the antigen of interest or a buffered solution of a purified antigen of interest), coating the wells of a 96 well microtiter plate with the antigen, washing the wells with an inert buffer solution, adding an antigen-recognizing antibody conjugated to a reporter compound such as an enzymatic reporter (e.g., horseradish peroxidase or alkaline phosphatase) to the wells, incubating for a period of time, removing the excess conjugated antibody, washing the wells extensively with an inert buffer solution, and measuring the amount or the activity of retained reporter. In ELISAs, the antibody of interest does not have to be conjugated to a reporter compound; instead, a second antibody (which specifically binds the antigen-recognizing antibody) conjugated to a reporter compound may be added to the wells. Further, instead of coating the wells with the antigen, the antibody may be coated to the wells first. In this case, a second antibody conjugated to a reporter compound may be added following the addition of the antigen of interest to the coated wells. The antibody of interest does not have to be conjugated to a reporter compound; instead, a second antibody (which specifically binds the antigen-recognizing antibody) conjugated to a reporter compound may be added to the wells. One skilled in the art would be knowledgeable as to the experimental variables that can be modified to increase the signal detected as well as other variations of ELISAs known in the art.

In a specific embodiment, the levels of endogenous SMN, SMNΔEx7 and/or another protein encoded by SMN1 or SMN2 are determined by SMN In-Cell ELISA (SMN-ICE). SMN-ICE is an immunoreporter-based technique in which cells are fixed, permeabilized, blocked and incubated with primary and secondary antibodies. The secondary antibody is labeled with horseradish peroxidase (HRP) and the amount of HRP can be detected using known ELISA substrates. The SMN-ICE described and used herein is a variation of assays described for use in human lymphocytes (see, Kolb et al., 2006. *BMC Neurol.* 6:6 and Sumner et al., 2006. *Neurology*, 66(7):1067-73).

An increased level of SMN compared to SMNΔEx7 protein in a host cell contacted with a compound indicates that the compound is effective for use in treating or preventing SMA. Specific examples of cell culture models from patients with SMA include, but are not limited to, fibroblast, amniocyte, and chorionic villous sampling (CVS) cell cultures (see, e.g., Patrizi et al., 1999. *Eur J Hum Genet.* 7:301-309). The in vivo effect of a compound can also be assayed by performing indirect immunofluorescence analysis of nuclear gem levels to determine the compound's ability to elevate SMN proteins levels in a cell line such as SMA patient fibroblasts (see Wolstencroft et al., 2005 *Human Molecular Genetics* 14(9): 1199-1210).

Another antibody-based separation that can be used to detect the SMN, SMNΔEx7 and/or another protein encoded by SMN1 or SMN2 is the use of flow cytometry such as by a fluorescence-activated cell sorter ("FACS"). Briefly, cells are fixed, permeabilized and blocked with excess protein in a FACS buffer. The suspended mixture of cells is centrifuged and re-suspended in a FACS buffer. Antibodies which are conjugated to a fluorophore are added to allow the binding of the antibodies to specific proteins. In some embodiments, secondary antibodies that are conjugated to the fluorophores can be used to detect primary antibodies specific to the protein of interest. The cell mixture is then washed by one or more centrifugation and resuspension steps. The mixture is run through a FACS which separates the cells based on different fluorescence characteristics. FACS systems are available in varying levels of performance and ability, including multi-color analysis. The intact cells can be identified by a characteristic profile of forward and side scatter which is influenced by size and granularity, as well as by levels of expression of proteins directly or indirectly bound by the fluorochrome-conjugated antibody.

Further, the ability of a compound to affect the activity of SMN can be determined by assays that determine snRNP assembly efficiency, since it has been demonstrated that SMN is required for snRNP assembly (see Yong et al., 2004. *Trends Cell Biol* 14:226-232). snRNP assembly can be assayed by any method known to one skilled in the art.

Methods for Characterizing Compounds that Modulate Inclusion of exon 7 of SMN2 into mRNA Transcribed from the SMN2 Gene Cytotoxicity Assays Compounds may be tested for cytotoxicity in mammalian, preferably human, cell lines. In certain embodiments, cytotoxicity is assessed in one or more of the following cell lines: U937, a human monocyte cell line; primary peripheral blood mononuclear cells (PBMC); Huh7, a human hepatoblastoma cell line; HEK293T and HEK293H, human embryonic kidney cell lines; and THP-1, monocytic cells; a HeLa cell line;

fibroblasts or other cell types isolated from SMA patients; SMA patient-derived cells, e.g., the GM03813 cells, GM09677 cells, GM00232 cells, and B lymphocyte GM10684 cells; and neuroblastoma cell lines, such as MC-IXC, SK-N-MC, SK-N-MC, SK-N-DZ, SH-SY5Y and BE(2)-C. In general, many assays known to one skilled in the art can be used to assess viability of cells or cell lines following exposure to a compound and, thus, determine the cytotoxicity of the compound.

Animal Model-Based Screens

Compounds identified in the assays described herein can be tested for biological activity using animal models for SMA. Non-limiting examples include animals engineered to contain SMN coupled to a functional readout system, such as a transgenic mouse. Such animal model systems include, but are not limited to, rats, mice, chicken, cows, monkeys, pigs, dogs, rabbits, etc. In a specific embodiment, a compound is tested in a mouse model system.

The anti-SMA activity of a compound can be determined by administering the compound to an animal model and verifying that the compound is effective in reducing the severity of SMA in said animal model. Examples of animal models for SMA include, but are not limited to, SMA animal models described by Monani et al. (2000, *Human Molecular Genetics* 9(16)2451-2457) and Charlotte J. Sumner (2006, *NeuroRx* 3(2):235-245). In a specific embodiment, a mouse model expresses a human SMN1 and/or SMN2 gene.

Physiological Assays in SMA Patients

The ability of a compound or composition comprising a compound to treat SMA can be assayed by assessing muscle strength, motor function, and pulmonary function in patients diagnosed with SMA. Muscle strength can be assessed by using any method known to those skilled in the art, including, but not limited to, use of a hand held dynamometer. Muscle testing can be performed to assess right and left hand grip, right and left knee extension, right and left knee flexion, and right and left elbow flexion. Motor function can be assessed by a patient's ability to lie down, roll, sit, crawl, kneel, stand, walk, run and jump. Pulmonary function tests can be performed on patients according to American Thoracic Society standards, and include, but are not limited to maximum inspiratory pressure, maximum expiratory pressure, cough pressure, forced vital capacity, forced expiratory volume in the first second, and measurement of lung volume.

Compositions

Any compound described herein may optionally be in the form of a composition comprising the compound and an optional carrier, excipient or diluent. Other embodiments provided herein include pharmaceutical compositions comprising an effective amount of a compound and a pharmaceutically acceptable carrier, excipient, or diluent. The pharmaceutical compositions are suitable for veterinary and/or human administration. The pharmaceutical compositions provided herein can be in any form that allows for the composition to be administered to a subject.

In a specific embodiment and in this context, the term "pharmaceutically acceptable carrier, excipient or diluent" means a carrier, excipient or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a specific carrier when the pharmaceutical composition is administered intravenously. Saline solutions and aqueous dextrose and glycerol solutions can also be employed as liquid carriers, particularly for injectable solutions.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents. Further provided herein are anhydrous pharmaceutical compositions and dosage forms comprising one or more compounds of the present invention. The compositions and single unit dosage forms can take the form of solutions, suspensions, emulsion, tablets, pills, capsules, powders, sustained-release formulations and the like.

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art.

Because of their ease of administration, tablets and capsules represent the most advantageous oral dosage unit forms, in which case solid excipients are employed. In general, pharmaceutical compositions and dosage forms are prepared by uniformly and intimately admixing the active ingredients with liquid carriers, finely divided solid carriers, or both, and then shaping the product into the desired presentation if necessary.

Examples of excipients that can be used in oral dosage forms provided herein include, but are not limited to, binders, fillers, disintegrants, and lubricants.

Therapeutic Methods

The invention provides methods for enhancing the inclusion of exon 7 of SMN2 into mRNA transcribed from the SMN2 gene, comprising administering to a human subject in need thereof an effective amount of a compound or a pharmaceutical composition thereof identified as the one that increases the inclusion of exon 7 of SMN2 into mRNA transcribed from the SMN2 gene. In a specific embodiment, the invention provides a method for enhancing inclusion of exon 7 of SMN2 into mRNA transcribed from the SMN2 gene, and thus for increasing levels of SMN protein produced from the SMN2 gene, in a human subject in need thereof, comprising administering an effective amount of a compound or a pharmaceutical composition thereof to the human subject, in which said compound enhances, in vitro or in cultured cells, the amount and/or activity of a fusion protein encoded by a minigene described herein.

The present invention also provides a method for treating SMA in a human subject, comprising administering to a human subject in need thereof a compound or a pharmaceutical composition thereof identified as enhancing the inclusion of exon 7 of SMN2 into mRNA transcribed from the SMN2 gene. In a specific embodiment, the present invention provides a method for treating SMA in a human subject, comprising administering an effective amount of a compound to a human subject in need thereof, in which said compound enhances, in vitro or in cultured cells, the expression of a fusion protein encoded by a minigene described herein. In certain embodiments, the compound is not sodium vanadate. In some embodiments, the compound is not a chemotherapeutic agent. In some embodiments, the compound is not aclarubicin. In certain embodiments, the compound is not one or more of the following: riluzole, gabapentin, phenylbutyrate, hydroroxyurea, L aetyl carnitine, indoprofen, aminoglycosides, cardiotrophin 1, and histone deacetylase (HDAC) inhibitors such as, sodium butyrate, phenylbutyrate, valproic acid, suberoyl anilide hydrorxamic acid and the compounds identified by Heemskerk et al. (2207, International Patent Application No. PCT/US2007/006772). In another embodiment, the compound is a compound of Formula (I) or a form thereof.

A compound or a composition thereof may be used in conjunction with another therapy (e.g., a palliative therapy) for SMA. In a specific embodiment, two or more compounds may be used to treat SMA. In specific embodiments, a compound or a composition thereof is the only active ingredient administered to treat SMA.

In some embodiments, a compound or a pharmaceutical composition thereof that is administered to a subject enhances the inclusion of exon 7 of SMN2 into mRNA transcribed from the SMN2 gene, and thus results in a 2%, 3%, 4%, 5%, 10%, 15%, 20%, 25%, 35%, 45%, 50%, 55%, 65%, 70%, 75%, 80%, 85%, 90%, 95%, 100%, 150%, 200%, 300%, 400%, 500% or more increase in SMN protein relative to a negative control (e.g., PBS or 0.5-1.0% DMSO), as determined by a cell-based or cell-free assay described herein.

In some embodiments, a compound or a pharmaceutical composition thereof that is administered to a subject and enhances the inclusion of exon 7 of SMN2 into mRNA transcribed from the SMN2 gene, increases levels of SMN protein produced from the SMN2 gene by 2%, 3%, 4%, 5%, 10%, 15%, 20%, 25%, 35%, 45%, 50%, 55%, 65%, 70%, 75%, 80%, 85%, 90%, 95%, 100%, 150%, 200%, 300%, 400%, 500% or more relative to a negative control as determined by assays known in the art, e.g., western blotting, ELISA, flow cytometry.

In a specific embodiments, a compound or a pharmaceutical composition thereof that is administered to a subject enhances the inclusion of exon 7 of SMN2 into mRNA transcribed from the SMN2 gene by 2%, 3%, 4%, 5%, 10%, 15%, 20%, 25%, 35%, 45%, 50%, 55%, 65%, 70%, 75%, 80%, 85%, 90%, 95%, 100%, 150%, 200%, 300%, 400%, 500% or more relative to a negative control, as determined by detecting SMN2 mRNA containing exon 7 or a fragment thereof (e.g., Northern blot or RT-PCR or quantitative RT PCR).

The effective amount of a compound or a pharmaceutical composition thereof to be used depends on a number of factors, including but not limited to the type of SMA, health and age of the patient, and toxicity or side effects. The present invention encompasses methods for treating SMA for which no treatment is available. The present invention also encompasses methods for treating SMA as an alternative to conventional therapies.

The present invention also provides methods of treating SMA in a subject in need thereof, said methods comprising administering to the subject one or more of the compounds with one or more additional agents. In one embodiment, one or more compounds are administered to the subject in combination with a supportive therapy, a pain relief therapy, or other therapy that does not have an effect per se on SMA.

One or more compounds or a pharmaceutical composition thereof may be administered to a subject to treat SMA in any order. In addition, one or more compounds and one or more other therapies (e.g., therapeutic agents) may be administered in any order to a subject to treat SMA.

A combination product of one or more compounds and one or more additional agents can be administered sequentially or concurrently. For example, one or more compounds may be administered to a subject in combination with an agent that increases the transcription of the SMN2 gene.

In a specific embodiment, the combination product of the present invention may improve the therapeutic effect of the compound and the agent by functioning together to have an additive or synergistic effect. In another embodiment, the combination product of the present invention may reduce the side effects associated with each compound and agent when taken alone.

The therapeutic agents of a combination product can be administered to a subject in the same pharmaceutical composition. Alternatively, the therapeutic agents of the combination product can be administered concurrently to a subject in separate pharmaceutical compositions. The therapeutic agents may be administered to a subject by the same or different routes of administration.

Patient Population

In some embodiments, a compound or pharmaceutical composition thereof is administered to a subject suffering from SMA. In other embodiments, a compound or pharmaceutical composition thereof is administered to a subject predisposed or susceptible to SMA. In some embodiments, a compound or pharmaceutical composition thereof is administered to a subject with Type 0 SMA. In some embodiments, a compound or pharmaceutical composition thereof is administered to a subject with Type 1 SMA. In other embodiments, a compound or pharmaceutical composition thereof is administered to a subject with Type 2 SMA. In other embodiments, a compound or pharmaceutical composition thereof is administered to a subject with Type 3 SMA. In some embodiments, a compound or pharmaceutical composition thereof is administered to a subject with Type 4 SMA.

In certain embodiments, a compound or pharmaceutical composition thereof is administered to a human that has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In some embodiments, a compound or pharmaceutical composition thereof is administered to a human infant. In other embodiments, a compound or pharmaceutical composition thereof is administered to a human toddler. In other embodiments, a compound or pharmaceutical composition thereof is administered to a human child. In other embodiments, a compound or pharmaceutical composition thereof is administered to a human adult. In yet other embodiments, a compound or pharmaceutical composition thereof is administered to an elderly human.

In certain embodiments, a compound or pharmaceutical composition thereof is administered a subject in an immunocompromised state or immunosuppressed state or at risk for becoming immunocompromised or immunosuppressed. In certain embodiments, a compound or pharmaceutical composition thereof is administered to a subject receiving or recovering from immunosuppressive therapy. In certain embodiments, a compound or pharmaceutical composition thereof is administered to a subject that has cystic fibrosis, pulmonary fibrosis or another condition affecting the lungs.

In some embodiments, a compound or pharmaceutical composition thereof is administered to a patient to treat the onset of SMA in a patient at risk of developing SMA. In some embodiments, a compound or pharmaceutical composition thereof is administered to a patient who is susceptible to adverse reactions to conventional therapies. In some embodiments, a compound or pharmaceutical composition thereof is administered to a patient who has proven refractory to therapies other than compounds, but are no longer on these therapies. In certain embodiments, the patients being treated in accordance with the methods of this invention are patients already being treated with antibiotics, anti-virals, anti-fungals, or other biological therapy/immunotherapy. Among these patients are refractory patients, and patients who are too young for conventional therapies.

In some embodiments, the subject being administered a compound or pharmaceutical composition thereof has not received therapy prior to the administration of the compound or pharmaceutical composition thereof.

Mode of Administration

When administered to a patient, a compound is preferably administered as a component of a composition that optionally comprises a pharmaceutically acceptable carrier, excipient or diluent. The composition can be administered orally, or by any other convenient route, for example, by infusion or bolus injection, by absorption through epithelial or mucocutaneous linings (e.g., oral mucosa, rectal, and intestinal mucosa) and may be administered together with another biologically active agent. Administration can be systemic or local. Various delivery systems are known, e.g., encapsulation in liposomes, microparticles, microcapsules, capsules, and can be used to administer the compound.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of a compound into the bloodstream. In a specific embodiment, a compound is administered orally.

Dosage and Frequency of Administration

The amount of a compound that will be effective in the treatment of SMA can be determined by standard clinical techniques. In vitro or in vivo assays may optionally be employed to help identify optimal dosage ranges. The precise dose to be employed will also depend, e.g., on the route of administration, the type of SMA, and the seriousness of the SMA, and should be decided according to the judgment of the practitioner and each patient's or subject's circumstances.

Exemplary doses of a compound include milligram (mg) or microgram (μg) amounts per kilogram (Kg) of subject or sample weight per day (e.g., from about 1 μg per Kg to about 500 mg per Kg per day, from about 5 μg per Kg to about 100 mg per Kg per day, or from about 10 μg per Kg to about 100 mg per Kg per day. In specific embodiments, a daily dose is at least 0.1 mg, 0.5 mg, 1.0 mg, 2.0 mg, 5.0 mg, 10 mg, 25 mg, 50 mg, 75 mg, 100 mg, 150 mg, 250 mg, 500 mg, 750 mg, or at least 1 g. In another embodiment, the dosage is a unit dose of about 0.1 mg, 1 mg, 5 mg, 10 mg, 50 mg, 100 mg, 150 mg, 200 mg, 250 mg, 300 mg, 350 mg, 400 mg, 500 mg, 550 mg, 600 mg, 650 mg, 700 mg, 750 mg, 800 mg or more. In another embodiment, the dosage is a unit dose that ranges from about 0.1 mg to about 1000 mg, 1 mg to about 1000 mg, 5 mg to about 1000 mg, about 10 mg to about 500 mg, about 150 mg to about 500 mg, about 150 mg to about 1000 mg, 250 mg to about 1000 mg, about 300 mg to about 1000 mg, or about 500 mg to about 1000 mg. In another embodiment, a subject is administered one or more doses of an effective amount of a compound or a composition, wherein the effective amount is not the same for each dose.

Combination Products

Additional agents that can be used in a combination product with compounds of the present invention for the treatment of SMA include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules. Specific examples of such agents include, but are not limited to, immunomodulatory agents (e.g., interferon), anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steriods, and non-steriodal anti-inflammatory drugs (e.g., aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents (e.g., nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, and AZT) and antibiotics (e.g., dactinomycin (formerly actinomycin), bleomycin, erythomycin, penicillin, mithramycin, and anthramycin (AMC)).

Any therapy which is known to be useful, or which has been used, will be used or is currently being used for the treatment of SMA can be used in combination with compounds in accordance with the invention described herein. Therapeutics that can be used in combination with compounds include, but are not limited to riluzole, gabapentin, phenylbutyrate, hydroroxyurea, L aetyl carnitine, indoprofen, aminoglycosides, cardiotrophin 1, and histone deacetylase (HDAC) inhibitors such as, sodium butyrate, phenylbutyrate, valproic acid, suberoyl anilide hydrorxamic acid (see, e.g., Charlotte J. Sumner, 2006. NeuroRx, 3(2):235-245). In one embodiment, therapeutics that can be used in combination with compounds include these agents identified by Heemskerk et al. (2207, International Patent Application No. PCT/US2007/006772). In certain embodiments, therapeutics that can be used in combination with compounds include, but are not limited to, a chemotherapeutic and sodium vandate. In certain embodiments, the therapeutics that can be used in combination with compounds include aclarubicin.

Kits

The present invention provides kits comprising a nucleic acid construct described herein, in one or more containers, and instructions for use. In a specific embodiment, a kit comprises, in a container, a nucleic acid construct comprising a minigene, wherein the minigene comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 of SMN or a fragment thereof and a fragment of the nucleic acid residues of exon 8 of SMN, wherein either a single adenine, thymine or cytosine is inserted after nucleic acid residues of exon 7 of SMN2 or a fragment thereof, or a single nucleotide is inserted after nucleic acid residue 45, 46 or 47 of exon 7 of SMN2 or a fragment thereof, and (ii) a reporter gene fused in frame to the nucleic acid residues of exon 8 of SMN or a fragment thereof, wherein the reporter gene does not have a start codon. In a specific embodiment, the minigene has a start codon (e.g., ATG or a non-canonical start codon) added to the 5' end of exon 6 of SMN or a fragment thereof.

In a specific embodiment, a kit comprises, in a container, a nucleic acid construct comprising a minigene, wherein the minigene comprises, in 5' to 3' order: the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2. In one aspect, the minigene comprises a start codon 5' to the nucleic acid residues of exon 6 of SMN, wherein the first codon of the coding sequence of the reporter gene and the start codon of the minigene are in the same open reading frame.

In a specific embodiment, a kit comprises, in a container, a nucleic acid construct comprising a minigene, wherein the minigene comprises, in 5' to 3' order: the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first start codon of the fragment of the nucleic acid residues of exon 6 of SMN and the first codon of the coding sequence of the reporter gene are in the same open reading frame.

In a specific embodiment, a kit comprises, in a container, a nucleic acid construct comprising a minigene, wherein the minigene comprises, in 5' to 3' order: a start codon, the nucleic acid residues of exon 6 of SMN or a fragment thereof, the nucleic acid residues of intron 6 of SMN or a fragment thereof, the nucleic acid residues of exon 7 of SMN2, the nucleic acid residues of intron 7 of SMN or a fragment thereof, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2, and wherein the first codon of the coding sequence of the reporter gene and the first start codon of the minigene are in the same open reading frame.

In a specific embodiment, a kit comprises, in a container, a nucleic acid construct comprising a minigene, wherein the minigene comprises, in 5' to 3' order: nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first amino acid sequence include a start codon; (iii) the nucleic acid residues encoding the first and second amino acid sequences permit removal of an intron via mRNA splicing, and (iv) the first codon of the coding sequence of the reporter gene and the start codon of the nucleic acid residues encoding the first amino acid sequence are in the same open reading frame.

In a specific embodiment, a kit comprises, in a container, a nucleic acid construct comprising a minigene, wherein the minigene comprises, in 5' to 3' order: a start codon, nucleic acid residues encoding a first amino acid sequence, the nucleic acid residues of intron 6 of SMN or a fragment thereof, the nucleic acid residues of exon 7 of SMN2, the nucleic acid residues of intron 7 of SMN or a fragment thereof, nucleic acid residues encoding a second amino acid sequence, and the nucleic acid residues of the coding sequence of a reporter gene lacking a start codon, wherein (i) either a single adenine, thymine or cytosine residue is inserted after nucleic acid residue 48 of the nucleic acid residues of exon 7 of SMN2, or a single nucleotide is inserted after nucleic acid residue 45, 46 or 47 of exon 7 of SMN2; (ii) the nucleic acid residues encoding the first and second amino acid sequences permit removal of an intron via mRNA splicing, and (iii) the first codon of the coding sequence of the reporter gene and the first start codon of the minigene are in the same open reading frame.

In some embodiments, a kit further comprises a positive and/or negative control nucleic acid construct such as described herein.

In one embodiment, the positive control nucleic acid construct comprises a minigene, wherein the minigene comprises, in 5' to 3' order: (i) a nucleic acid residues of exon 6 of SMN or a fragment thereof, the nucleic acid residues of intron 6 of SMN or a fragment thereof, the nucleic acid residues of exon 7 of SMN1 or a fragment thereof, the nucleic acid residues of intron 7 of SMN or a fragment thereof, and a fragment of the nucleic acid residues of exon 8 of SMN, wherein either a single adenine, thymine or cytosine residue is inserted after nucleic acid residue 48 of exon 7 of SMN1, or a single nucleotide is inserted after nucleic acid residue 45, 46 or 47 of exon 7 of SMN1; and (ii) a reporter gene fused in frame to the nucleic acid residues of exon 8 of SMN or a fragment thereof, wherein the reporter gene does not have a start codon. In a specific embodiment, the minigene has a start codon added to the 5' end of exon 6 of SMN or a fragment thereof.

In another embodiment, the positive control nucleic acid construct comprises a minigene, wherein the minigene comprises, in 5' to 3' order: a start codon, the nucleic acid residues of exon 6 of SMN, the nucleic acid residues of intron 6 of SMN, the nucleic acid residues of exon 7 of SMN1, the nucleic acid residues of intron 7 of SMN, a fragment of exon 8 of SMN, and the nucleic acid residues of the coding sequence of a reporter gene lacking a start codon, wherein either a single adenine, thymine or cytosine residue is inserted after nucleic acid residue 48 of the nucleic acid residues of exon 7 of SMN1, or a single nucleotide is inserted after nucleic acid residue 45, 46 or 47 of exon 7 of SMN1, and wherein the first codon of the coding sequence of the reporter gene and the start codon of the minigene are in the same open reading frame. In certain embodiments, the nucleic acid constructs recited herein where a single adenine, thymine, or cytosine residue is inserted after nucleic acid residue 48 of the nucleic acid residues of exon 7 of SMN2 or a single nucleotide is inserted after nucleic residue 45, 46, or 47 of the nucleic acid residues of exon 7 of SMN2, the nucleic acid residues of exon 7 of SMN1 may be used instead to generate a positive control.

In one embodiment, the negative control nucleic acid construct comprises a minigene, wherein the minigene comprises, in 5' to 3' order: (i) the nucleic acid residues of exon 6 of SMN or a fragment thereof, the nucleic acid residues of intron 6 of SMN or a fragment thereof, the nucleic acid residues of exon 7 of SMN2 or a fragment thereof, the nucleic acid residues of intron 7 or a fragment thereof, and a fragment of the nucleic acid residues of exon 8 of SMN, wherein a guanine is inserted after nucleic acid residue 48 of exon 7 of SMN2, and (ii) a reporter gene fused in frame to the nucleic acid residues of exon 8 of SMN or a fragment thereof, wherein the reporter gene does not have a start codon. In a specific embodiment, the minigene has a start codon added to the 5' end of the nucleic acid residues of exon 6 of SMN or a fragment thereof.

In another embodiment, the negative control nucleic acid construct comprises a minigene, wherein the minigene comprises, in 5' to 3' order: a start codon, the nucleic acid residues of exon 6 of SMN, the nucleic acid residues of intron 6 of SMN, the nucleic acid residues of exon 7 of SMN2, the nucleic acid residues of intron 7 of SMN, a fragment of exon 8 of SMN, and the nucleic acid residues of the coding sequence of a reporter gene lacking a start codon, wherein a guanine is inserted after nucleic acid residue 48 of exon 7 of SMN2, and wherein the first codon of the coding sequence of the reporter gene and the start codon of the minigene are in the same open reading frame. In certain embodiments, as a negative control, the nucleic acid constructs recited herein contain a single guanine after nucleic acid residue 48 of the nucleic acid residues of exon 7 of SMN2 rather than a single adenine, thymine, or cytosine residue inserted after nucleic acid residue 48 of the nucleic acid residues of exon 7 of SMN2 or a single nucleotide inserted after nucleic residue 45, 46, or 47 of the nucleic acid residues of exon 7 of SMN2.

In some embodiments, a kit further comprises a positive and/or negative control agent. For example, in one embodiment, the negative control agent is DMSO or PBS. In another embodiment, the positive control is a compound of Formula (I) or a form thereof.

In some embodiments, a kit further comprises components for in vitro transcription. In some embodiments, a kit further comprises a cell-free extract.

Systems

Presented herein are systems comprising a kit or a component(s) of the kits presented herein and a computer program product for use in conjunction with a computer system. In such systems, the computer program product can comprise a computer readable storage medium and a computer program mechanism embedded therein. The computer program mechanism may comprise instructions for evaluating the amount or activity of a fusion protein encoded by a nucleic acid construct described herein. The computer program mechanism may comprises instructions for evaluating the amount of a mRNA transcript containing exon 7 of SMN2 or a fragment thereof transcribed from a minigene or the SMN2 gene.

EXAMPLES

Cryptic Splice Site

This example demonstrates that insertion of a guanine residue inserted after nucleotide 48 of exon 7 of SMN2 in a nucleic acid construct of the present invention results in the creation of a cryptic splice site. As a result, such a construct does not reproduce the splicing reaction that occurs at the 5' splice site of intron 7 of SMN2, and thus, the construct cannot be used to screen for compounds that may modulate the inclusion of exon 7 of SMN2 into mRNA transcribed from the SMN2 gene.

Materials and Methods
Preparation of the Minigene Constructs

DNA corresponding to a region of the SMN2 gene starting from the 5' end of exon 6 (ATAATTCCCCC) (SEQ ID No.: 1) and ending at nucleic acid residue 23 of exon 8 (CAGCAC) (SEQ ID No.: 2) was amplified by PCR using the following primers:

```
Forward primer:
                                    (SEQ ID No.: 3)
5'-CGCGGATCCATAATTCCCCCACCACCTC-3'

Reverse primer:
                                    (SEQ ID No.: 4)
5'-CGCGGATCCGTGCTGCTCTATGCCAGCA-3'
```

The 5' end of each primer was designed to add a BamHI site at both the 5' end of exon 6 (GGATCC) (SEQ ID No.:5) and the 3' end after the 23$^{rd}$ nucleotide of exon 8. Using the BamHI restriction sites, the PCR fragment was cloned into a derivative of the original pcDNA 3.1/Hygro vector which was modified as disclosed in United States Patent Publication US2005/0048549.

New UTRs were added to the modified vector using the HindIII site and the BamHI site comprising a 5"DEG UTR: 5'-TAGCTTCTTACCCGTACTCCACCGTTG-GCAGCACGATCGCACGTCCCACGT GAACCATTGG-TAAACCCTG-3' (SEQ ID No.: 6) was cloned into the modified pcDNA3.1/Hygro vector together with a start codon upstream of the BamHI site; and a 3'DEG UTR:
5'-ATCGAAAGTACAGGACTAGCCTTCCTAG-CAACCGCGGGCTGGGAGTCTGA GACATCACTCAA-GATATATGCTCGGTAACGTAT-GCTCTAGCCATCTAACTAT
TCCCTATGTCTTATAGGG-3' (SEQ ID No.: 7) was cloned into the modified pcDNA3.1/Hygro vector using the NotI site and the XhoI site with a stop codon immediately downstream of the NotI site. In addition, a luciferase gene lacking its start codon was cloned into the vector using the BamHI and NotI sites.

The resulting minigene comprises, in 5' to 3' order: the 5'-DEG UTR, the start codon, six additional nucleotides forming a BamHI site, the nucleic acid residues of exon 6, the nucleic acid residues of intron 6 of SMN2, the nucleic acid residues of exon 7 of SMN2, the nucleic acid residues of intron 7 of SMN2, and the first 23 nucleic acid residues of exon 8 of SMN2, an additional six nucleotides forming a BamHI site and the luciferase gene lacking the start codon.

A single adenine, thymine, cytosine or guanine residue was inserted after nucleotide 48 of exon 7 of SMN2 by site-directed mutagenesis. The different minigene constructs produced are referred to by the respective nucleotide that was inserted as SMN2-A, SMN2-T, SMN2-C and SMN2-G, respectively.

To generate the SMN1 version of the minigene, the sixth nucleotide of exon 7 (a thymine residue) was changed to cytosine using site directed mutagenesis.

The modification was performed for all versions of the SMN2 minigene construct (SMN2-A, SMN2-T, SMN2-C and SMN2-G) to provide the resulting SMN1 minigene constructs referred to as SMN1-A, SMN1-T, SMN1-C and SMN1-G, respectively.

Results

SMN1 and SMN2 transcripts derived from minigenes containing exon 6 through 8 and the intervening introns recapitulate the splicing of their endogenous pre-mRNAs (Lorson et al, 1999, Proc. Natl. Acad. Sci. U.S.A. 96(11):6307-6311). An SMN2-alternative splicing reporter construct which contains exons 6 to 8 and the intervening introns followed by a luciferase reporter gene was generated. Salient features of this construct are the lack of the start codon in the luciferase gene, inactivation of the termination codon (in the open reading frame that encodes the SMN protein) of exon 7 by insertion of a nucleotide after nucleic acid 48 of exon 7 and addition of a start codon (ATG) immediately upstream of exon 6. Four versions of the SMN2 minigene were generated in which a single adenine (SMN2-A), thymine (SMN2-T), cytosine (SMN2-C) or guanine (SMN2-G) residue was inserted after nucleic residue 48 of exon 7.

Figure 1:
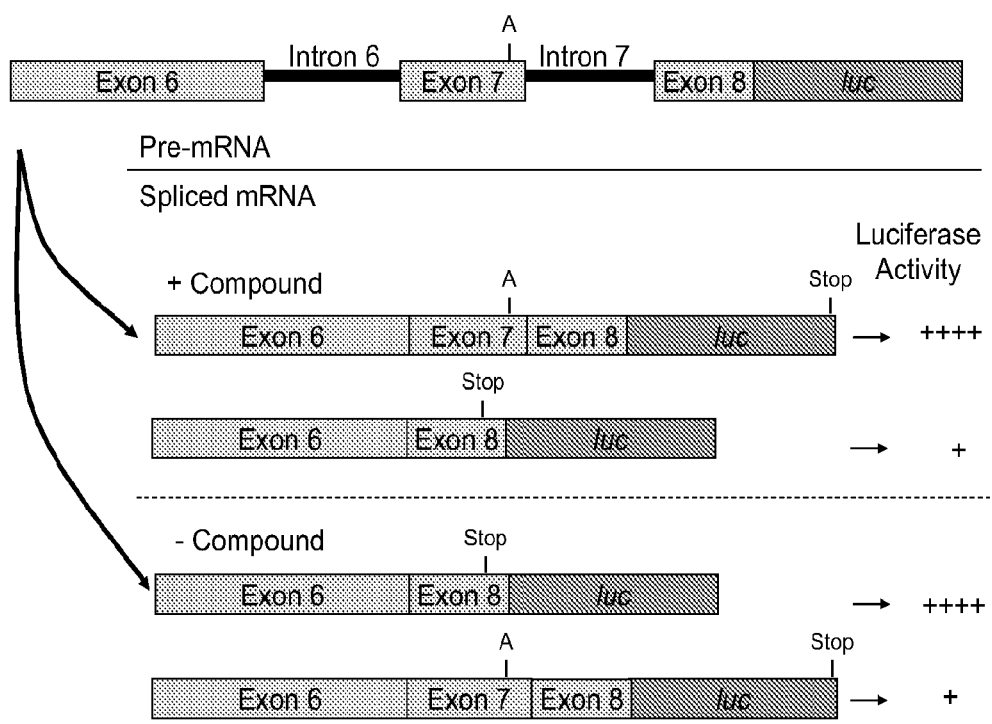
FIG. 1: Schematic drawing of the SMN2 minigene construct, its features and its two alternatively spliced mRNA transcripts. The nucleotide added to exon 7 of SMN2 after nucleic residue 48 is indicated by the letter "A," which could be adenine, cytosine, or thymine. In the presence of a compound that increases the inclusion of exon 7 of SMN2 into mRNA transcribed from the SMN2 gene, the luciferase gene will be in frame with the SMN2 minigene after splicing due to the inclusion of exon 7 and a fusion protein with luciferase activity will be produced. When exon 7 is excluded (i.e., in the absence of a compound that enhances the inclusion of exon 7 of SMN2 into mRNA transcribed from the SMN2 gene), a frameshift is created in exon 8 of SMN resulting in the luciferase gene being out of frame. The frameshift will also result in a nonsense codon in exon 8 of SMN2 resulting in termination of translation. Thus, a truncated SMN protein will be made that does not include the luciferase portion. Therefore, the luciferase activity detected in the presence of the compound will be higher than the luciferase activity detected in the absence of the compound or the presence of a negative control (e.g., PBS or DMSO). A stop codon(s) is/are indicated by "Stop."

The SMN2 minigene was designed such that the luciferase reporter is in frame with the ATG codon immediately upstream of exon 6 when exon 7 is present in the mRNA and the luciferase reporter is out of frame with the ATG codon immediately upstream of exon 6 if exon 7 of SMN2 is removed during splicing of the pre-mRNA. In addition, in the absence of exon 7, the open reading frame that starts from the ATG codon immediately upstream of exon 6 contains a stop codon in the fragment of exon 8 of SMN. Thus, in the presence of compounds that increase the inclusion of exon 7 of SMN2 into mRNA transcribed from the SMN2 gene, more transcripts containing exon 7 and more functional reporter are produced. A schematic illustration of this description can be found in FIG. 1.

The DNA sequence of the minigene from the SMN2-G construct is provided in FIG. 2. The DNA sequence of the minigene from the SMN2-A construct is provided in FIG. 3.

SMN1 versions of the four SMN2 minigene constructs were also generated in which the sixth nucleotide (T) of exon 7 was mutated to C. Similarly to the SMN2 minigene constructs, the four versions of the SMN1 minigene construct had a single adenine (SMN1-A), thymine (SMN1-T), cytosine (SMN1-C) or guanine (SMN1-G) residue inserted after nucleic residue 48 of exon 7.

To validate the splicing pattern of the SMN2-alternative splicing reporter construct and to determine the maximum ratio of expression between SMN1 and SMN2 minigene constructs, corresponding SMN1- and SMN2-minigene constructs were transiently transfected into HEK293H cells, and the expression levels of the fusion protein encoded by the minigene were compared by measuring luciferase activity. A 4-fold increase in luciferase expression was detected for the SMN1-A, SMN1-T and SMN1-C versions of the minigene construct (FIG. 4) when compared to the SMN2-A, SMN2-T and SMN2-C minigene constructs, respectively. In contrast, the SMN1-G minigene construct did not exhibit an increase in luciferase expression when it was compared to the SMN2-G minigene construct.

In order to determine why constructs with a guanine insert yielded results different from those obtained with constructs that had an adenine, thymidine or cytosine insert after nucleic acid residue 48 of exon 7 of SMN2, total RNA was isolated from cells transiently transfected with the SMN1 or SMN2 versions of the minigenes. Total RNA was reverse transcribed to produce cDNA. The cDNA was then amplified by PCR with primers specific for the minigene/reporter gene transcript. The first primer annealed to the luciferase gene and the second primer to exon 6. The PCR products were resolved on a 2% agarose gel.

RNA isolated from HEK293H cells transfected with the SMN2-G, SMN2-A, SMN2-T or SMN2-C minigene construct predominately showed a band corresponding to the size of a transcript that lacks exon 7. Expression of the SMN1-G, SMN1-A, SMN1-T and SMN1-C minigene construct in transiently transfected HEK293H cells resulted in the appearance of an additional band corresponding to the transcript containing exon 7. The size of the band containing exon 7 was similar for all SMN1 versions of the minigene. The band corresponding to the transcript containing exon 7 produced from the SMN1-G minigene construct was isolated and cloned into a pCR-blunt vector (Invitrogen). 20 clones containing the SMN1-G minigene fragment were sequenced. All of the clones lacked seven nucleotides from the inserted guanine residue to the last nucleotide of exon 7 (GTAAGGA) (SEQ ID No.: 8) demonstrating that the inclusion of exon 7 for the SMN1-G version of the minigene occurred through utilization of a cryptic splice site generated by the G insertion. Indeed, the G insertion resulted in generation of a sequence element (GTAAGG) (SEQ ID No.: 9) reminiscent of the 5' end of intron 7 (GTAAGT) (SEQ ID No.: 10). Therefore, the spliceosome preferentially used the 5' splice site between the nucleotide residue 48 of exon 7 and the G insertion (position 49). Utilization of the cryptic splice site resulted in a frameshift of the open reading frame that starts at the ATG immediately upstream of exon 6 of SMN as well as a stop codon before the luciferase portion of the minigene. Therefore, luciferase expression was substantially reduced from the SMN1-G minigene construct when a part of exon 7 was included. Analogously, the G insertion in the SMN2-G minigene construct creates a cryptic splice site in exon 7 of SMN2. The resulting inclusion of a fragment of exon 7 of SMN2 that lacks seven nucleotides at the 3' end significantly reduces luciferase expression from the SMN2-G minigene construct.

Compounds that Enhance the Inclusion of exon 7 of SMN2 into mRNA Transcribed from the SMN2 Gene This example demonstrates the successful identification of compounds that increase the inclusion of exon 7 of SMN2 into mRNA transcribed from the SMN2 gene using the cell-based assays and nucleic acid constructs described herein.

Materials and Methods

Preparation of the Stable Cell Line

HEK293H cells were stably transfected with an SMN2 nucleic acid construct described herein. The examples provided herein demonstrate a standard procedure for making stable cell lines using a lipid-medium transfection reagent. Standard safety precautions (e.g. use of tissue culture hood and the like) were followed in carrying out the procedures described herein.

On Day 1, HEK293H cells were plated in a six well plate at a concentration of $5\times10^5$ cells per well in a volume of 2 mL of nonselective medium (DMEM containing 10% fetal bovine serum and 100 units/mL penicillin and streptomycin). For each construct, two wells were prepared, one well for the transfection plus one additional well as a DNA-free control. The cells were allowed to adhere for at least three hours in an incubator set to 37° C. and 5% $CO_2$. For each transfection, 100 µL of a nonselective medium, 6 µL of FuGENE6 reagent (Roche #1814443) and 2 µg of DNA were sequentially added to a sterile microcentrifuge tube, mixed gently and allowed to incubate at room temperature for 15 minutes. During the incubation time, the medium in the wells of the 6-well plate was removed and replaced with 1 mL of fresh nonselective medium. After a 15 minutes incubation, the FuGENE6/DNA mixture was added dropwise to the designated well. The plate was gently swirled before being returned to the incubator.

On Day 2, the medium was removed from each of the wells and replaced with 2 mL of fresh nonselective medium. The plates were then returned to the incubator.

On Day 3, the medium was removed from each of the wells. The cells were then rinsed with 1 mL sterile PBS and trypsinized with 0.25% trypsin-EDTA for counting. 500 µL of trypsin was added per well. After the cells were dislodged from the bottom of each well and 4.5 mL of medium was added, then the entire contents of each well was transferred to a sterile 15 mL tube. 100 µL of the trypsinized cells were mixed with 100 µL of Trypan Blue stain and counted on a haemocytometer. For each minigene nucleic acid construct, two 10 $cm^2$ dishes were plated. 5000 cells/mL were plated in a final volume of 10 mL nonselective medium. The cells were returned to the incubator and incubated overnight.

On Day 4, 10 mL of nonselective medium containing 400 µg/mL hygromycin was added to each 10 $cm^2$ dish, bringing the final volume of medium in each dish to 20 mL with a final hygromycin concentration of 200 µg/mL. The cells were incubated for an additional 3 days.

Following the 3-day additional incubation period, the medium was replaced with 10 mL of fresh selective medium (DMEM containing 10% FBS, 100 units/mL penicillin and streptomycin and 200 µg/mL hygromycin). This was repeated every 2-3 days. After about 10 days, the colonies had grown to a size visible to the unaided eye.

Once the colonies had grown to a suitable size, without adjacent colonies growing into each other, the colonies were picked using 3 mm cloning disks. The cloning disks were allowed to soak for several minutes in trypsin. During this time, 0.5 mL of selective medium was added to each well of a 24-well plate.

The medium was removed from the 10 $cm^2$ dishes. The colonies were washed briefly with 5 mL PBS, and the PBS was promptly removed. Using forceps, a trypsin-soaked disk was lifted, and excess trypsin was removed by shaking. Each disk was carefully placed on a single colony on the plate. The colony was then trypsinized to the disk for about 5 minutes. The disk was then carefully removed and placed into one of the wells of the 24-well plate. This process was repeated until the desired number of colonies were prepared. Care was taken to soak the forceps in trypsin in-between. Once all of the desired colonies had been transferred, the 24-well plate was placed in the incubator. The medium of the 24-well plate was carefully changed every three days, while keeping the disks in the wells. After about 1-2 weeks, the cells in the wells had reached confluency and were transferred to a larger plate. The clones were then tested for reporter gene activity. Clones with the expected characteristics were frozen down in 90% FBS+ 10% DMSO.

Expansion of Cells

Stable HEK293H cell lines containing the SMN2-A minigene construct were cultured in DMEM supplemented with 10% FBS and 200 µg/mL hygromycin in T175 flasks. The cells were subcultured every 4 days at 1:10 dilution. Cultures were kept in a 37° C. and 5% $CO_2$ incubator.

The cells were scaled-up three days before performing the high-throughput screen (HTS). Cells from two confluent T175 flasks were subcultured into 20 T175 flasks (1:10 dilution). Cells were harvested from each confluent flask by removing all of the medium and adding 4 mL of warmed trypsin to dislodge the cells. After the cells were dislodged, 16 mL of selective medium was added for a final volume of 20 mL. The cells were expanded by adding 2 mL of the harvested cells into ten new T175 flasks plus 25 mL of selective medium. The twenty new flasks were placed into the 37° C., 5% $CO_2$ incubator.

On the day the HTS was performed, the medium was removed from the flasks and 3 mL of warmed trypsin was added to dislodge the cells. After the cells were dislodged, 10 mL of nonselective medium was added to the flask. This was repeated for all twenty flasks, and the harvested cells were combined in one flask.

100 µL of the harvested cells were added to 100 µL of Trypan Blue stain and counted on a hemocytometer. The four corner squares were counted and the numbers averaged. The average number was doubled to account for the trypan blue dilution (e.g. 110+105+106+111=432/4=108×2=216, therefore, the cell culture concentration was $216\times10^4$ cells/mL). The volume of cells needed for screening 100 plates by HTS was 1700 mL.

To plate 10,000 cells/well in a volume of 38 µL, the concentration (cells/µL) was calculated: 10,000 cells/38 µL=263.15 cells/4. The total number of cells required was also calculated: (263.15 cells/µL)(1000 µL/mL)(1700 mL)=$4.47\times10^8$ cells. The volume of concentrated cells required was also calculated: $4.47\times10^8$ cells/$216\times10^4$ cells/mL=206.9 mL of concentrated cells in a final volume of 1700 mL with nonselective medium. 38 µL of cells were plated in 384-well plates for HTS in the presence of 2 µL of test compound (final concentration=3.75 µg/mL with 0.5% DMSO).

Preparation of Standard Plates

Four standard 96-well clear Matrix Screen Mates plates were used to prepare 100 plates. 459 µL of 100% DMSO was added to make a 100 mM solution. A fresh 30 mL 10% DMSO stock solution was made by adding 3 mL of 100% DMSO to 27 mL water. The 10% DMSO was used to make serial dilutions of a puromycin stock solution so that the DMSO concentration remained at 10%.

Using standard techniques known to one skilled in the art, puromycin was serially diluted to provide 10 mM Stock in 10% DMSO (by diluting 100 µA, of 100 mM Stock with 900 µL water), 1 mM Stock in 10% DMSO (by diluting 500 µL of 10 mM Stock with 4.5 mL 10% DMSO), 400 µM Stock in 10% DMSO (by diluting 1.6 mL of 1 mM Stock with 2.4 mL 10% DMSO, 20 µM was final amount used in assay), 200 µM Stock in 10% DMSO (by diluting 1 mL of 400 µM Stock with 1 mL 10% DMSO, 10 µM was final amount used in assay), 100 µM Stock in 10% DMSO (by diluting 1 mL of 200 µM Stock with 1 mL 10% DMSO, 5 µM was final amount used in assay), 50 µM Stock in 10% DMSO (by diluting 1 mL of 100 µM Stock with 1 mL 10% DMSO, 2.5 µM was final amount used in assay), 25 µM Stock in 10% DMSO (by diluting 1 mL of 50 µM Stock with 1 mL 10% DMSO, 1.25 µM was final amount used in assay), 12.5 µM Stock in 10% DMSO (by diluting 1 mL of 25 µM Stock with 1 mL 10% DMSO, 0.625

µM was final amount used in assay), 6.25 µM Stock in 10% DMSO (by diluting 1 mL of 12.5 µM Stock with 1 mL 10% DMSO, 0.312 µM was final amount used in assay), 3.125 µM Stock in 10% DMSO (by diluting 1 mL of 6.25 µM Stock with 1 mL 10% DMSO, 0.156 µM was final amount used in assay) and 1.56 µM Stock in 10% DMSO (by diluting 1 mL of 3.125 µM Stock with 1 mL 10% DMSO, 0.078 was final amount used in assay).

Firefly Luciferase Substrate Preparation

Steadylite or Britelite (Perkin Elmer) was used to prepare the firefly luciferase substrate. Screening 100 plates required 850 mL of Steadylite, Britelite, or BrightGlo, which required 17 bottles of powdered substrate. Two 500 mL bottles of Steadylite or Britelite buffer were thawed at 4° C. overnight. The powdered substrate was resuspended by adding 50 mL of buffer to each bottle which were then combined to make one solution. 1.7 mL of 1 M $MgCl_2$ solution was added to 850 mL of Steadylite or BriteLite for a final concentration of 2 mM $MgCl_2$. 20 µL Steadylite or Britelite was added to each well of the 384-well plates, and the plates were incubated at room temperature for about 2 minutes. Immediately following, luciferase activity was read with a ViewLux Imaging system (Perkin Elmer).

Compound Identification and Validation

The HEK293H cell line stably transfected with the SMN2-A minigene construct was utilized in the HTS. HTS was performed by plating 10,000 cells in each well of a 384-well plate. Each 384-well plate contained 64 control wells used as an internal standard: 16 wells were used as a total control (no test compound, only compound solvent), 16 wells were used as reference standards representing background readings (high inhibitor concentration) and 32 wells were prepared to provide an 8-point dose response curve of puromycin as a non-specific standard control inhibitor. The remaining 320 wells contained individual test compounds. The cells were grown overnight in the presence of test compounds or controls at 37° C. in 5% $CO_2$. After 24 hours, the amount of luminescence was determined using a ViewLux Imaging system (Perkin Elmer).

Results

Using the SMN2-A minigene construct, a HTS was performed testing a compound library. The amount of the fusion protein expressed from the minigene construct was determined by measuring luciferase activity as described herein. A test compound which did not change the expression of the fusion protein was set to 100% activity; a compound that reduced the signal detected from the fusion protein to the same extent as 20 µM of puromycin was denoted as having 0% activity, and a compound that increased the signal detected from the fusion protein to the level twice that of the DMSO-treated cells comprising the SMN2-A minigene construct was considered to have 200% activity. Enhancers of fusion protein expression were defined as those compounds that increased luciferase activity by at least three standard deviations above the mean. Based on this analysis, test compounds of Formula (I) were identified as hits and were subsequently confirmed by testing the compounds under the same conditions as in the original HTS. To ensure that the increase in luciferase activity detected in the HTS was due to increased inclusion of exon 7 of SMN2 into mRNA transcripts from the SMN2-A minigene construct, each compound was tested in two different cell lines: the cell line, which was used in the original HTS (HEK293H containing the SMN2-A minigene construct), and a HEK293H cell line that contained the SMN2-G minigene construct. Due to the presence of a cryptic splice site in exon 7 of SMN2 in the SMN2-G minigene construct, the second cell line did not demonstrate luciferase activity despite the inclusion of exon 7 of SMN2 in the mRNA transcripts transcribed from the SMN2-G minigene. Accordingly, comparison of the SMN2-A minigene construct and the SMN2-G minigene construct validated the activity of compounds that specifically increased inclusion of exon 7 of SMN2 into mRNA transcribed from the SMN2 gene.

The data obtained from the reconfirmation with these two cell lines was analyzed to identify and validate compounds that upregulated expression of the fusion protein in the cell line comprising the SMN2-A minigene construct, but not in the cell line comprising the SMN2-G minigene construct. Each compound was tested at four concentrations: 15 µM, 3 µM, 0.6 µM, 0.12 µM.

Assessment of Inclusion of exon 7 of SMN2 into mRNA Transcribed from the SMN2 Minigene Construct by Quantitative PCR This example demonstrated that increased luciferase activity from the SMN2-A minigene nucleic acid construct was due to increased inclusion of exon 7 of SMN2 in the mRNA transcripts of the minigene.

Materials and Methods

HEK293H cells stably transfected with the SMN2-A minigene construct were treated with test compounds. 7500 cells/well were seeded in 50 µL of medium (DMEM plus 10% FBS, without hygromycin) in 96-well flat-bottom plates. After seeding the cells, the plate was swirled immediately to ensure proper dispersal of cells, so that an even monolayer of cells was formed. Cells were allowed to attach for at least 2-4 hrs. Then 50 µl of a 2× compound solution (DMEM plus 10% FBS and compound at 2× concentration) was added to each well, and the plate was incubated at 37° C. for 48 hrs.

At the end of the incubation period, total RNA was harvested and purified using a commercially available kit. The extracted RNA was stored at –80° C. The purified total RNA was reverse transcribed into cDNA using a commercially available kit and random hexamers as primers. The resulting cDNA was stored at –20° C.

Real-time PCR Assay was performed using RealPlex 4 thermocycler (Eppendorf) and a suitable combination of the following primers and probes:

```
SMN 5' primer:
                                        (SEQ ID No. 11)
GAAGGAAGGTGCTCACATT
or
                                        (SEQ ID No. 12)
GAAGGAAGGTGCTCACATTCC.

SMN 3' primer:
                                        (SEQ ID No. 13)
GAAGACGCCAAAAACATAAAGA
or
                                        (SEQ ID No. 14)
GATGGAACCGCTGGAGAG
or
                                        (SEQ ID No. 15)
ATAGCTTCTGCCAACCGAAC.

SMN Probe:
                                        (SEQ ID No. 16)
6FAM-AAGGAGAAATGCTGGCATAGAGCAGC-TAMRA
or
                                        (SEQ ID No. 17)
6FAM-ATATAAGGAGAAATGCTGGCATAGAGCAGC-TAMRA
or
                                        (SEQ ID No. 18)
6FAM-ATATAAGGAGAAATGCTGGCATAGAGC-TAMRA.
```

The positions of the primers and the probe on the minigene construct are depicted in FIG. 5.

SMN 5' and 3' primers were used at final concentrations of 0.3 µM. The SMN probe was used at final concentration of 0.15 µM. Human GAPDH primers and probes were purchased from Applied Biosystems (Catalog No. 4310884E). A human GAPDH primer was prepared as a pre-developed assay reagent (GAPDH-PDAR) for gene expression. A human GAPDH probe was labeled with VIC/TAMRA to serve as an endogenous reference control. The 2× qPCR Supermix UDG from Invitrogen (Catalog No. 11730-017) was used as the Real-Time PCR Mix. Each of the foregoing materials were used to prepare a SMN-GAPDH Mix (20 µL total volume) by combining 2× Supermix (10 µL), 20× GAPDH-PDAR (1 µL), water (3.85 µL), cDNA (5 µL), 100 uM 5' primer (0.06 µL), 100 uM 3' primer (0.06 µL) and 100 uM probe (0.03 µL). Each PCR cycle was carried out at the following temperatures for the indicated time period: Step 1: 50° C. (2 min); Step 2: 95° C. (2 min); Step 3: 95° C. (15 sec); Step 4: 60° C. (1 min); then, repeat Step 3 for a total of 40 cycles.

Each mixture contained both SMN and GAPDH primers/probe sets (multiplex design) which allowed simultaneous measurement of the activity levels of both transcripts.

To calculate the fold increase of inclusion of exon 7 of SMN2 over the control, the real-time PCR data were analyzed by the $2^{-\Delta\Delta C_t}$ method (as described in Livak and Schmittgen, Methods, 2001, 25(4):402-8). The $C_T$ values of the compound-treated samples and of the control (untreated) samples were subtracted by their corresponding GAPDH $C_T$ values to calculate $\Delta C_T$. Then the average of the normalized $C_T$ values from untreated samples was calculated. The normalized $C_T$ values from compound-treated samples were subtracted from the control (untreated) average to calculate $\Delta\Delta C_T$. The fold increase of inclusion of exon 7 of SMN2 from each of the test compound samples was then calculated by $2^{-\Delta\Delta C_T}$.

Results

The results for compounds of Formula (I) are shown in Table 2. The Fold Activation results are provided as a ratio of a First Activation using the SMN-2A construct divided by a Second Activation using the SMN-2G construct, wherein 1 star (*) represents active compounds with a fold increase ratio between 1.1-1.3; 2 stars () represent active compounds with a fold increase ratio between 1.3-2.0; 3 stars (*) represent active compounds with a fold increase ratio greater than 2.0.

$$\text{First Activation} = \frac{\text{the amount or the activity of the first fusion protein expressed by the first host cell in the presence of the compound}}{\text{the amount or the activity of the first fusion protein expressed by the first host cell in the absence of the compound or the presence of a negative control}}$$

$$\text{Second Activation} = \frac{\text{the amount or the activity of the second fusion protein expressed by the second host cell in the presence of the compound}}{\text{the amount or the activity of the second fusion protein expressed by the second host cell in the absence of the compound or the presence of a negative control}}$$

The results indicate that in the presence of a compound of Formula (I), the inclusion of exon 7 of SMN2 transcribed from the SMN2-A minigene may be modulated.

TABLE 2

| Cpd | Activity |
|---|---|
| 2 | * |
| 6 | ** |
| 8 | ** |
| 11 | ** |
| 18 | * |
| 19 | ** |
| 21 | *** |
| 22 | ** |
| 23 | * |
| 24 | *** |
| 26 | ** |
| 28 | ** |
| 29 | ** |
| 30 | ** |
| 31 | ** |
| 32 | *** |
| 35 | ** |
| 36 | ** |
| 37 | * |
| 38 | *** |
| 39 | ** |
| 41 | *** |
| 42 | ** |
| 43 | ** |
| 44 | ** |
| 48 | * |
| 51 | ** |
| 52 | ** |
| 54 | ** |
| 55 | * |
| 57 | ** |
| 65 | ** |
| 66 | *** |
| 67 | ** |
| 69 | * |
| 71 | ** |
| 73 | * |
| 77 | * |
| 81 | * |
| 82 | ** |
| 89 | *** |
| 90 | ** |
| 91 | ** |
| 93 | ** |
| 100 | ** |
| 102 | ** |
| 105 | * |
| 106 | * |
| 110 | * |
| 111 | ** |
| 112 | ** |
| 128 | *** |

The present invention is not to be limited in scope by the specific embodiments described herein. Indeed, various modifications of the invention and their equivalents, in addition to those described herein will become apparent to those skilled in the art from the foregoing description and accompanying figures. Such modifications are intended to fall within the scope of the appended claims.

Various patents, patent applications, and publications are cited herein, the disclosures of which are incorporated by reference in their entirety and for all purposes.

What is claimed:

1. A nucleic acid construct comprising a minigene which comprises, in 5' to 3' order: a start codon, the nucleic acid residues of exon 6 of human survival motor neuron (SMN), the nucleic acid residues of intron 6 of human SMN, the nucleic acid residues of exon 7 of human SMN2, the nucleic acid residues of intron 7 of human SMN, a fragment of exon 8 of human SMN, and the nucleic acid residues of the coding sequence of a reporter gene lacking a start codon, wherein a single adenine residue is inserted after nucleic acid residue 48 and before nucleic acid residue 49 of the nucleic acid residues of exon 7 of human SMN2, and wherein the first codon of the coding sequence of the reporter gene and the start codon of the minigene are in the same open reading frame.

2. The nucleic acid construct of claim 1, wherein the fragment of exon 8 of human SMN consists of 23 nucleic acid residues from the 5' end of exon 8 of human SMN.

3. The nucleic acid construct of claim 1, wherein the coding sequence of the reporter gene encodes firefly luciferase, *renilla* luciferase, click beetle luciferase, a genetically modified luciferase, green fluorescent protein, yellow fluorescent protein, red fluorescent protein, cyan fluorescent protein, blue fluorescent protein, beta-galactosidase, beta-glucoronidase, beta-lactamase, chloramphenicol acetyltransferase or alkaline phosphatase.

4. The nucleic acid construct of claim 2, wherein the coding sequence of the reporter gene encodes firefly luciferase, *renilla* luciferase, click beetle luciferase, a genetically modified luciferase, green fluorescent protein, yellow fluorescent protein, red fluorescent protein, cyan fluorescent protein, blue fluorescent protein, beta-galactosidase, beta-glucoronidase, beta-lactamase, chloramphenicol acetyltransferase or alkaline phosphatase.

5. An isolated host cell containing the nucleic acid construct of any one of claims 1, 2, 3 or 4.

6. A method for the identification of a compound that increases the inclusion of exon 7 of human SMN2 into mRNA transcribed from the human SMN2 gene comprising:
 (a) contacting a compound with the host cell of claim 5; and
 (b) detecting the activity or amount of a fusion protein encoded by the minigene,
 wherein an increase in the activity or amount of the fusion protein expressed by the host cell in the presence of the compound relative to the activity or amount of the fusion protein expressed by the host cell in the absence of the compound or the presence of a negative control compound, or relative to a previously determined reference range indicates that the compound increases the inclusion of exon 7 of human SMN2 into mRNA transcribed from the human SMN2 gene.

7. A method for the identification of a compound that increases the inclusion of exon 7 of human SMN2 into mRNA transcribed from the human SMN2 gene comprising:
 (a) contacting a compound with a composition comprising a cell-free extract and a pre-mRNA transcript encoded by the minigene of the nucleic acid construct of claim 1; and
 (b) detecting the activity or amount of a fusion protein encoded by the minigene, wherein an increase in the activity or amount of the fusion protein expressed by the host cell in the presence of the compound relative to the activity or amount of the fusion protein expressed by the host cell in the absence of the compound or the presence of a negative control compound, or relative to a previously determined reference range indicates that the compound that increases the inclusion of exon 7 of human SMN2 into mRNA transcribed from the human SMN2 gene.

* * * * *

UNITED STATES PATENT AND TRADEMARK OFFICE
CERTIFICATE OF CORRECTION

PATENT NO. : 8,633,019 B2
APPLICATION NO. : 12/994517
DATED : January 21, 2014
INVENTOR(S) : Paushkin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 17 days.

Signed and Sealed this
Twenty-second Day of September, 2015

Michelle K. Lee
*Director of the United States Patent and Trademark Office*

SEQUENCE LISTING

<160> NUMBER OF SEQ ID NOS: 20

<210> SEQ ID NO 1
<211> LENGTH: 11
<212> TYPE: DNA
<213> ORGANISM: Artificial Sequence
<220> FEATURE:
<223> OTHER INFORMATION: a region of SMN2 gene at 5 prime end of exon 6

<400> SEQUENCE: 1
ataattcccc c                                                         11

<210> SEQ ID NO 2
<211> LENGTH: 6
<212> TYPE: DNA
<213> ORGANISM: Artificial Sequence
<220> FEATURE:
<223> OTHER INFORMATION: residue 23 of exon 8 of SMN2 gene

<400> SEQUENCE: 2 cagcac                                                                6

<210> SEQ ID NO 3
<211> LENGTH: 28
<212> TYPE: DNA
<213> ORGANISM: Artificial Sequence
<220> FEATURE:
<223> OTHER INFORMATION: Forward Primer for amplifying regions defined
      by SEQ ID No. 1 and SEQ ID No. 2

<400> SEQUENCE: 3
cgcggatcca taattccccc accacctc                                       28

<210> SEQ ID NO 4
<211> LENGTH: 28
<212> TYPE: DNA
<213> ORGANISM: Artificial Sequence
<220> FEATURE:
<223> OTHER INFORMATION: Reverse Primer for amplifying regions defined
      by SEQ ID No. 1 and SEQ ID No. 2

<400> SEQUENCE: 4
cgcggatccg tgctgctcta tgccagca                                       28

<210> SEQ ID NO 5
<211> LENGTH: 6
<212> TYPE: DNA
<213> ORGANISM: Artificial Sequence
<220> FEATURE:
<223> OTHER INFORMATION: BamHI site added to the primers

<400> SEQUENCE: 5 ggatcc                                                                6

<210> SEQ ID NO 6
<211> LENGTH: 70
<212> TYPE: DNA
<213> ORGANISM: Artificial Sequence
<220> FEATURE:
<223> OTHER INFORMATION: 5 prime end deg-UTR used to the modify
      pcDNA3.1/Hygrop vector

<400> SEQUENCE: 6
tagcttctta cccgtactcc accgttggca gcacgatcgc acgtcccacg tgaaccattg     60
gtaaaccctg                                                           70

```
<210> SEQ ID NO 7
<211> LENGTH: 120
<212> TYPE: DNA
<213> ORGANISM: Artificial Sequence
<220> FEATURE:
<223> OTHER INFORMATION: 3 prime end deg-UTR used to the modify
      pcDNA3.1/Hygrop vector

<400> SEQUENCE: 7
atcgaaagta caggactagc cttcctagca accgcgggct gggagtctga gacatcactc    60
aagatatatg ctcggtaacg tatgctctag ccatctaact attccctatg tcttataggg   120

<210> SEQ ID NO 8
<211> LENGTH: 7
<212> TYPE: DNA
<213> ORGANISM: Artificial Sequence
<220> FEATURE:
<223> OTHER INFORMATION: residues left out during cloning in the exon 7
      region (in front of inserted G residue)

<400> SEQUENCE: 8 gtaagga                                                                7

<210> SEQ ID NO 9
<211> LENGTH: 6
<212> TYPE: DNA
<213> ORGANISM: Artificial Sequence
<220> FEATURE:
<223> OTHER INFORMATION: sequence element generated by the G insertion

<400> SEQUENCE: 9 gtaagg                                                                 6

<210> SEQ ID NO 10
<211> LENGTH: 6
<212> TYPE: DNA
<213> ORGANISM: Artificial Sequence
<220> FEATURE:
<223> OTHER INFORMATION: 5 prime end of intron 7

<400> SEQUENCE: 10 gtaagt                                                                 6

<210> SEQ ID NO 11
<211> LENGTH: 19
<212> TYPE: DNA
<213> ORGANISM: Artificial Sequence
<220> FEATURE:
<223> OTHER INFORMATION: SMN 5 prime primer

<400> SEQUENCE: 11
gaaggaaggt gctcacatt                                                  19

<210> SEQ ID NO 12
<211> LENGTH: 21
<212> TYPE: DNA
<213> ORGANISM: Artificial Sequence
<220> FEATURE:
<223> OTHER INFORMATION: SMN 5 prime primer

<400> SEQUENCE: 12
gaaggaaggt gctcacattc c                                               21

<210> SEQ ID NO 13
<211> LENGTH: 22
```

-continued

```
<212> TYPE: DNA
<213> ORGANISM: Artificial Sequence
<220> FEATURE:
<223> OTHER INFORMATION: SMN 3 prime primer

<400> SEQUENCE: 13
gaagacgcca aaaacataaa ga                                              22

<210> SEQ ID NO 14
<211> LENGTH: 18
<212> TYPE: DNA
<213> ORGANISM: Artificial Sequence
<220> FEATURE:
<223> OTHER INFORMATION: SMN 3 prime primer

<400> SEQUENCE: 14
gatggaaccg ctggagag                                                   18

<210> SEQ ID NO 15
<211> LENGTH: 20
<212> TYPE: DNA
<213> ORGANISM: Artificial Sequence
<220> FEATURE:
<223> OTHER INFORMATION: SMN 3 prime primer

<400> SEQUENCE: 15
atagcttctg ccaaccgaac                                                 20

<210> SEQ ID NO 16
<211> LENGTH: 26
<212> TYPE: DNA
<213> ORGANISM: Artificial Sequence
<220> FEATURE:
<223> OTHER INFORMATION: SMN probe

<400> SEQUENCE: 16
aaggagaaat gctggcatag agcagc                                          26

<210> SEQ ID NO 17
<211> LENGTH: 30
<212> TYPE: DNA
<213> ORGANISM: Artificial Sequence
<220> FEATURE:
<223> OTHER INFORMATION: SMN probe

<400> SEQUENCE: 17
atataaggag aaatgctggc atagagcagc                                      30

<210> SEQ ID NO 18
<211> LENGTH: 27
<212> TYPE: DNA
<213> ORGANISM: Artificial Sequence
<220> FEATURE:
<223> OTHER INFORMATION: SMN probe

<400> SEQUENCE: 18
atataaggag aaatgctggc atagagc                                         27

<210> SEQ ID NO 19
<211> LENGTH: 8266
<212> TYPE: DNA
<213> ORGANISM: Artificial Sequence
<220> FEATURE:
<223> OTHER INFORMATION: DNA sequence of the minigene from the SMN2-G
      minigene construct

<400> SEQUENCE: 19
```

-continued

| | |
|---|---|
| tagcttctta cccgtactcc accgttggca gcacgatcgc acgtcccacg tgaaccattg | 60 |
| gtaaaccctg atgggatcca taattccccc accacctccc atatgtccag attctcttga | 120 |
| tgatgctgat gctttgggaa gtatgttaat tcatggtac atgagtggct atcatactgg | 180 |
| ctattatatg gtaagtaatc actcagcatc ttttcctgac aattttttg tagttatgtg | 240 |
| actttgtttt gtaaatttat aaaatactac ttgcttctct ctttatatta ctaaaaaata | 300 |
| aaaataaaaa aatacaactg tctgaggctt aaattactct tgcattgtcc ctaagtataa | 360 |
| ttttagttaa ttttaaaaag ctttcatgct attgttagat tattttgatt atacactttt | 420 |
| gaattgaaat tatacttttt ctaaataatg ttttaatctc tgatttgaaa ttgattgtag | 480 |
| ggaatggaaa agatgggata attttcata aatgaaaaat gaaattcttt ttttttttt | 540 |
| ttttttttg agacggagtc ttgctctgtt gcccaggctg gagtgcaatg gcgtgatctt | 600 |
| ggctcacagc aagctctgcc tcctggattc acgccattct cctgcctcag cctcagaggt | 660 |
| agctgggact acaggtgcct gccaccacgc ctgtctaatt ttttgtattt ttttgtaaag | 720 |
| acagggtttc actgtgttag ccaggatggt ctcaatctcc tgaccccgtg atccacccgc | 780 |
| ctcggccttc caagagaaat gaaatttttt taatgcacaa agatctgggg taatgtgtac | 840 |
| cacattgaac cttggggagt atggcttcaa acttgtcact ttatacgtta gtctcctacg | 900 |
| gacatgttct attgtatttt agtcagaaca tttaaaatta ttttatttta ttttattttt | 960 |
| tttttttttt tgagacggag tctcgctctg tcacccaggc tggagtacag tggcgcagtc | 1020 |
| tcggctcact gcaagctccg cctcccgggt tcacgccatt ctcctgcctc agcctctccg | 1080 |
| agtagctggg actacaggcg cccgccacca cgcccggcta attttttttt attttagta | 1140 |
| gagacggggt ttcaccgtgg tctcgatctc ctgacctcgt gatccacccg cctcggcctc | 1200 |
| ccaaagtgct gggattacaa gcgtgagcca ccgcgcccgg cctaaaatta ttttaaaag | 1260 |
| taagctcttg tgccctgcta aaattatgat gtgatattgt aggcacttgt attttagta | 1320 |
| aattaatata gaagaaacaa ctgacttaaa ggtgtatgtt tttaaatgta tcatctgtgt | 1380 |
| gtgccccat taatattctt atttaaaagt taaggccaga catggtggct tacaactgta | 1440 |
| atcccaacag tttgtgaggc cgaggcaggc agatcacttg aggtcaggag tttgagacca | 1500 |
| gcctggccaa catgatgaaa ccttgtctct actaaaaata ccaaaaaaaa tttagccagg | 1560 |
| catggtggca catgcctgta atccgagcta cttgggaggc tgtggcagga aaattgcttt | 1620 |
| aatctgggag gcagaggttg cagtgagttg agattgtgcc actgcactcc accttggtg | 1680 |
| acagagtgag attccatctc aaaaaaagaa aaaggcctgg cacggtggct cacacctata | 1740 |
| atcccagtac tttgggaggt agaggcaggt ggatcacttg aggttaggag ttcaggacca | 1800 |
| gcctggccaa catggtgact actccatttc tactaaatac acaaaactta gcccagtggc | 1860 |
| gggcagttgt aatcccagct acttgagagg ttgaggcagg agaatcactt gaacctggga | 1920 |
| ggcagaggtt gcagtgagcc gagatcacac cgctgcactc tagcctggcc aacagagtga | 1980 |
| gaatttgcgg agggaaaaaa aagtcacgct tcagttgttg tagtataacc ttggtatatt | 2040 |
| gtatgtatca tgaattcctc attttaatga ccaaaaagta ataaatcaac agcttgtaat | 2100 |
| ttgttttgag atcagttatc tgactgtaac actgtaggct tttgtgtttt ttaaattatg | 2160 |
| aaatatttga aaaaaataca taatgtatat ataaagtatt ggtataattt atgttctaaa | 2220 |
| taacttctct gagaaataat tcacatggtg tgcagtttac ctttgaaagt atacaagttg | 2280 |
| gctgggcaca atggctcacg cctgtaatcc cagcactttg ggaggccagg caggtggat | 2340 |
| cacgaggtca ggagatcgag accatcctgg ctaacatggt gaaaccccgt ctctactaaa | 2400 |

```
agtacaaaaa caaattagcc gggcatgttg gcgggcacct tttgtcccag ctgctcggga    2460
ggctgaggca ggagagtggc gtgaacccag gaggtggagc ttgcagtgag ccagagattgt   2520 gccagtgcac tccagcctgg gcgacagagc gagactctgt ctcaaaaaat aaaataaaaa   2580
agaaagtata caagtcagtg gttttggttt tcagttatgc aaccatcact acaatttaag    2640
aacattttca tcaccccaaa aagaaaccct gttaccttca ttttccccag ccctaggcag    2700
tcagtacact ttctgtctct atgaatttgt ctattttaga tattatatat aaacggaatt    2760
atacgatatg tggtcttttg tgtctggctt ctttcactta gcatgctatt ttcaagattc    2820
atccatgctg tagaatgcac cagtactgca ttccttctta ttgctgaata ttctgttgtt    2880
tggttatatc acattttatc cattcatcag ttcatggaca tttaggttgt ttttattttt    2940
gggctataat gaataatgtt gctatgaaca ttcgttgtg ttcttttgt ttttttggtt     3000 ttttgggttt tttttgtttt gttttgttt ttgagacagt cttgctctgt ctcctaagct    3060
ggagtgcagt ggcatgatct tggcttactg caagctctgc ctcccgggtt cacaccattc    3120
tcctgcctca gcccgacaag tagctgggac tacaggcgtg tgccaccatg cacggctaat    3180
tttttgtatt tttagtagag atgggggttttc accgtgttag ccaggatggt ctcgatctcc    3240
tgacctcgtg atctgcctgc ctaggcctcc caaagtgctg ggattacagg cgtgagccac    3300
tgcacctggc cttaagtgtt tttaatacgt cattgcctta agctaacaat tcttaacctt    3360
tgttctactg aagccacgtg gttgagatag gctctgagtc tagcttttaa cctctatctt    3420
tttgtcttag aaatctaagc agaatgcaaa tgactaagaa taatgttgtt gaaataacat    3480
aaaataggtt ataactttga tactcattag taacaaatct ttcaatacat cttacggtct    3540
gttaggtgta gattagtaat gaagtgggaa gccactgcaa gctagtatac atgtagggaa    3600
agatagaaag cattgaagcc agaagagaga cagaggacat ttgggctaga tctgacaaga    3660
aaaacaaatg ttttagtatt aattttttgac tttaaatttt tttttattt agtgaatact    3720 ggtgtttaat ggtctcattt taataagtat gacacaggta gtttaaggtc atatattta    3780 tttgatgaaa ataaggtata ggccgggcac ggtggctcac acctgtaatc ccagcacttt    3840
gggaggccga ggcaggcgga tcacctgagg tcgggagtta gagactagcc tcaacatgga    3900
gaaaccccgt ctctactaaa aaaaatacaa aattaggcgg gcgtggtggt gcatgcctgt    3960
aatcccagct actcaggagg ctgaggcagg agaattgctt gaacctggga ggtggaggtt    4020
gcggtgagcc gagatcacct cattgcactc cagcctgggc aacaagagca aaactccatc    4080
tcaaaaaaaa aaaataagg tataagcggg ctcaggaaca tcattggaca tactgaagaa    4140
agaaaaatca gctgggcgca gtggctcacg ccggtaatcc caacactttg ggaggccaag    4200
gcaggcgaat cacctgaagt cgggagttcc agatcagcct gaccaacatg gagaaacccct   4260 gtctctacta aaaatacaaa actagccggg catggtggcg catgcctgta atcccagcta    4320
cttgggaggc tgaggcagga gaattgcttg aaccgagaag gcggaggttg cggtgagcca    4380
agattgcacc attgcactcc agcctgggca acaagagcga aactccgtct caaaaaaaaa    4440
aggaagaaaa atattttttt aaattaatta gtttatttat ttttttaagat ggagtttgc    4500 cctgtcaccc aggctggggt gcaatggtgc aatctcggct cactgcaacc tccgcctcct    4560
gggttcaagt gattctcctg cctcagcttc ccgagtagct gtgattacag ccatatgcca    4620
ccacgcccag ccagttttgt gttttgtttt gttttttgtt ttttttttt gagagggtgt    4680 cttgctctgt cccccaagct ggagtgcagc ggcgcgatct tggctcactg caagctctgc    4740
ctcccaggtt cacaccattc tcttgcctca gcctcccgag tagctgggac tacaggtgcc    4800
```

```
cgccaccaca  cccggctaat  ttttttgtgt  ttttagtaga  gatggggttt  cactgtgtta   4860
gccaggatgg  tctcgatctc  ctgaccnttt  gatccacccg  cctcagcctc  cccaagtgct   4920
gggattatag  gcgtgagcca  ctgtgcccgg  cctagtcttg  tattttagt   agagtcggga   4980
tttctccatg  ttggtcaggc  tgttctccaa  atccgacctc  aggtgatccg  cccgccttgg   5040
cctccaaaag  tgcaaggcaa  ggcattacag  gcatgagcca  ctgtgaccgg  caatgttttt   5100
aaattttta   catttaaatt  ttattttta   gagaccaggt  ctcactctat  tgctcaggct   5160
ggagtgcaag  ggcacattca  cagctcactg  cagccttgac  ctccagggct  caagcagtcc   5220
tctcacctca  gtttcccgag  tagctgggac  tacagtgata  atgccactgc  acctggctaa   5280
tttttatttt  tatttattta  ttttttttg   agacagagtc  ttgctctgtc  acccaggctg   5340
gagtgcagtg  gtgtaaatct  cagctcactg  cagcctccgc  ctcctgggtt  caagtgattc   5400
tcctgcctca  acctcccaag  tagctgggat  tagaggtccc  accaccatg   cctggctaat   5460
tttttgtact  ttcagtagaa  acggggtttt  gccatgttgg  ccaggctgtt  ctcgaactcc   5520
tgagctcagg  tgatccaact  gtctcggcct  cccaaagtgc  tgggattaca  ggcgtgagcc   5580
actgtgccta  gcctgagcca  ccacgccggc  ctaattttta  aattttttgt  agagacaggg   5640
tctcattatg  ttgcccaggg  tggtgtcaag  ctccaggtct  caagtgatcc  ccctacctcc   5700
gcctcccaaa  gttgtgggat  tgtaggcatg  agccactgca  agaaaacctt  aactgcagcc   5760
taataattgt  tttctttggg  ataactttta  aagtacatta  aaagactatc  aacttaattt   5820
ctgatcatat  tttgttgaat  aaaataagta  aaatgtcttg  tgaaacaaaa  tgcttttaa    5880
catccatata  aagctatcta  tatatagcta  tctatatcta  tatagctatt  tttttaact   5940
tcctttattt  tccttacagg  gttttagaca  aaatcaaaaa  gaaggaaggt  gctcacattc   6000
cttaaatgta  aggagtaagt  ctgccagcat  tatgaaagtg  aatcttactt  ttgtaaaact   6060
ttatggtttg  tggaaaacaa  atgtttttga  acatttaaaa  agttcagatg  ttagaaagtt   6120
gaaaggttaa  tgtaaaacaa  tcaatattaa  agaatttga   tgccaaaact  attagataaa   6180
aggttaatct  acatccctac  tagaattctc  atacttaact  ggttggttgt  gtggaagaaa   6240
catactttca  caataaagag  ctttaggata  tgatgccatt  ttatatcact  agtaggcaga   6300
ccagcagact  ttttttttatt gtgatatggg  ataacctagg  catactgcac  tgtacactct   6360
gacatatgaa  gtgctctagt  caagtttaac  tggtgtccac  agaggacatg  gtttaactgg   6420
aattcgtcaa  gcctctggtt  ctaatttctc  atttgcagga  aatgctggca  tagagcagca   6480
cggatccgaa  gacgccaaaa  acataaagaa  aggcccggcg  ccattctatc  ctctagagga   6540
tggaaccgct  ggagagcaac  tgcataaggc  tatgaagaga  tacgccctgg  ttcctggaac   6600
aattgctttt  acagatgcac  atatcgaggt  gaacatcacg  tacgcggaat  acttcgaaat   6660
gtccgttcgg  ttggcagaag  ctatgaaacg  atatgggctg  aatacaaatc  acagaatcgt   6720
cgtatgcagt  gaaaactctc  ttcaattctt  tatgccggtg  ttgggcgcgt  tatttatcgg   6780
agttgcagtt  gcgcccgcga  acgacattta  taatgaacgt  gaattgctca  acagtatgaa   6840
catttcgcag  cctaccgtag  tgtttgtttc  caaaaagggg  ttgcaaaaaa  ttttgaacgt   6900
gcaaaaaaaa  ttaccaataa  tccagaaaat  tattatcatg  gattctaaaa  cggattacca   6960
gggatttcag  tcgatgtaca  cgttcgtcac  atctcatcta  cctcccggtt  ttaatgaata   7020
cgattttgta  ccagagtcct  ttgatcgtga  caaaacaatt  gcactgataa  tgaattcctc   7080
tggatctact  gggttaccta  agggtgtggc  ccttccgcat  agaactgcct  gcgtcagatt   7140
ctcgcatgcc  agagatccta  ttttggcaa   tcaaatcatt  ccggatactg  cgattttaag   7200
```

```
tgttgttcca ttccatcacg gttttggaat gtttactaca ctcggatatt tgatatgtgg   7260
atttcgagtc gtcttaatgt atagatttga agaagagctg ttttacgat cccttcagga    7320 ttacaaaatt caaagtgcgt tgctagtacc aaccctattt tcattcttcg ccaaaagcac   7380
tctgattgac aaatacgatt tatctaattt acacgaaatt gcttctgggg gcgcacctct   7440
ttcgaaagaa gtcggggaag cggttgcaaa acgcttccat cttccaggga tacgacaagg   7500
atatgggctc actgagacta catcagctat tctgattaca cccgaggggg atgataaacc   7560
gggcgcggtc ggtaaagttg ttccattttt tgaagcgaag gttgtggatc tggataccgg   7620
gaaaacgctg ggcgttaatc agagaggcga attatgtgtc agaggaccta tgattatgtc   7680
cggttatgta aacaatccgg aagcgaccaa cgccttgatt gacaaggatg gatggctaca   7740
ttctggagac atagcttact gggacgaaga cgaacacttc ttcatagttg accgcttgaa   7800
gtctttaatt aaatacaaag gatatcaggt ggcccccgct gaattggaat cgatattgtt   7860
acaacacccc aacatcttcg acgcgggcgt ggcaggtctt cccgacgatg acgccggtga   7920
acttcccgcc gccgttgttg ttttggagca cggaaagacg atgacggaaa aagagatcgt   7980
ggattacgtc gccagtcaag taacaaccgc gaaaaagttg cgcggaggag ttgtgtttgt   8040
ggacgaagta ccgaaaggtc ttaccggaaa actcgacgca agaaaaatca gagagatcct   8100
cataaaggcc aagaagggcg gaaagtccaa attgcgcggc cgctaaatcg aaagtacagg   8160
actagccttc ctagcaaccg cgggctggga gtctgagaca tcactcaaga tatatgctcg   8220
gtaacgtatg ctctagccat ctaactattc cctatgtctt ataggg                  8266

<210> SEQ ID NO 20
<211> LENGTH: 8266
<212> TYPE: DNA
<213> ORGANISM: Artificial Sequence
<220> FEATURE:
<223> OTHER INFORMATION: DNA sequence of the minigene from the SMN2-A
      minigene construct

<400> SEQUENCE: 20
tagcttctta cccgtactcc accgttggca gcacgatcgc acgtcccacg tgaaccattg     60
gtaaaccctg atgggatcca taattccccc accacctccc atatgtccag attctcttga   120
tgatgctgat gctttgggaa gtatgttaat ttcatggtac atgagtggct atcatactgg   180
ctattatatg gtaagtaatc actcagcatc ttttcctgac aatttttttg tagttatgtg   240
actttgtttt gtaaatttat aaaatactac ttgcttctct ctttatatta ctaaaaaata   300
aaaataaaaa aatacaactg tctgaggctt aaattactct tgcattgtcc ctaagtataa   360
ttttagttaa ttttaaaaag ctttcatgct attgttagat tattttgatt atacactttt   420
gaattgaaat tatactttt ctaaataatg ttttaatctc tgatttgaaa ttgattgtag    480
ggaatggaaa agatgggata atttttcata aatgaaaaat gaaattcttt tttttttttt   540
tttttttttg agacggagtc ttgctctgtt gcccaggctg gagtgcaatg gcgtgatctt   600
ggctcacagc aagctctgcc tcctggattc acgccattct cctgcctcag cctcagaggt   660
agctgggact acaggtgcct gccaccacgc ctgtctaatt ttttgtattt ttttgtaaag   720
acagggtttc actgtgttag ccaggatggt ctcaatctcc tgaccccgtg atccacccgc   780
ctcggccttc aagagaaat gaatttttt taatgcacaa agatctgggg taatgtgtac    840
cacattgaac cttggggagt atggcttcaa acttgtcact ttatacgtta gtctcctacg   900
gacatgttct attgtatttt agtcagaaca tttaaaatta ttttatttta ttttatttt    960 ttttttttttt tgagacggag tctcgctctg tcacccaggc tggagtacag tggcgcagtc  1020
```

```
tcggctcact gcaagctccg cctcccgggt tcacgccatt ctcctgcctc agcctctccg    1080
agtagctggg actacaggcg cccgccacca cgcccggcta atttttttt atttttagta    1140 gagacggggt ttcaccgtgg tctcgatctc ctgacctcgt gatccacccg cctcggcctc    1200
ccaaagtgct gggattacaa gcgtgagcca ccgcgcccgg cctaaaatta ttttaaaag    1260 taagctcttg tgccctgcta aaattatgat gtgatattgt aggcacttgt attttagta    1320 aattaatata gaagaaacaa ctgacttaaa ggtgtatgtt tttaaatgta tcatctgtgt    1380 gtgccccat taatattctt atttaaaagt taaggccaga catggtggct tacaactgta    1440
atcccaacag tttgtgaggc cgaggcaggc agatcacttg aggtcaggag tttgagacca    1500
gcctggccaa catgatgaaa ccttgtctct actaaaaata ccaaaaaaaa tttagccagg    1560
catggtggca catgcctgta atcccagcta cttgggaggc tgtggcagga aaattgcttt    1620
aatctgggag gcagaggttg cagtgagttg agattgtgcc actgcactcc acccttggtg    1680
acagagtgag attccatctc aaaaaaagaa aaaggcctgg cacggtggct cacacctata    1740
atcccagtac tttgggaggt agaggcaggt ggatcacttg aggttaggag ttcaggacca    1800
gcctggccaa catggtgact actccatttc tactaaatac acaaaactta gcccagtggc    1860
gggcagttgt aatcccagct acttgagagg ttgaggcagg agaatcactt gaacctggga    1920
ggcagaggtt gcagtgagcc gagatcacac cgctgcactc tagcctggcc aacagagtga    1980
gaatttgcgg agggaaaaaa aagtcacgct tcagttgttg tagtataacc ttggtatatt    2040
gtatgtatca tgaattcctc attttaatga ccaaaaagta ataaatcaac agcttgtaat    2100
ttgttttgag atcagttatc tgactgtaac actgtaggct tttgtgtttt ttaaattatg    2160
aaatatttga aaaaaataca taatgtatat ataaagtatt ggtataattt atgttctaaa    2220
taactttctt gagaaataat tcacatggtg tgcagtttac ctttgaaagt atacaagttg    2280
gctgggcaca atggctcacg cctgtaatcc cagcactttg ggaggccagg caggtggat    2340 cacgaggtca ggagatcgag accatcctgg ctaacatggt gaaacccccgt ctctactaaa    2400 agtacaaaaa caaattagcc gggcatgttg gcgggcacct tttgtcccag ctgctcggga    2460
ggctgaggca ggagagtggc gtgaacccag gaggtggagc ttgcagtgag ccgagattgt    2520
gccagtgcac tccagcctgg gcgacagagc gagactctgt ctcaaaaaat aaaataaaaa    2580
agaaagtata caagtcagtg gttttggttt tcagttatgc aaccatcact acaatttaag    2640 aacatttttca tcaccccaaa aagaaaccct gttaccttca ttttccccag ccctaggcag    2700
tcagtacact ttctgtctct atgaatttgt ctattttaga tattatatat aaacggaatt    2760
atacgatatg tggtcttttg tgtctggctt ctttcactta gcatgctatt ttcaagattc    2820
atccatgctg tagaatgcac cagtactgca ttccttctta ttgctgaata ttctgttgtt    2880
tggttatatc acattttatc cattcatcag ttcatggaca tttaggttgt ttttattttt    2940
gggctataat gaataatgtt gctatgaaca ttcgtttgtg ttcttttgt tttttggtt    3000 ttttgggttt tttttgtttt gttttgtttt ttgagacagt cttgctctgt ctcctaagct    3060
ggagtgcagt ggcatgatct tggcttactg caagctctgc ctcccgggtt cacaccattc    3120
tcctgcctca gcccgacaag tagctgggac tacaggcgtg tgccaccatg cacggctaat    3180
tttttgtatt tttagtagag atggggtttc accgtgttag ccaggatggt ctcgatctcc    3240
tgacctcgtg atctgcctgc ctaggcctcc caaagtgctg ggattacagg cgtgagccac    3300
tgcacctggc cttaagtgtt tttaatacgt cattgcctta gctaacaat tcttaacctt    3360 tgttctactg aagccacgtg gttgagatag gctctgagtc tagcttttaa cctctatctt    3420
```

```
tttgtcttag aaatctaagc agaatgcaaa tgactaagaa taatgttgtt gaaataacat    3480
aaaataggtt ataactttga tactcattag taacaaatct ttcaatacat cttacggtct    3540
gttaggtgta gattagtaat gaagtgggaa gccactgcaa gctagtatac atgtagggaa    3600
agatagaaag cattgaagcc agaagagaga cagaggacat ttgggctaga tctgacaaga    3660
aaaacaaatg ttttagtatt aattttttgac tttaaatttt tttttttattt agtgaatact    3720 ggtgtttaat ggtctcattt taataagtat gacacaggta gtttaaggtc atatatttta    3780
tttgatgaaa ataaggtata ggccgggcac ggtggctcac acctgtaatc ccagcacttt    3840
gggaggccga ggcaggcgga tcacctgagg tcgggagtta gagactagcc tcaacatgga    3900
gaaaccccgt ctctactaaa aaaaatacaa aattaggcgg gcgtggtggt gcatgcctgt    3960
aatcccagct actcaggagg ctgaggcagg agaattgctt gaacctggga ggtggaggtt    4020
gcggtgagcc gagatcacct cattgcactc cagcctgggc aacaagagca aaactccatc    4080
tcaaaaaaaa aaaaataagg tataagcggg ctcaggaaca tcattggaca tactgaaaga    4140
agaaaaatca gctgggcgca gtggctcacg ccggtaatcc caacactttg ggaggccaag    4200
gcaggcgaat cacctgaagt cgggagttcc agatcagcct gaccaacatg gagaaaccct    4260
gtctctacta aaaatacaaa actagccggg catggtggcg catgcctgta atcccagcta    4320
cttgggaggc tgaggcagga gaattgcttg aaccgagaag gcggaggttg cggtgagcca    4380
agattgcacc attgcactcc agcctgggca acaagagcga aactccgtct caaaaaaaaa    4440
aggaagaaaa atatttttt aaattaatta gtttatttat tttttaagat ggagttttgc    4500
cctgtcaccc aggctggggt gcaatggtgc aatctcggct cactgcaacc tccgcctcct    4560
gggttcaagt gattctcctg cctcagcttc ccgagtagct gtgattacag ccatatgcca    4620
ccacgcccag ccagttttgt gttttgtttt gttttttgtt ttttttttt gagagggtgt    4680 cttgctctgt cccccaagct ggagtgcagc ggcgcgatct tggctcactg caagctctgc    4740
ctcccaggtt cacaccattc tcttgcctca gcctcccgag tagctgggac tacaggtgcc    4800
cgccaccaca cccggctaat ttttttgtgt tttagtaga gatggggttt cactgtgtta    4860
gccaggatgg tctcgatctc ctgacctttt gatccacccg cctcagcctc ccaagtgct    4920 gggattatag gcgtgagcca ctgtgccgg cctagtcttg tattttagt agagtcggga    4980 tttctccatg ttggtcaggc tgttctccaa atccgacctc aggtgatccg cccgccttgg    5040
cctccaaaag tgcaaggcaa ggcattacag gcatgagcca ctgtgaccgg caatgttttt    5100
aaatttttta catttaaatt ttattttta gagaccaggt ctcactctat tgctcaggct    5160
ggagtgcaag gcacattca cagctcactg cagccttgac ctccagggct caagcagtcc    5220
tctcacctca gtttcccgag tagctgggac tacagtgata atgccactgc acctggctaa    5280 ttttttatttt tatttattta tttttttttg agacagagtc ttgctctgtc acccaggctg    5340
gagtgcagtg gtgtaaatct cagctcactg cagcctccgc ctcctgggtt caagtgattc    5400
tcctgcctca acctcccaag tagctgggat tagaggtccc caccaccatg cctggctaat    5460
tttttgtact ttcagtagaa acggggtttt gccatgttgg ccaggctgtt ctcgaactcc    5520
tgagctcagg tgatccaact gtctcggcct cccaaagtgc tgggattaca ggcgtgagcc    5580
actgtgccta gcctgagcca ccacgccggc ctaattttta aattttttgt agagacaggg    5640
tctcattatg ttgcccaggg tggtgtcaag ctccaggtct caagtgatcc cctacctcc    5700 gcctcccaaa gttgtgggat tgtaggcatg agccactgca agaaacctt aactgcagcc    5760 taataattgt tttctttggg ataactttta aagtacatta aaagactatc aacttaattt    5820
```

```
ctgatcatat tttgttgaat aaaataagta aaatgtcttg tgaaacaaaa tgcttttaa    5880
catccatata aagctatcta tatatagcta tctatatcta tatagctatt tttttaact    5940
tcctttattt tccttacagg gttttagaca aaatcaaaaa gaaggaaggt gctcacattc    6000
cttaaatata aggagtaagt ctgccagcat tatgaaagtg aatcttactt ttgtaaaact    6060
ttatggtttg tggaaaacaa atgtttttga acatttaaaa agttcagatg ttagaaagtt    6120
gaaaggttaa tgtaaaacaa tcaatattaa agaattttga tgccaaaact attagataaa    6180
aggttaatct acatccctac tagaattctc atacttaact ggttggttgt gtggaagaaa    6240
catactttca caataaagag ctttaggata tgatgccatt ttatatcact agtaggcaga    6300
ccagcagact ttttttttatt gtgatatggg ataacctagg catactgcac tgtacactct    6360
gacatatgaa gtgctctagt caagtttaac tggtgtccac agaggacatg gtttaactgg    6420
aattcgtcaa gcctctggtt ctaatttctc atttgcagga aatgctggca tagagcagca    6480
cggatccgaa gacgccaaaa acataaagaa aggcccggcg ccattctatc ctctagagga    6540
tggaaccgct ggagagcaac tgcataaggc tatgaagaga tacgccctgg ttcctggaac    6600
aattgctttt acagatgcac atatcgaggt gaacatcacg tacgcggaat acttcgaaat    6660
gtccgttcgg ttggcagaag ctatgaaacg atatgggctg aatacaaatc acagaatcgt    6720
cgtatgcagt gaaaactctc ttcaattctt tatgccggtg ttgggcgcgt tatttatcgg    6780
agttgcagtt gcgcccgcga acgacattta taatgaacgt gaattgctca acagtatgaa    6840
catttcgcag cctaccgtag tgtttgtttc caaaaagggg ttgcaaaaaa ttttgaacgt    6900
gcaaaaaaaa ttaccaataa tccagaaaat tattatcatg gattctaaaa cggattacca    6960
gggatttcag tcgatgtaca cgttcgtcac atctcatcta cctcccggtt ttaatgaata    7020
cgattttgta ccagagtcct ttgatcgtga caaaacaatt gcactgataa tgaattcctc    7080
tggatctact gggttaccta agggtgtggc ccttccgcat agaactgcct gcgtcagatt    7140
ctcgcatgcc agagatccta ttttttggcaa tcaaatcatt ccggatactg cgattttaag    7200
tgttgttcca ttccatcacg gttttggaat gtttactaca ctcggatatt tgatatgtgg    7260
atttcgagtc gtcttaatgt atagatttga agaagagctg ttttttacgat cccttcagga    7320
ttacaaaatt caaagtgcgt tgctagtacc aaccctattt tcattcttcg ccaaaagcac    7380
tctgattgac aaatacgatt tatctaattt acacgaaatt gcttctgggg gcgcacctct    7440
ttcgaaagaa gtcggggaag cggttgcaaa acgcttccat cttccaggga tacgacaagg    7500
atatgggctc actgagacta catcagctat tctgattaca cccgaggggg atgataaacc    7560
gggcgcggtc ggtaaagttg ttccattttt tgaagcgaag gttgtggatc tggataccgg    7620
gaaaacgctg ggcgttaatc agagaggcga attatgtgtc agaggaccta tgattatgtc    7680
cggttatgta aacaatccgg aagcgaccaa cgccttgatt gacaaggatg gatggctaca    7740
ttctggagac atagcttact gggacgaaga cgaacacttc ttcatagttg accgcttgaa    7800
gtctttaatt aaatacaaag gatatcaggt ggccccccgct gaattggaat cgatattgtt    7860
acaacacccc aacatcttcg acgcgggcgt ggcaggtctt cccgacgatg acgccggtga    7920
acttcccgcc gccgttgttg ttttggagca cggaaagacg atgacggaaa aagagatcgt    7980
ggattacgtc gccagtcaag taacaaccgc gaaaaagttg cgcggaggag ttgtgtttgt    8040
ggacgaagta ccgaaaggtc ttaccggaaa actcgacgca agaaaaatca gagagatcct    8100
```

```
cataaaggcc aagaagggcg gaaagtccaa attgcgcggc cgctaaatcg aaagtacagg    8160
actagccttc ctagcaaccg cgggctggga gtctgagaca tcactcaaga tatatgctcg    8220
gtaacgtatg ctctagccat ctaactattc cctatgtctt ataggg                  8266
```